(12) United States Patent
Bursulaya et al.

(10) Patent No.: US 10,112,907 B2
(45) Date of Patent: Oct. 30, 2018

(54) SUBSTITUTED INDAZOLES FOR TREATING TENDON AND/OR LIGAMENT INJURIES

(71) Applicant: NOVARTIS AG, Basel (CH)

(72) Inventors: Badry Bursulaya, Escondido, CA (US); Andreas Fisch, Basel (CH); James Paul Lajiness, San Diego, CA (US); Rainer Machauer, Freiburg (DE); Swapnil Malekar, Emeryville, CA (US); Hank Michael James Petrassi, San Diego, CA (US); Farshad Ramazani, Basel (CH); Anne-Catherine Remond, Bartenheim (FR); Thomas Ullrich, Bottmingen (CH); Peggy Usselmann, Wahlbach (FR); Eric Vangrevelinghe, Saint-Louis (FR)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/711,984

(22) Filed: Sep. 21, 2017

(65) Prior Publication Data

US 2018/0086716 A1 Mar. 29, 2018

Related U.S. Application Data

(60) Provisional application No. 62/398,869, filed on Sep. 23, 2016.

(51) Int. Cl.
| | | |
|---|---|---|
| A61K 31/416 | (2006.01) | |
| C07D 231/56 | (2006.01) | |
| A61K 9/00 | (2006.01) | |
| A61K 9/16 | (2006.01) | |
| A61K 31/454 | (2006.01) | |
| C07D 401/12 | (2006.01) | |
| C07D 403/12 | (2006.01) | |
| C07D 405/12 | (2006.01) | |

(52) U.S. Cl.
CPC ......... C07D 231/56 (2013.01); A61K 9/0019 (2013.01); A61K 9/1647 (2013.01); A61K 31/416 (2013.01); A61K 31/454 (2013.01); C07D 401/12 (2013.01); C07D 403/12 (2013.01); C07D 405/12 (2013.01)

(58) Field of Classification Search
CPC .............................. A61K 31/46; C07D 231/56
USPC ........................................ 514/408; 548/362.1
See application file for complete search history.

(56) References Cited

U.S. PATENT DOCUMENTS

2007/0232620 A1  10/2007  Dorsch et al.

FOREIGN PATENT DOCUMENTS

| WO | 2002/50073 A1 | 6/2002 |
|---|---|---|
| WO | 2006/002434 A2 | 1/2006 |
| WO | 2006/003276 A1 | 1/2006 |
| WO | 2007/017577 A1 | 2/2007 |
| WO | 2008/154241 A1 | 12/2008 |
| WO | 2010/068287 A2 | 6/2010 |
| WO | 2011/019780 A1 | 2/2011 |
| WO | 2012/064642 A1 | 5/2012 |
| WO | 2012/158810 A1 | 11/2012 |

OTHER PUBLICATIONS

Antonysamy, S. et al., Fragment-based discovery of JAK-2 inhibitors. Bioorganic & Medicinal Chemistry Letters. 2009;19: 279-282.
Argiriadi, M. A. et al., Enabling structure-based drug design of Tyk2 through co-crystallization with a stabilizing aminoindazole inhibitor. BMC Structural Biology. 2012;12/22:1-11.
Caballero, J. et al.,Binding Studies and Quantitative Structure-Activity Relationship of 3-Amino-1H-Indazoles as Inhibitors of GSK3β. Chem Biol Drug Des. 2011;78:631-641.
Deng, X. et al., An amino-indazole scaffold with spectrum selective kinase inhibition of FLT3, PDGFRα and kit. Bioorganic & Medicinal Chemistry Letters. 2012; 22:4579-4584.
Witherington, J. et al., 5-Aryl-pyrazolo[3,4-b]pyridazines: Potent Inhibitors of Glycogen Synthase Kinase-3 (GSK-3). Bioorganic & Medicinal Chemistry Letters. 2003;13:1581-1584.
Witherington, J. et al., 5-Aryl-pyrazolo[3,4-b]pyridazines: Potent Inhibitors of Glycogen Synthase Kinase-3 (GSK-3). Bioorganic & Medicinal Chemistry Letters. 2003;13:1577-1580.
Yogo, T. et al., Structure-Based Design and Synthesis of 3-Amino-1,5-dihydro-4H-pyrazolopyridin-4-one Derivatives as Tyrosine Kinase 2 Inhibitors. Journal of Medicinal Chemistry. Dec. 1, 2015; (pp. 1-17=A-Q).
Halland, N., et al., Discovery of N-[4-(1H-Pyrazolo[3,4-b]pyrazin-6-yl)-phenyl]-sulfonamides as Highly Active and Selective SGK1 Inhibitors. Medicinal Chemistry Letters. 2014 (6) 73-78.
Nourissat, Geoffroy et al.: "Tendon injury: from biology to tendon repair", Nature Reviews Rheumatology, Jan. 1, 2015, vol. 11, No. 4, pp. 223-233.
International Search Report and Written Opinion, dated Jan. 2, 2018 in International patent application No. PCT/IB2017/055735, filed Sep. 21, 2017.

*Primary Examiner* — Douglas M Willis
(74) *Attorney, Agent, or Firm* — Asimina T. Georges Evangelinos

(57) ABSTRACT

The present invention provides a compound of formula (I) in free form or in pharmaceutically acceptable salt form

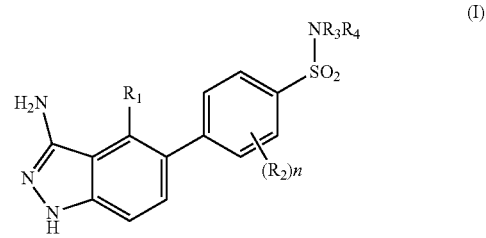

a method for manufacturing the compounds of the invention, and its therapeutic uses. The present invention further provides a combination of pharmacologically active agents and a pharmaceutical composition.

16 Claims, 2 Drawing Sheets

Specification includes a Sequence Listing.

SUBSTITUTED INDAZOLES FOR TREATING TENDON AND/OR LIGAMENT INJURIES

CLAIM OF PRIORITY

This application claims priority to U.S. Ser. No. 62/398,869 filed Sep. 23, 2016, which is incorporated herein by reference in its entirety.

FIELD OF THE INVENTION

The invention provides indazole compounds, the use thereof for treating tendon and/or ligament injuries and methods of treating tendon and/or ligament injuries using said compounds.

BACKGROUND OF THE INVENTION

Tendons and ligaments constitute an essential part of the musculoskeletal system by connecting muscles to bones, and bones to bones respectively. Both tendons and ligaments are generated through the same differentiation process (Schweitzer, R. et al. Development, 2001 October; 128(19): 3855-66). While a number of specific growth factors and transcription factors have been found to be involved in tenogenesis during development and repair processes, a detailed understanding of tendon pathologies is still in its infancy.

A review of tendon biology (Duprez D. et al., Nature, 2015, 11, 223-233) summarizes the advances made in tendon biology to date and highlights that there still remains a need for effective treatments of tendon injuries.

To date, the standard of care for tendon rupture is surgery while physiotherapy is being used for tendon degeneration.

Cell therapies and platelet rich plasma are amongst the approaches currently undergoing clinical trials for tendon injuries.

SUMMARY OF THE INVENTION

There is a need to develop compounds which are useful in treating tendon and ligament injuries. Such compound would find applications inter alia in the treatment of tendon and ligament injuries, particularly for tendon and ligament repair.

The invention provides compounds, pharmaceutically acceptable salts thereof, pharmaceutical compositions thereof and combinations thereof, which compounds are inducers of scleraxis gene expression. The invention further provides methods of treating tendon and/or ligament injuries comprising administering to a subject in need thereof an effective amount of a compound of the invention.

Various embodiments of the invention are described herein.

Within certain aspects, provided herein is a compound of formula (I) in free form or in pharmaceutically acceptable salt form:

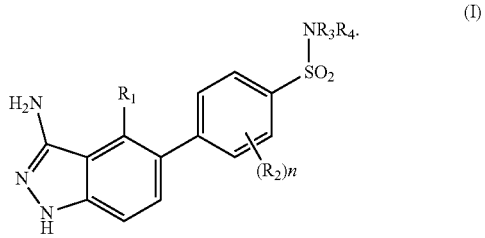

(I)

In another embodiment, the invention provides a pharmaceutical composition comprising a therapeutically effective amount of a compound according to the definition of formula (I) in free form or in pharmaceutically acceptable salt form, or subformulae thereof (I-1), (II), (II-1), (III), (III-1) as defined herein and one or more pharmaceutically acceptable carriers.

In another embodiment, the invention provides a combination, in particular a pharmaceutical combination, comprising a therapeutically effective amount of a compound according to the definition of formula (I) in free form or in pharmaceutically acceptable salt form or subformulae thereof (I-1), (II), (II-1), (III), (III-1) as defined herein and one or more therapeutically active agent.

In yet another embodiment, the invention relates to a method of treating a tendon injury in a subject in need thereof, the method comprising administering to the subject a therapeutically effective amount of a compound according to the definition of formula (I) in free form or in pharmaceutically acceptable salt form or subformulae thereof (I-1), (II), (II-1), (III), (III-1) as defined herein.

In yet another embodiment, the invention relates to a method of treating a ligament injury in a subject in need thereof, the method comprising administering to the subject a therapeutically effective amount of a compound according to the definition of formula (I) in free form or in pharmaceutically acceptable salt form or subformulae thereof (I-1), (II), (II-1), (III), (III-1) as defined herein.

In another embodiment, the invention provides a compound according to the definition of formula (I) in free form or in pharmaceutically acceptable salt form, or subformulae thereof (I-1), (II), (II-1), (III), (III-1) for use as a medicament.

In another embodiment, the invention provides a compound according to the definition of formula (I) in free form or in pharmaceutically acceptable salt form, or subformulae thereof (I-1), (II), (II-1), (III), (III-1) for use in the treatment of tendon injury.

In another embodiment, the invention provides a compound according to the definition of formula (I) in free form or in pharmaceutically acceptable salt form, or subformulae thereof (I-1), (II), (II-1), (III), (III-1) for use in the treatment of ligament injury.

In another embodiment, the invention provides the use of a compound according to the definition of formula (I) in free form or in pharmaceutically acceptable salt form, or subformulae thereof (I-1), (II), (II-1), (III), (III-1) in the manufacture of a medicament for the treatment of tendon and/or ligament injury.

DETAILED DESCRIPTION OF THE INVENTION

Figure 1A:
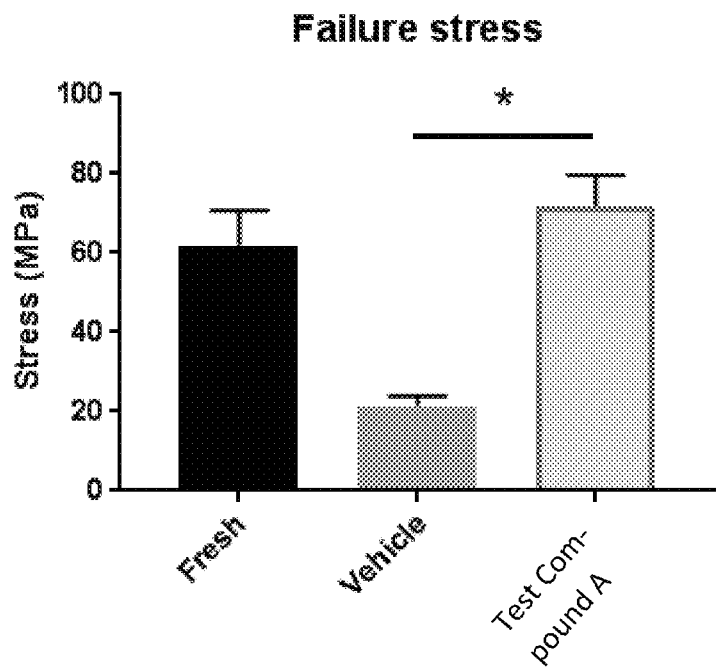
FIG. 1A shows the Failure Stress data obtained with the compound of Example 32 ("Test Compound") in graphic form in an Ex vivo fascicle assay described in Example 93 (D).

The invention therefore provides a compound of formula (I) in free form or in pharmaceutically acceptable salt form

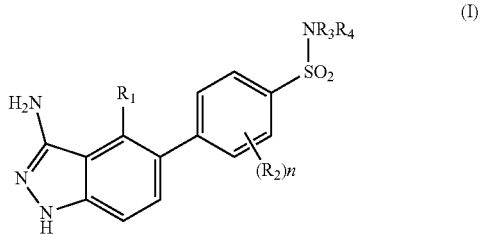

(I)

wherein, $R_1$ is selected from $C_1$-$C_3$alkyl, halogen and $C_1$-$C_3$alkoxy;

$R_2$ is independently selected from $C_1$-$C_3$alkyl and halogen;

n is 1 or 2;

$R_3$ is selected from H and $C_1$-$C_3$alkyl, and $R_4$ is selected from a $C_4$-$C_6$cycloalkyl optionally substituted once or more than once with $R_5$; a 5- or 6-membered heterocyclic non-aromatic ring comprising at least one heteroatom selected from N, O or S, optionally substituted once or more than once independently with hydroxyl, $C_1$-$C_3$alkyl, $C_1$-$C_3$alkoxy; wherein $R_4$ is not 4-hydroxycyclohexyl or tetrahydrofuran;

or $R_3$ and $R_4$ together with the N atom to which they are attached form a 4-, 5- or 6-membered heterocyclic non-aromatic ring optionally comprising one additional heteroatom selected from N, O or S, said ring being substituted once or more than once with Re;

$R_5$ is independently selected from hydroxyl, halo$C_1$-$C_3$alkyl, halogen, $C_1$-$C_2$alkyl, phenyl, benzyl, $C_3$-$C_6$cycloalkyl, cyano;

$R_6$ is independently selected from halogen, hydroxy$C_1$-$C_3$alkyl, C(O)NH$_2$, hydroxyl, $C_1$-$C_3$alkyl, cyano, halo$C_1$-$C_3$alkyl.

Unless specified otherwise, the terms "compound(s) of the present invention" or "compound(s) of the invention" refer to compound(s) of formula (I), or subformulae thereof (I-1), (II), (II-1), (III), (III-1) and salts thereof, as well as all stereoisomers (including diastereoisomers and enantiomers), rotamers, tautomers, isomeric internal addition products and isotopically labeled compounds (including deuterium substitutions), as well as inherently formed moieties.

As used herein, the term "$C_1$-$C_3$alkyl" refers to a straight or branched hydrocarbon chain radical consisting solely of carbon and hydrogen atoms, containing no unsaturation, having from one to three carbon atoms, and which is attached to the rest of the molecule by a single bond. The term "$C_1$-$C_2$alkyl" is to be construed accordingly. Examples of $C_1$-$C_3$alkyl include methyl, ethyl, n-propyl, 1-methylethyl (iso-propyl).

As used herein, the term "hydroxy$C_1$-$C_3$alkyl" refers to a radical of formula —$R_a$—OH, wherein $R_a$ is $C_{1-3}$alkyl as defined above. Examples of hydroxy$C_1$-$C_3$alkyl include, but are not limited to, hydroxy-methyl, 2-hydroxy-ethyl, 2-hydroxy-propyl, 3-hydroxy-propyl.

As used herein, the term "$C_3$-$C_6$cycloalkyl" refers to saturated monocyclic hydrocarbon groups of 3-6 carbon atoms. The term "$C_4$-$C_6$cycloalkyl" is to be construed accordingly. Examples of $C_3$-$C_6$cycloalkyl include cyclopropyl, cyclobutyl, cyclopentyl and cyclohexyl.

As used herein, the term "$C_1$-$C_3$alkoxy" refers to a radical of the formula —$OR_a$ where $R_a$ is a $C_1$-$C_3$alkyl radical as generally defined above. Examples of $C_1$-$C_3$alkoxy include, but are not limited to, methoxy, ethoxy, propoxy, iso-propoxy.

As used herein, "halogen" or "halo" refers to bromo, chloro, fluoro or iodo.

As used herein, the term "halogen$C_1$-$C_3$alkyl" or "halo$C_1$-$C_3$alkyl" refers to $C_1$-$C_3$alkyl radical, as defined above, substituted by one or more halo radicals, as defined above. Examples of halogen$C_1$-$C_3$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "meso" refers to a non-optically active isomer comprising at least 2 stereocenters.

As used herein, the term "5- or 6-membered heterocyclic non-aromatic ring comprising at least one heteroatom selected form N, O or S" when referring to $R_4$ refers to a 5-membered saturated or unsaturated ring comprising at least one heteroatom selected from N, O or S wherein the ring is attached to the rest of the molecule via a ring carbon atom or a 6-membered saturated or unsaturated ring comprising at least one heteroatom selected from N, O or S wherein the ring is attached to the rest of the molecule via a ring carbon atom and includes, but is not limited to, tetrahydropyran, pyrrolidine.

As used herein the term "4-, 5- or 6-membered heterocyclic non-aromatic ring optionally comprising one additional heteroatom selected from N, O or S" when referring to $R_3$ and $R_4$ together with the N atom to which they are attached, refers to a 4-, 5- or 6-membered N-containing saturated or unsaturated ring optionally comprising one additional heteroatom selected from N, O or S and includes, but is not limited to, azetidine, pyrrolidine, piperidine, morpholine. Preferably, it is pyrrolidine.

As used herein, the term "optionally substituted once or more than once" preferably means once, twice or three times.

As used herein, "tendon" refers to the connective tissue that connects muscle to bone and is capable of withstanding tension. Preferably, the tendon refers to the Achilles tendon or to a rotator cuff tendon.

As used herein, "ligament" refers to the connective tissue that connects bone to bone.

As used herein, the term "tendon injury" or "tendon injuries" includes both acute and chronic injuries. Acute injuries are the result of a traumatic event leading for example to partial or full rupture of the tendon. Chronic injuries are those leading to tendon degeneration without rupture of the tendon. Acute injuries can also occur on top of chronic injuries leading to possible subsequent partial or full rupture of the degenerated tendon.

As used herein, the term "ligament injury" or "ligament injuries" includes both acute and chronic injuries. Acute injuries are the result of a traumatic event leading for example to partial or full rupture of the ligament. Chronic injuries are those leading to ligament degeneration without rupture of the ligament. Acute injuries can also occur on top of chronic injuries leading to possible subsequent partial or full rupture of the degenerated ligament.

As used herein, the term "tenogenesis" refers to the generation of tendon or ligament tissue. Tenogenesis may be achieved by induction of scleraxis gene expression, tenomodulin gene expression and/or collagen type I (Col1a2).

In an embodiment, the invention relates to a compound of formula (I-1) in free form or in pharmaceutically acceptable salt form

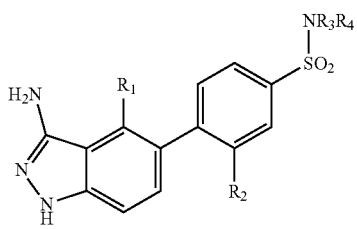

(I-1)

wherein $R_1$, $R_2$, $R_3$ and $R_4$ are as defined herein in relation to a compound of formula (I).

In an embodiment, the invention relates to a compound of formula (II) in free form or in pharmaceutically acceptable salt form

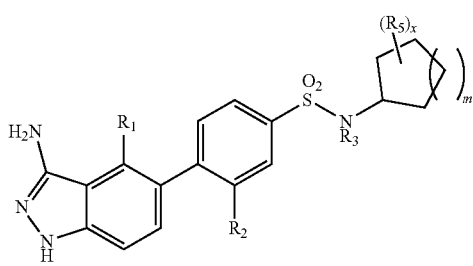

(II)

wherein
$R_1$, $R_2$, $R_3$, $R_5$ are as defined herein in relation to a compound of formula (I),
m is 0, 1, or 2 and
x is 1 or 2.

In an embodiment, the invention relates to a compound of formula (II) in free form or in pharmaceutically acceptable salt form wherein
$R_1$, $R_2$, $R_3$ are as defined herein in relation to a compound of formula (I),
$R_5$ is independently selected from hydroxyl, haloC$_1$-C$_3$alkyl, halogen, C$_1$-C$_2$alkyl;
m is 0 or 1; and
x is 1 or 2.

In an embodiment, the invention relates to a compound of formula (II-1)

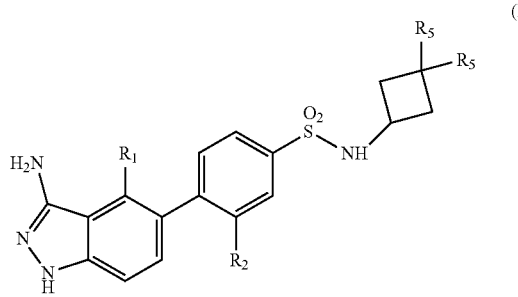

(II-1)

wherein $R_1$ and $R_2$ are as defined herein in relation to a compound of formula (I), and
each $R_5$ is independently selected from hydroxyl, haloC$_1$-C$_3$alkyl, halogen, C$_1$-C$_2$alkyl.

In another embodiment, the invention relates to a compound of formula (III) in free form or in pharmaceutically acceptable salt form

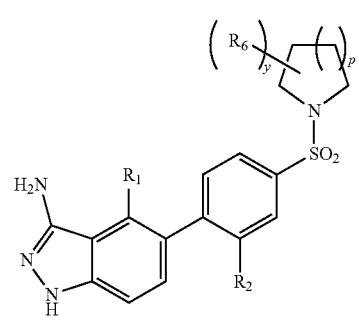

(III)

wherein
$R_1$ and $R_2$ are as defined herein in relation to a compound of formula (I),
$R_6$ is independently selected from halogen, hydroxyC$_1$-C$_3$alkyl, C(O)NH$_2$, hydroxyl, C$_1$-C$_3$alkyl, cyano, haloC$_1$-C$_3$alkyl;
p is 0, 1 or 2 and
y is 1, 2 or 3.

In another embodiment, the invention relates to a compound of formula (III-1) in free form or in pharmaceutically acceptable salt form

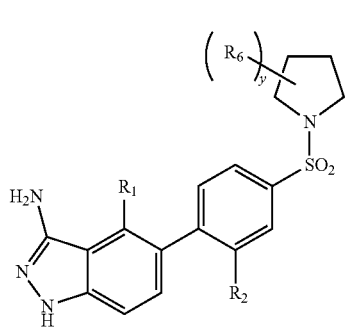

(III-1)

wherein
$R_1$ and $R_2$ are as defined herein in relation to a compound of formula (I),
$R_6$ is independently selected from halogen, hydroxyC$_1$-C$_3$alkyl, C$_1$-C$_3$alkyl, hydroxyl; and
y is 1, 2, or 3.

Various enumerated embodiments of the invention are described herein. It will be recognized that features specified in each embodiment may be combined with other specified features to provide further embodiments of the present invention.

Embodiment 1

A compound of formula (I) in free form or in pharmaceutically acceptable salt form (I)

[Structure of formula (I): 1H-indazole with 3-H₂N, 4-R₁, 5-(phenyl substituted with (R₂)n and SO₂NR₃R₄)]

wherein,

R₁ is selected from $C_1$-$C_3$alkyl, halogen and $C_1$-$C_3$alkoxy;

R₂ is independently selected from $C_1$-$C_3$alkyl and halogen;

n is 1 or 2;

R₃ is selected from H and $C_1$-$C_3$alkyl, and

R₄ is selected from a $C_4$-$C_6$cycloalkyl optionally substituted once or more than once with R₅; a 5- or 6-membered heterocyclic non-aromatic ring comprising at least one heteroatom selected from N, O or S, optionally substituted once or more than once independently with hydroxyl, $C_1$-$C_3$alkyl, $C_1$-$C_3$alkoxy; wherein R₄ is not 4-hydroxycyclohexyl or tetrahydrofuran.

or

R₃ and R₄ together with the N atom to which they are attached form a 4-, 5- or 6-membered heterocyclic non-aromatic ring optionally comprising one additional heteroatom selected from N, O or S, said ring being substituted once or more than once with R₆;

R₅ is independently selected from hydroxyl, halo$C_1$-$C_3$alkyl, halogen, $C_1$-$C_2$alkyl, phenyl, benzyl, $C_3$-$C_6$cycloalkyl, cyano;

R₆ is independently selected from halogen, hydroxy$C_1$-$C_3$alkyl, $C(O)NH_2$, hydroxyl, $C_1$-$C_3$alkyl, cyano, halo$C_1$-$C_3$alkyl.

Embodiment 2

A compound according to embodiment 1 of formula (I-1) in free form or in pharmaceutically acceptable salt form (I-1)

[Structure of formula (I-1)]

Embodiment 3

A compound according to embodiment 1 or 2 of formula (II) in free form or in pharmaceutically acceptable salt form (II)

[Structure of formula (II)]

wherein m is 0, 1, or 2 and x is 1 or 2.

Embodiment 4

A compound according to any of embodiments 1 to 3 in free form or in pharmaceutically acceptable salt form, wherein R₅ is independently selected from hydroxyl, halo$C_1$-$C_3$alkyl, halogen, $C_1$-$C_2$alkyl.

Embodiment 5

A compound according to any one of embodiments 3 or 4 in free form or in pharmaceutically acceptable salt form, wherein m is 0 or 1.

Embodiment 6

A compound according to any one of embodiments 3 to 5 in free form or in pharmaceutically acceptable salt form, wherein x is 1.

Embodiment 7

A compound according to any one of embodiments 3 to 5 in free form or in pharmaceutically acceptable salt form, wherein x is 2.

Embodiment 8

A compound according to any of embodiments 1 to 7 in free form or in pharmaceutically acceptable salt form, wherein R₃ is H.

Embodiment 9

A compound according to any of embodiments 1 to 7 in free form or in pharmaceutically acceptable salt form, wherein R₃ is methyl.

Embodiment 10

A compound according to embodiment 1 of formula (III) in free form or in pharmaceutically acceptable salt form, (III)

[Structure of formula (III)]

wherein p is 0, 1 or 2 and y is 1, 2 or 3.

Embodiment 11

A compound according to embodiment 10, in free form or in pharmaceutically acceptable sale form, wherein p is 0.

Embodiment 12

A compound according to embodiment 10, in free form or in pharmaceutically acceptable sale form, wherein p is 1.

Embodiment 13

A compound according to embodiment 10, in free form or in pharmaceutically acceptable sale form, wherein p is 2.

Embodiment 14

A compound according to any of embodiments 10 to 13, in free form or in pharmaceutically acceptable sale form, wherein y is 1.

Embodiment 15

A compound according to any of embodiments 10 to 13, in free form or in pharmaceutically acceptable sale form, wherein y is 2.

Embodiment 16

A compound according to any of embodiments 10 to 13, in free form or in pharmaceutically acceptable sale form, wherein y is 3.

Embodiment 17

A compound according to any of embodiments, 1, 2, and 10 to 16, in free form or in pharmaceutically acceptable salt form, wherein $R_6$ is independently selected from halogen, hydroxyC$_1$-C$_3$alkyl, hydroxyl, C$_1$-C$_3$alkyl.

Embodiment 18

A compound according to any of the preceding embodiments in free form or in pharmaceutically acceptable salt form, wherein $R_1$ is methyl.

Embodiment 19

A compound according to any of embodiments 1 to 17 in free form or in pharmaceutically acceptable salt form, wherein $R_1$ is chloro.

Embodiment 20

A compound according to any of embodiments 1 to 17 in free form or in pharmaceutically acceptable salt form, wherein $R_1$ is methoxy.

Embodiment 21

A compound according to any of embodiments 1 to 17 in free form or in pharmaceutically acceptable salt form, wherein $R_1$ is fluoro.

Embodiment 22

A compound according to any of embodiments 1 to 21 in free form or in pharmaceutically acceptable salt form, wherein $R_2$ is methyl.

Embodiment 23

A compound according to any of embodiments 1 to 21 in free form or in pharmaceutically acceptable salt form, wherein $R_2$ is chloro.

Embodiment 24

A compound according to embodiment 1 in free form or in pharmaceutically acceptable salt form, which is selected from 5-(2-chloro-4-((3,3-dimethylazetidin-1-yl)sulfonyl)phenyl)-4-methyl-1H-indazol-3-amine;
1-((4-(3-amino-4-methyl-1H-indazol-5-yl)-3-chlorophenyl)sulfonyl)pyrrolidin-3-ol;
1-((4-(3-amino-4-methyl-1H-indazol-5-yl)-3-fluorophenyl)sulfonyl)pyrrolidin-3-ol;
1-((4-(3-amino-4-methyl-1H-indazol-5-yl)-3-methylphenyl)sulfonyl)pyrrolidin-3-ol;
1-((4-(3-amino-4-chloro-1H-indazol-5-yl)-3-fluorophenyl)sulfonyl)pyrrolidin-3-ol;
1-((4-(3-amino-4-chloro-1H-indazol-5-yl)-3-methylphenyl)sulfonyl)pyrrolidin-3-ol;
1-((4-(3-amino-4-chloro-1H-indazol-5-yl)-3-chlorophenyl)sulfonyl)pyrrolidin-3-ol;
4-(3-amino-4-methyl-1H-indazol-5-yl)-N-(3-hydroxycyclobutyl)-3-methylbenzenesulfonamide;
1-((4-(3-amino-4-methyl-1H-indazol-5-yl)-3-methylphenyl)sulfonyl)azetidin-2-yl)methanol;
1-((4-(3-amino-4-methyl-1H-indazol-5-yl)-3-methylphenyl)sulfonyl)azetidin-3-ol;
1-((4-(3-amino-4-methyl-1H-indazol-5-yl)-3-methylphenyl)sulfonyl)-3-methylazetidin-3-ol;
1-((4-(3-amino-4-methyl-1H-indazol-5-yl)-3-methylphenyl)sulfonyl)piperidin-4-ol;
4-(3-amino-4-methyl-1H-indazol-5-yl)-N-(2-hydroxycyclopentyl)-3-methylbenzenesulfonamide;
4-(3-amino-4-methyl-1H-indazol-5-yl)-N-(2-hydroxycyclohexyl)-3-methylbenzenesulfonamide;
1-((4-(3-amino-4-methyl-1H-indazol-5-yl)-3-methylphenyl)sulfonyl)pyrrolidin-2-yl)methanol;
4-(3-amino-4-methyl-1H-indazol-5-yl)-3-methyl-N-(tetrahydro-2H-pyran-4-yl)benzenesulfonamide;
1-((4-(3-amino-4-methyl-1H-indazol-5-yl)-3-methylphenyl)sulfonyl)azetidine-3-carbonitrile;
1-((4-(3-amino-4-methyl-1H-indazol-5-yl)-3-methylphenyl)sulfonyl)piperidine-4-carbonitrile;
4-(3-amino-4-methyl-1H-indazol-5-yl)-N-(3,3-difluorocyclobutyl)-3-methylbenzenesulfonamide;
4-(3-amino-4-methyl-1H-indazol-5-yl)-N-(3-hydroxycyclohexyl)-3-methylbenzenesulfonamide;
4-(3-amino-4-methyl-1H-indazol-5-yl)-N-(3-cyanocyclohexyl)-3-methylbenzenesulfonamide;
4-(3-amino-4-methyl-1H-indazol-5-yl)-N-(4-cyanocyclohexyl)-3-methylbenzenesulfonamide;
1-((4-(3-amino-4-chloro-1H-indazol-5-yl)-3-methylphenyl)sulfonyl)pyrrolidin-2-yl)methanol;
4-(3-amino-4-chloro-1H-indazol-5-yl)-N-(2-hydroxycyclopentyl)-3-methylbenzenesulfonamide;
4-(3-amino-4-chloro-1H-indazol-5-yl)-N-(3-hydroxycyclobutyl)-3-methylbenzenesulfonamide;

4-(3-amino-4-methyl-1H-indazol-5-yl)-N-(3-hydroxy-3-(trifluoromethyl)cyclobutyl)-3-methylbenzenesulfonamide;
1-((4-(3-amino-4-methyl-1H-indazol-5-yl)-3-methylphenyl)sulfonyl)-4,4-difluoropyrrolidin-2-yl)methanol;
1-((4-(3-amino-4-methyl-1H-indazol-5-yl)-3-methylphenyl)sulfonyl)-4-fluoro-2,5-dihydro-1H-pyrrol-2-yl)methanol;
4-(3-amino-4-methyl-1H-indazol-5-yl)-3-chloro-N-(3-hydroxycyclobutyl)benzenesulfonamide;
4-(3-amino-4-methyl-1H-indazol-5-yl)-N-(3-hydroxycyclopentyl)-3-methylbenzenesulfonamide;
4-(3-amino-4-methyl-1H-indazol-5-yl)-N-(3-hydroxy-1-methylcyclobutyl)-3-methylbenzenesulfonamide;
4-(3-amino-4-chloro-1H-indazol-5-yl)-N-(3-hydroxy-3-(trifluoromethyl)cyclobutyl)-3-methylbenzenesulfonamide;
4-(3-amino-4-methyl-1H-indazol-5-yl)-N-(4,4-difluorocyclohexyl)-3-methylbenzenesulfonamide;
1-((4-(3-amino-4-methyl-1H-indazol-5-yl)-3-chlorophenyl)sulfonyl)pyrrolidin-2-yl)methanol;
4-(3-amino-4-methyl-1H-indazol-5-yl)-3-chloro-N-(2-hydroxycyclopentyl)benzenesulfonamide;
4-(3-amino-4-methyl-1H-indazol-5-yl)-N-(3-hydroxy-3-methylcyclobutyl)-3-methylbenzenesulfonamide;
1-((4-(3-amino-4-methoxy-1H-indazol-5-yl)-3-fluorophenyl)sulfonyl)-4,4-difluoropyrrolidin-2-yl)methanol;
1-((4-(3-amino-4-methyl-1H-indazol-5-yl)-3-fluorophenyl)sulfonyl)-4,4-difluoropyrrolidin-2-yl)methanol;
4-(3-amino-4-methyl-1H-indazol-5-yl)-N-(4,4-difluorocyclohexyl)-3-methylbenzenesulfonamide;
1-((4-(3-amino-4-fluoro-1H-indazol-5-yl)-3-methylphenyl)sulfonyl)-4,4-difluoropyrrolidin-2-yl)methanol;
4-(3-amino-4-methyl-1H-indazol-5-yl)-N-(4-hydroxytetrahydro-2H-pyran-3-yl)-3-methylbenzenesulfonamide;
1-((4-(3-amino-4-fluoro-1H-indazol-5-yl)-3-chlorophenyl)sulfonyl)-4,4-difluoropyrrolidin-2-yl)methanol;
1-((4-(3-amino-4-chloro-1H-indazol-5-yl)-3-fluorophenyl)sulfonyl)-4,4-difluoropyrrolidin-2-yl)methanol;
4-(3-amino-4-methyl-1H-indazol-5-yl)-N-(2-hydroxycyclopentyl)-3-methylbenzenesulfonamide;
4-(3-amino-4-methyl-1H-indazol-5-yl)-N-(3-ethyl-3-hydroxycyclobutyl)-3-methylbenzenesulfonamide;
4-(3-amino-4-methyl-1H-indazol-5-yl)-N-(3-cyclopropyl-3-hydroxycyclobutyl)-3-methylbenzenesulfonamide;
4-(3-amino-4-methyl-1H-indazol-5-yl)-N-(3-benzyl-3-hydroxycyclobutyl)-3-methylbenzenesulfonamide;
4-(3-amino-4-methyl-1H-indazol-5-yl)-N-(3-hydroxy-3-phenylcyclobutyl)-3-methylbenzenesulfonamide;
1-((4-(3-amino-4-chloro-1H-indazol-5-yl)-3-chlorophenyl)sulfonyl)-4,4-difluoropyrrolidin-2-yl)methanol;
1-((4-(3-amino-4-chloro-1H-indazol-5-yl)-3-methylphenyl)sulfonyl)-4,4-difluoropyrrolidin-2-yl)methanol;
4-(3-amino-4-methyl-1H-indazol-5-yl)-3-chloro-N-(3-hydroxy-3-(trifluoromethyl)cyclobutyl)benzenesulfonamide;
1-((4-(3-amino-4-methyl-1H-indazol-5-yl)-3-chlorophenyl)sulfonyl)-4,4-difluoropyrrolidin-2-yl)methanol;
1-((4-(3-amino-4-methyl-1H-indazol-5-yl)-3-methylphenyl)sulfonyl)-3-methylpyrrolidin-3-ol;
4-(3-amino-4-methyl-1H-indazol-5-yl)-N-(2-hydroxy-2-methylcyclopentyl)-3-methylbenzenesulfonamide;
1-(1-((4-(3-amino-4-methyl-1H-indazol-5-yl)-3-methylphenyl)sulfonyl)pyrrolidin-2-yl)ethan-1-ol;
1-((4-(3-amino-4-fluoro-1H-indazol-5-yl)-3-fluorophenyl)sulfonyl)-4,4-difluoropyrrolidin-2-yl)methanol;
1-((4-(3-amino-4-methyl-1H-indazol-5-yl)-3-methylphenyl)sulfonyl)-3-(trifluoromethyl) pyrrolidin-3-ol;
4-(3-amino-4-methyl-1H-indazol-5-yl)-N-(3,3-difluorocyclobutyl)-N,3-dimethylbenzenesulfonamide;
4-(3-amino-4-chloro-1H-indazol-5-yl)-3-chloro-N-(3-hydroxy-3-(trifluoromethyl)cyclobutyl)benzenesulfonamide;
4-(3-amino-4-methoxy-1H-indazol-5-yl)-3-chloro-N-(3-hydroxy-3-(trifluoromethyl)cyclobutyl)benzenesulfonamide;
4-(3-amino-4-chloro-1H-indazol-5-yl)-N-(3,3-difluorocyclobutyl)-3-methylbenzenesulfonamide;
4-(3-amino-4-chloro-1H-indazol-5-yl)-3-chloro-N-(3,3-difluorocyclobutyl)benzenesulfonamide;
4-(3-amino-4-methyl-1H-indazol-5-yl)-3-chloro-N-(3,3-difluorocyclobutyl)benzenesulfonamide;
4-(3-amino-4-chloro-1H-indazol-5-yl)-3-chloro-N-(2-hydroxycyclopentyl)benzenesulfonamide;
4-(3-amino-4-methoxy-1H-indazol-5-yl)-N-(3-hydroxy-3-(trifluoromethyl)cyclobutyl)-3-methylbenzenesulfonamide;
4-(3-amino-4-fluoro-1H-indazol-5-yl)-N-(3-hydroxy-3-(trifluoromethyl)cyclobutyl)-3-methylbenzenesulfonamide;
4-(3-amino-4-fluoro-1H-indazol-5-yl)-3-chloro-N-(3-hydroxy-3-(trifluoromethyl)cyclobutyl)benzenesulfonamide;
4-(3-amino-4-methoxy-1H-indazol-5-yl)-N-(2-hydroxycyclopentyl)-3-methylbenzenesulfonamide;
4-(3-amino-4-methoxy-1H-indazol-5-yl)-3-chloro-N-(2-hydroxycyclopentyl)benzenesulfonamide;
4-(3-amino-4-fluoro-1H-indazol-5-yl)-N-(2-hydroxycyclopentyl)-3-methylbenzenesulfonamide;
4-(3-amino-4-fluoro-1H-indazol-5-yl)-3-chloro-N-(2-hydroxycyclopentyl)benzenesulfonamide;
5-(4-((3,3-difluoropyrrolidin-1-yl)sulfonyl)-2-methylphenyl)-4-methyl-1H-indazol-3-amine;
5-(4-((3,3-difluoroazetidin-1-yl)sulfonyl)-2-methylphenyl)-4-methyl-1H-indazol-3-amine;
5-(4-((3,3-difluoropiperidin-1-yl)sulfonyl)-2-methylphenyl)-4-methyl-1H-indazol-3-amine
5-(4-((4,4-difluoropiperidin-1-yl)sulfonyl)-2-methylphenyl)-4-methyl-1H-indazol-3-amine;
1-((4-(3-amino-4-methyl-1H-indazol-5-yl)-3-methylphenyl)sulfonyl)-4,4-difluoropyrrolidine-2-carboxamide;
Meso-5-(4-((3,4-difluoropyrrolidin-1-yl)sulfonyl)-2-methylphenyl)-4-methyl-1H-indazol-3-amine;
4-(3-amino-4-methyl-1H-indazol-5-yl)-N-(3-hydroxy-3-(trifluoromethyl)cyclobutyl)-N,3-dimethylbenzenesulfonamide;
4-(3-amino-4-methyl-1H-indazol-5-yl)-N-(2-hydroxycyclopentyl)-N,3-dimethylbenzenesulfonamide;
1-((4-(3-amino-4-methoxy-1H-indazol-5-yl)-3-methylphenyl)sulfonyl)-4,4-difluoropyrrolidin-2-yl)methanol;
1-((4-(3-amino-4-methoxy-1H-indazol-5-yl)-3-chlorophenyl)sulfonyl)-4,4-difluoropyrrolidin-2-yl)methanol;
1-((4-(3-amino-4-methyl-1H-indazol-5-yl)-3-methylphenyl)sulfonyl)-4-fluoropyrrolidin-2-yl)methanol;
1-((4-(3-amino-4-methyl-1H-indazol-5-yl)-3,5-difluorophenyl)sulfonyl)-4,4-difluoropyrrolidin-2-yl)methanol;
1-((4-(3-amino-4-methyl-1H-indazol-5-yl)-2-fluorophenyl)sulfonyl)-4,4-difluoropyrrolidin-2-yl)methanol; and
1-((4-(3-amino-4-methyl-1H-indazol-5-yl)-2-methylphenyl)sulfonyl)-4,4-difluoropyrrolidin-2-yl)methanol.

Embodiment 25

A compound according to embodiment 1 in free form or in pharmaceutically acceptable salt form, which is selected from (R)-1-((4-(3-amino-4-methyl-1H-indazol-5-yl)-3-chlorophenyl)sulfonyl)pyrrolidin-3-ol;
(R)-1-((4-(3-amino-4-methyl-1H-indazol-5-yl)-3-methylphenyl)sulfonyl)pyrrolidin-3-ol;
(S)-1-((4-(3-amino-4-methyl-1H-indazol-5-yl)-3-methylphenyl)sulfonyl)pyrrolidin-3-ol;
(R)-1-((4-(3-amino-4-chloro-1H-indazol-5-yl)-3-fluorophenyl)sulfonyl)pyrrolidin-3-ol;
(R)-1-((4-(3-amino-4-chloro-1H-indazol-5-yl)-3-methylphenyl)sulfonyl)pyrrolidin-3-ol;
(R)-1-((4-(3-amino-4-chloro-1H-indazol-5-yl)-3-chlorophenyl)sulfonyl)pyrrolidin-3-ol;
4-(3-amino-4-methyl-1H-indazol-5-yl)-N-((1r,3r)-3-hydroxycyclobutyl)-3-methylbenzenesulfonamide;
(S)-(1-((4-(3-amino-4-methyl-1H-indazol-5-yl)-3-methylphenyl)sulfonyl)azetidin-2-yl)methanol;
4-(3-amino-4-methyl-1H-indazol-5-yl)-N-((1s,3s)-3-hydroxycyclobutyl)-3-methylbenzenesulfonamide;
4-(3-amino-4-methyl-1H-indazol-5-yl)-N-((1R,2R)-2-hydroxycyclopentyl)-3-methylbenzenesulfonamide;
4-(3-amino-4-methyl-1H-indazol-5-yl)-N-((1R,2R)-2-hydroxycyclohexyl)-3-methylbenzenesulfonamide;
4-(3-amino-4-methyl-1H-indazol-5-yl)-N-((1R,2S)-2-hydroxycyclohexyl)-3-methylbenzenesulfonamide;
4-(3-amino-4-methyl-1H-indazol-5-yl)-N-((1R,2S)-2-hydroxycyclopentyl)-3-methylbenzenesulfonamide;
(S)-(1-((4-(3-amino-4-methyl-1H-indazol-5-yl)-3-methylphenyl)sulfonyl)pyrrolidin-2-yl)methanol;
(R)-(1-((4-(3-amino-4-methyl-1H-indazol-5-yl)-3-methylphenyl)sulfonyl)pyrrolidin-2-yl)methanol;
4-(3-amino-4-methyl-1H-indazol-5-yl)-N-((1R,3R)-3-cyanocyclohexyl)-3-methylbenzenesulfonamide;
4-(3-amino-4-methyl-1H-indazol-5-yl)-N-((1s,4s)-4-cyanocyclohexyl)-3-methylbenzenesulfonamide;
(S)-(1-((4-(3-amino-4-chloro-1H-indazol-5-yl)-3-methylphenyl)sulfonyl)pyrrolidin-2-yl)methanol;
4-(3-amino-4-chloro-1H-indazol-5-yl)-N-((1R,2S)-2-hydroxycyclopentyl)-3-methylbenzenesulfonamide;
4-(3-amino-4-chloro-1H-indazol-5-yl)-N-((1s,3s)-3-hydroxycyclobutyl)-3-methylbenzenesulfonamide;
4-(3-amino-4-methyl-1H-indazol-5-yl)-N-((1s,3s)-3-hydroxy-3-(trifluoromethyl)cyclobutyl)-3-methylbenzenesulfonamide;
(S)-(1-((4-(3-amino-4-methyl-1H-indazol-5-yl)-3-methylphenyl)sulfonyl)-4,4-difluoropyrrolidin-2-yl)methanol;
(S)-(1-((4-(3-amino-4-methyl-1H-indazol-5-yl)-3-methylphenyl)sulfonyl)-4-fluoro-2,5-dihydro-1H-pyrrol-2-yl)methanol;
4-(3-amino-4-methyl-1H-indazol-5-yl)-3-chloro-N-((1s,3s)-3-hydroxycyclobutyl)benzenesulfonamide;
4-(3-amino-4-methyl-1H-indazol-5-yl)-N-((1R,3S)-3-hydroxycyclopentyl)-3-methylbenzenesulfonamide;
4-(3-amino-4-methyl-1H-indazol-5-yl)-N-((1s,3s)-3-hydroxy-1-methylcyclobutyl)-3-methylbenzenesulfonamide;
4-(3-amino-4-chloro-1H-indazol-5-yl)-N-((1s,3s)-3-hydroxy-3-(trifluoromethyl)cyclobutyl)-3-methylbenzenesulfonamide;
(S)-(1-((4-(3-amino-4-methyl-1H-indazol-5-yl)-3-chlorophenyl)sulfonyl)pyrrolidin-2-yl)methanol;
4-(3-amino-4-methyl-1H-indazol-5-yl)-3-chloro-N-((1R,2S)-2-hydroxycyclopentyl)benzenesulfonamide;
4-(3-amino-4-methyl-1H-indazol-5-yl)-N-((1s,3s)-3-hydroxy-3-methylcyclobutyl)-3-methylbenzenesulfonamide;
(S)-(1-((4-(3-amino-4-methoxy-1H-indazol-5-yl)-3-fluorophenyl)sulfonyl)-4,4-difluoropyrrolidin-2-yl)methanol;
(S)-(1-((4-(3-amino-4-methyl-1H-indazol-5-yl)-3-fluorophenyl)sulfonyl)-4,4-difluoropyrrolidin-2-yl)methanol;
(S)-(1-((4-(3-amino-4-fluoro-1H-indazol-5-yl)-3-methylphenyl)sulfonyl)-4,4-difluoropyrrolidin-2-yl)methanol;
4-(3-amino-4-methyl-1H-indazol-5-yl)-N-((3R,4R)-4-hydroxytetrahydro-2H-pyran-3-yl)-3-methylbenzenesulfonamide;
(S)-(1-((4-(3-amino-4-fluoro-1H-indazol-5-yl)-3-chlorophenyl)sulfonyl)-4,4-difluoropyrrolidin-2-yl)methanol;
(S)-(1-((4-(3-amino-4-chloro-1H-indazol-5-yl)-3-fluorophenyl)sulfonyl)-4,4-difluoropyrrolidin-2-yl)methanol;
4-(3-amino-4-methyl-1H-indazol-5-yl)-N-((1S,2R)-2-hydroxycyclopentyl)-3-methylbenzenesulfonamide;
(S)-(1-((4-(3-amino-4-chloro-1H-indazol-5-yl)-3-chlorophenyl)sulfonyl)-4,4-difluoropyrrolidin-2-yl)methanol;
(S)-(1-((4-(3-amino-4-chloro-1H-indazol-5-yl)-3-methylphenyl)sulfonyl)-4,4-difluoropyrrolidin-2-yl)methanol;
4-(3-amino-4-methyl-1H-indazol-5-yl)-3-chloro-N-((1s,3s)-3-hydroxy-3-(trifluoromethyl)cyclobutyl)benzenesulfonamide;
(S)-(1-((4-(3-amino-4-chloro-1H-indazol-5-yl)-3-chlorophenyl)sulfonyl)-4,4-difluoropyrrolidin-2-yl)methanol;
4-(3-amino-4-methyl-1H-indazol-5-yl)-N-((1S,2S)-2-hydroxy-2-methylcyclopentyl)-3-methylbenzenesulfonamide;
4-(3-amino-4-methyl-1H-indazol-5-yl)-N-((1S,2R)-2-hydroxy-2-methylcyclopentyl)-3-methylbenzenesulfonamide;
1-((S)-1-((4-(3-amino-4-methyl-1H-indazol-5-yl)-3-methylphenyl)sulfonyl)pyrrolidin-2-yl)ethan-1-ol;
(S)-(1-((4-(3-amino-4-fluoro-1H-indazol-5-yl)-3-fluorophenyl)sulfonyl)-4,4-difluoropyrrolidin-2-yl)methanol;
4-(3-amino-4-chloro-1H-indazol-5-yl)-3-chloro-N-((1s,3s)-3-hydroxy-3-(trifluoromethyl)cyclobutyl)benzenesulfonamide;
4-(3-amino-4-methoxy-1H-indazol-5-yl)-3-chloro-N-((1s,3s)-3-hydroxy-3-(trifluoromethyl)cyclobutyl)benzenesulfonamide;
4-(3-amino-4-chloro-1H-indazol-5-yl)-3-chloro-N-((1R,2S)-2-hydroxycyclopentyl)benzenesulfonamide;
4-(3-amino-4-methoxy-1H-indazol-5-yl)-N-((1s,3s)-3-hydroxy-3-(trifluoromethyl)cyclobutyl)-3-methylbenzenesulfonamide;
4-(3-amino-4-fluoro-1H-indazol-5-yl)-N-((1s,3s)-3-hydroxy-3-(trifluoromethyl)cyclobutyl)-3-methylbenzenesulfonamide;
4-(3-amino-4-fluoro-1H-indazol-5-yl)-3-chloro-N-((1s,3s)-3-hydroxy-3-(trifluoromethyl)cyclobutyl)benzenesulfonamide;
4-(3-amino-4-methoxy-1H-indazol-5-yl)-N-((1R,2S)-2-hydroxycyclopentyl)-3-methylbenzenesulfonamide;
4-(3-amino-4-methoxy-1H-indazol-5-yl)-3-chloro-N-((1R,2S)-2-hydroxycyclopentyl)benzenesulfonamide;
4-(3-amino-4-fluoro-1H-indazol-5-yl)-N-((1R,2S)-2-hydroxycyclopentyl)-3-methylbenzenesulfonamide;
4-(3-amino-4-fluoro-1H-indazol-5-yl)-3-chloro-N-((1R,2S)-2-hydroxycyclopentyl)benzenesulfonamide;
(S)-1-((4-(3-amino-4-methyl-1H-indazol-5-yl)-3-methylphenyl)sulfonyl)-4,4-difluoropyrrolidine-2-carboxamide;
Meso-5-(4-(((3R,4S)-3,4-difluoropyrrolidin-1-yl)sulfonyl)-2-methylphenyl)-4-methyl-1H-indazol-3-amine;
4-(3-amino-4-methyl-1H-indazol-5-yl)-N-((1s,3s)-3-hydroxy-3-(trifluoromethyl)cyclobutyl)-N,3-dimethylbenzenesulfonamide;
4-(3-amino-4-methyl-1H-indazol-5-yl)-N-((1R,2S)-2-hydroxycyclopentyl)-N,3-dimethylbenzenesulfonamide;

(S)-(1-((4-(3-amino-4-methoxy-1H-indazol-5-yl)-3-methylphenyl)sulfonyl)-4,4-difluoropyrrolidin-2-yl)methanol;
(S)-(1-((4-(3-amino-4-methoxy-1H-indazol-5-yl)-3-chlorophenyl)sulfonyl)-4,4-difluoropyrrolidin-2-yl)methanol;
((2S,4R)-1-((4-(3-amino-4-methyl-1H-indazol-5-yl)-3-methylphenyl)sulfonyl)-4-fluoropyrrolidin-2-yl)methanol;
(R)-(1-((4-(3-amino-4-methyl-1H-indazol-5-yl)-3-methylphenyl)sulfonyl)-4,4-difluoropyrrolidin-2-yl)methanol;
(S)-(1-((4-(3-amino-4-methyl-1H-indazol-5-yl)-3,5-difluorophenyl)sulfonyl)-4,4-difluoropyrrolidin-2-yl)methanol;
(S)-(1-((4-(3-amino-4-methyl-1H-indazol-5-yl)-2-fluorophenyl)sulfonyl)-4,4-difluoropyrrolidin-2-yl)methanol;
(S)-(1-((4-(3-amino-4-methyl-1H-indazol-5-yl)-2-methylphenyl)sulfonyl)-4,4-difluoropyrrolidin-2-yl)methanol; and
((2S,4S)-1-((4-(3-amino-4-methyl-1H-indazol-5-yl)-3-methylphenyl)sulfonyl)-4-fluoropyrrolidin-2-yl)methanol.

Embodiment 26

A pharmaceutical composition comprising a therapeutically effective amount of a compound according to any one of the preceding embodiments in free form or in pharmaceutically acceptable salt form and one or more pharmaceutically acceptable carriers.

Embodiment 27

A combination comprising a therapeutically effective amount of a compound according to any one of embodiments 1 to 25 in free form or in pharmaceutically acceptable salt form and one or more therapeutically active agents.

Embodiment 28

A compound according to any one of embodiments 1 to 25 in free form or in pharmaceutically acceptable salt form for use as a medicament.

Embodiment 29

A compound according to any one of embodiments 1 to 25 in free form or in pharmaceutically acceptable salt form for use in the treatment of a tendon injury.

Embodiment 30

A compound for use according to embodiment 29 in free form or in pharmaceutically acceptable salt form wherein the tendon injury is a tendon partial rupture.

Embodiment 31

A compound for use according to embodiment 29 in free form or in pharmaceutically acceptable salt form wherein the tendon injury is a tendon full rupture.

Embodiment 32

A compound for use according to embodiment 29 in free form or in pharmaceutically acceptable salt form wherein the tendon injury is tendon degeneration.

Embodiment 33

A compound for use according to any of embodiments 29 to 32 in free form or in pharmaceutically acceptable salt form wherein the tendon is the Achilles tendon.

Embodiment 34

A compound for use according to any of embodiments 29 to 32 in free form or in pharmaceutically acceptable salt form wherein the tendon is a rotator cuff tendon.

Embodiment 35

A compound according to any one of embodiments 1 to 25 in free form or in pharmaceutically acceptable salt form for use in the treatment of a ligament injury.

Embodiment 36

A compound for use according to embodiment 35 in free form or in pharmaceutically acceptable salt form wherein the ligament injury is a ligament partial rupture.

Embodiment 37

A compound for use according to embodiment 35 in free form or in pharmaceutically acceptable salt form wherein the ligament injury is a ligament full rupture.

Embodiment 38

A compound for use according to embodiment 35 in free form or in pharmaceutically acceptable salt form wherein the ligament injury is ligament degeneration.

Embodiment 39

A compound for use according to any of embodiment 28 to 38, wherein the compound is 1-((4-(3-amino-4-methyl-1H-indazol-5-yl)-3-methylphenyl)sulfonyl)-4,4-difluoropyrrolidin-2-yl)methanol in free form or in pharmaceutically acceptable salt form.

Embodiment 40

A compound for use according to any of embodiment 28 to 38, wherein the compound is (S)-(1-((4-(3-amino-4-methyl-1H-indazol-5-yl)-3-methylphenyl)sulfonyl)-4,4-difluoropyrrolidin-2-yl)methanol in free form or in pharmaceutically acceptable salt form.

Embodiment 41

A compound for use according to any of embodiment 28 to 38, wherein the compound is (R)-(1-((4-(3-amino-4-methyl-1H-indazol-5-yl)-3-methylphenyl)sulfonyl)-4,4-difluoropyrrolidin-2-yl)methanol in free form or in pharmaceutically acceptable salt form.

Depending on the choice of the starting materials and procedures, the compounds can be present in the form of pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula (I), (II) or (III) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides compounds of formula (I), (II) or (III) in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}$H, $^{3}$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^{3}$H and $^{14}$C, or those into which non-radioactive isotopes, such as $^{2}$H and $^{13}$C are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I). For instance, the invention provides a co-crystal comprising a compound of formula (I) and an organic acid, such as, e.g. citric acid.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington The Science and Practice of Pharmacy, 22$^{nd}$ Ed. Pharmaceutical Press, 2013, pp. 1049-1070). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, ameliorate symptoms, alleviate conditions.

As used herein, the term "subject" refers to a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of formula (I) can be prepared according to the Schemes provided infra.

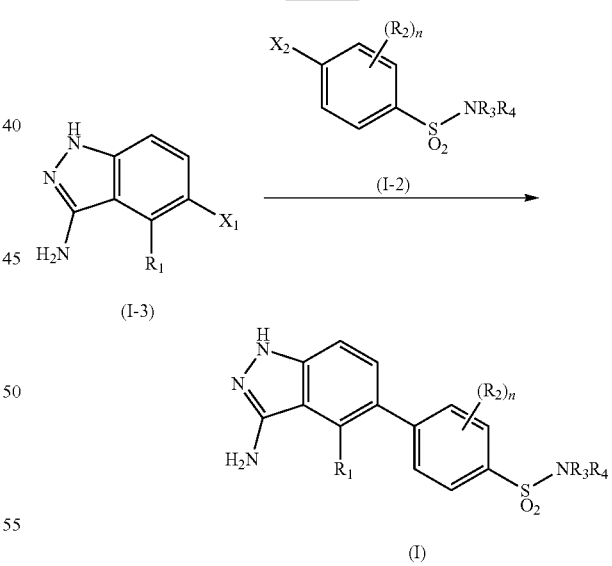

A compound of formula (I) wherein n, $R_1$, $R_2$, $R_3$ and $R_4$ are as defined herein can be prepared according to Scheme 1 by coupling a compound of formula (I-3), wherein $R_1$ is as defined herein and $X_1$ is a halogen, e.g. chloro, or a boronic acid derivative with a compound of formula (I-2), wherein n, $R_2$, $R_3$ and $R_4$ are as defined herein and $X_2$ is a halogen or a boronic acid derivative in the presence of a suitable solvent, such as e.g. dioxane, 1,2-dimethoxyethane, or acetonitrile, and a suitable catalyst, preferably a palladium-based catalyst, such as e.g. [1,1'-Bis(diphenylphosphino)

ferrocene]palladium(II) dichloride (PdCl$_2$ dppf), bis(triphenylphosphine)palladium(II) dichloride (Pd(PPh$_3$)$_2$Cl$_2$) or tetrakis(triphenylphosphine)palladium(0) (Pd(Ph$_3$)$_4$), or a suitable catalyst/ligand system such as e.g. tris(dibenzylideneacetone)dipalladium(0) (Pd$_2$(dba)$_3$) with tricyclohexylphosphine (PCy$_3$). When X$_2$ is a boronic acid derivative, such as e.g. boronic acid pinacolate, and X$_1$ is halogen, the coupling can be done in the presence of a base, such as e.g. sodium carbonate, potassium carbonate, or potassium phosphate. When X$_2$ is a halogen, such as e.g. bromide, and X$_1$ is halogen the coupling can be done in the presence of a stannane, such as e.g. hexamethylditin.

When X$_1$ is a boronic acid derivative, such as boronic acid pinacolate and X$_2$ is halogen, e.g. bromo, the coupling can be done in the presence of a suitable base, such as e.g. sodium carbonate, potassium carbonate, or potassium phosphate and a suitable catalyst, preferably a palladium-based catalyst, such as e.g. [1,1'-Bis(diphenylphosphino)ferrocene]palladium(II) dichloride (PdCl$_2$ dppf), bis(triphenylphosphine)palladium(II) dichloride (Pd(PPh$_3$)$_2$Cl$_2$) or tetrakis(triphenylphosphine)palladium(0) (Pd(Ph$_3$)$_4$), or a suitable catalyst/ligand system such as e.g. tris(dibenzylideneacetone)dipalladium(0) (Pd$_2$(dba)$_3$) with tricyclohexylphosphine (PCy$_3$).

Compounds of formula (I-3) and (I-2) can be obtained as described in the schemes and examples further below.

A compound of formula (I) wherein n, R$_1$, R$_2$, R$_3$ and R$_4$ are as defined herein can also be prepared according to Scheme 2.

Step 1: A compound of formula (I-4) wherein R$_1$ is as defined herein can be obtained by treating a compound of formula (I-6) wherein R$_1$ is as defined herein and X$_3$ is a halogen, e.g. bromo, with a boronating agent such as e.g. bis(pinacolato)diboron, in a suitable solvent, such as e.g. dioxane, in the presence of a suitable base, e.g. potassium acetate.

Step 2: A compound of formula (I-5) wherein n, R$_1$, R$_2$, R$_3$ and R$_4$ are as defined herein can be obtained by coupling a compound of formula (I-2) wherein n, R$_2$, R$_3$ and R$_4$ are as defined herein, and wherein X$_2$ is a halogen, e.g. bromo, with a compound of formula (I-4) wherein R$_1$ is as defined herein, in the presence of a suitable solvent, e.g. dioxane or 1,2-dimethoxyethane, a suitable base, e.g. potassium carbonate or cesium carbonate, and a suitable catalyst, e.g. [1,1'-Bis(diphenylphosphino)ferrocene]palladium(II) dichloride (PdCl$_2$(dppf)).

Step 3: A compound of formula (I) wherein n, R$_1$, R$_2$, R$_3$ and R$_4$ are as defined herein can be obtained by treating a compound of formula (I-5) wherein n, R$_1$, R$_2$, R$_3$ and R$_4$ are as defined herein with a hydrazine containing solution in a suitable solvent, e.g. ethanol.

Compounds of formula (I-6) wherein R$_1$ is as defined herein, and wherein X$_3$ is a halogen, e.g. bromo, can be obtained by procedures known to those skilled in the art.

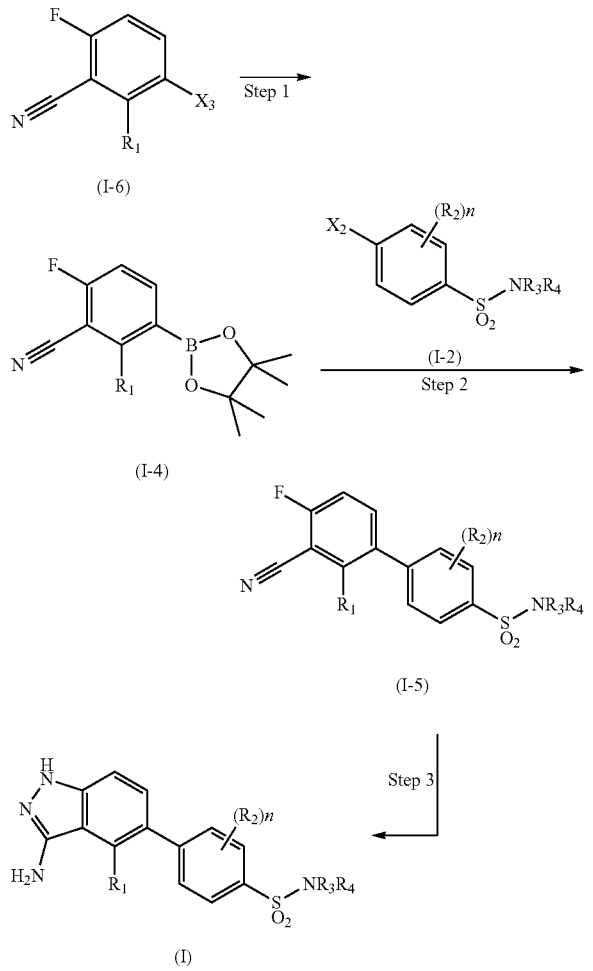

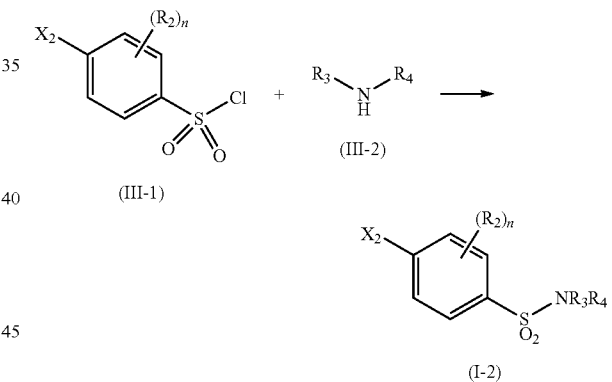

A compound of formula (I-2) wherein n, R$_2$, R$_3$ and R$_4$ are as defined herein and wherein X$_2$ is a halogen, such as e.g. bromo, can be obtained by coupling a compound of formula (III-1) wherein n and R$_2$ are as defined herein and wherein X$_2$ is a halogen, such as e.g. bromo, with a compound of formula (III-2) wherein R$_3$ and R$_4$ are as defined herein, in the presence of a suitable base, such as e.g. diisopropylethylamine or pyridine, in a suitable solvent, such as e.g. dichloromethane or pyridine.

In some cases, additional modification of the R$_3$ and R$_4$ groups can be performed following the coupling of a compound of formula (III-1) with the compound of formula (III-2). These reactions can include alcohol oxidations, carbonyl reductions, and organometallic reactions, such as Grignard additions to carbonyls.

In a further aspect, the invention relates to a process for the preparation of a compound of formula (I), in free form or in pharmaceutically acceptable salt form, comprising the steps of:

a) coupling a compound of formula (I-3) as defined herein with a compound of formula (I-2) as defined herein; and c) recovering the so obtainable compound of formula (I) in free form or in pharmaceutically acceptable salt form.

In a further aspect, the invention relates to a process for the preparation of a compound of formula (I) in free form or in pharmaceutically acceptable salt form, comprising the steps of:

a) treating a compound of formula (I-5) as defined herein with hydrazine;

d) recovering the so obtainable compound of formula (I) in free form or in pharmaceutically acceptable salt form.

Compounds of formula (I-2), (I-3), (I-4), (I-5), (I-6) as defined herein are useful in the preparation of compounds of the invention, e.g., compounds of Formula (I). Thus, in an aspect, the invention relates to a compound of formula (I-2), (I-3), (I-4), (I-5), (I-6) or salts thereof. In another aspect, the invention relates to the use of a compound of formula (I-2), (I-3), (I-4), (I-5), (I-6) or salts thereof in the manufacture of a compound of formula (I).

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as intratendinous, intraligamentous, peritendinous or periligamentous administration. In addition, the pharmaceutical compositions of the present invention can be made up in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Certain injectable compositions are aqueous isotonic solutions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient. Sucrose acetate isobutyrate (SAIB) and ethanol may be used in injectable formulations comprising the compound of the invention.

The present invention relates also, in a further particular embodiment, to sustained release formulations in the form of microparticle formulations (especially for injection) comprising as active ingredient (drug substance) a compound of the formula (I), or a pharmaceutically-acceptable salt thereof, and one or more polylactide-co-glycolide polymers (PLGAs).

The drug substance is incorporated here into a biodegradable polymer matrix consisting of 2 or more different polylactide-co-glycolide polymers (PLGAs). The PLGAs have a lactide: glycolide monomer ratio of 100:0 to 0:100, preferably to 75:20 to 20:75, more preferably 50:50.

Preferably, the PLGA or PLGAs has or have a molecular weight in the range of about 10 to 70 kDa, Preferably, the microparticles formulation contains a copolymer of DL-lactide and glycolide in a 50:50 molar ratio up to 75:25 molar ratio with an inherent viscosity ranging from 0.15 to 0.60 dL/g with an ester or acid end group, either branched or linear or combination of both copolymers plus drug substance. The drug substance incorporated into the microparticles preferably ranges from 10% to 42% (w/w). The microparticles are formulated to mean mass range in size preferably from 5 to 100 microns. The population of microparticles is formulated to be delivered through a 22 gauges or higher needles.

Additional excipients may be added to the microparticle formulations, such as, but not limited to, carboxymethylcellulose sodium, mannitol or ploxamer or combinations of two or all thereof, to achieve isotonicity and promote syringeability.

The microparticles formulation may be manufactured according to the following method steps (a) to (e):

(a) Dissolving drug substance in a poly(lactic-co-glycolic) acid copolymer organic solution comprising an organic solvent or solvent mixture to produce a drug solution;

(b) Treating the drug substance-PLGA solution to remove solvent so that it remains in an amount of 10,000 ppm or less, e.g. 100 to 5000 ppm, for example using a heating chamber; and emulsifying the resulting solution into micro-droplets by adding it into a water phase containing a proper emulsifier, such as polyvinyl alcohol, e.g. in an amount of from 0.5 to 2% by weight, such as 1% by weight;

(c) Preferably collecting the controlled- or sustained-release microparticles using a vacuumed filtration or preferably centrifugation;

(d) Preferably using a second drying step to remove residual solvents, especially freeze drying; and (e) Preferably sieving the collected controlled- or sustained-release microparticles using a sieve, e.g. a 150 micron sieve.

Particular organic solvents used for preparation of microparticles in Step (a) are, for example, dichloromethane (DCM) and ethyl acetate (EA) either alone or in combination, for example, the volume share of DCM in DCM/EA mixture may range from 5% to 50%.

The compounds of formula (I) in free form or in pharmaceutically acceptable salt form, exhibit valuable pharmacological properties, e.g. inducing tendon markers such as scleraxis, tenomodulin and/or downstream extracellular matrix (ECM) genes such as collagen type 1a2 e.g. as indicated in the in vitro and ex vivo tests as provided in the examples, and are therefore indicated for therapy or for use as research chemicals, e.g. as tool compounds.

Particularly interesting compounds of the invention have good potency in the biological assays described herein. In another aspect, they should have a favorable safety profile. In another aspect, they should possess favorable pharmacokinetic properties. Furthermore, the ideal drug candidate will be in a form that is stable, non-hygroscopic and easily formulated.

It was found that the compounds of the invention have scleraxis inducing properties. Scleraxis is a tendon cell specific transcription factor. Based on the literature, scleraxis appears to act early in the tendon cell differentiation pathway, it is a marker of both tendon cell progenitors (tendon stem cells) and of maturing tenocytes in vivo. Thus, without wishing to be bound by theory, it is thought that these properties are indicative that the compounds of the invention can be useful in treating tendon and/or ligament injuries.

Induction of scleraxis can be measured by the in vitro and ex vivo assays described in the Examples.

Preferred compounds of the invention also have tenomodulin and/or collagen type I (Col1a2) inducing properties. Tenomodulin (Tnmd) genes have been shown to be enriched in tendon cells and associated with tenogenesis while an increase in tendon collagen type I (Col1a2) is secondary to tenogenic differentiation and is thought to be necessary for proper healing. Thus, without wishing to be bound by theory, it is thought that these properties are indicative that the compounds of the invention can be useful in treating tendon and/or ligament injuries.

Induction of tenomodulin and collagen type I (Col1a2) can be measured by the ex vivo assays described in the Examples.

Having regard to their activity as scleraxis inducers, compounds of the formula (I) in free or pharmaceutically acceptable salt form, are useful in the treatment of conditions which are mediated by the activity of scleraxis proteins, such as tendon and/or ligament injuries and/or that are responsive (meaning especially in a therapeutically beneficial way) to induction of scleraxis.

Thus, the compounds of the invention may be useful in the treatment of tendon and/or ligament injury. They may be useful in the treatment of chronic tendon injury, which may lead to tendon degeneration. They may also be useful in the treatment of tendon degeneration. They may be useful in the treatment of acute tendon injury, such as tendon partial or full tear. They may be useful in the treatment of chronic ligament injury, which may lead to ligament degeneration. They may also be useful in the treatment of ligament degeneration. They may be useful in the treatment of acute ligament injury, such as ligament partial or full tear. Partial or full tear of tendons and ligaments can be determined by techniques known to the skilled person such as MRI (magnetic resonance imaging) or ultrasound.

Thus, as a further embodiment, the present invention provides the use of a compound of formula (I) or a pharmaceutically acceptable salt thereof, in therapy. In a further embodiment, the therapy is for a disease which may be treated by induction of scleraxis. In another embodiment, the disease is selected from the afore-mentioned list, suitably tendon and/or ligament injury, more suitably tendon and/or ligament partial rupture, tendon and/or ligament full rupture, tendon and/or ligament degeneration.

Tendon and ligament injuries can be identified by a skilled physician using techniques such as MRI (magnetic resonance imaging) and ultrasound.

Thus, as a further embodiment, the present invention provides a compound of formula (I) in free form or in pharmaceutically acceptable salt form for use in therapy. In a further embodiment, the therapy is for a disease which may be treated by induction of scleraxis. In another embodiment, the disease is selected from the afore-mentioned list, suitably tendon and/or ligament injury, more suitably tendon and/or ligament partial rupture, tendon and/or ligament full rupture or tendon and/or ligament degeneration.

In another embodiment, the invention provides a method of treating a disease which is treated by induction of scleraxis comprising administration of a therapeutically acceptable amount of a compound of formula (I) in free form or in pharmaceutically acceptable salt form. In a further embodiment, the disease is selected from the afore-mentioned list, suitably tendon and/or ligament injury, more suitably tendon and/or ligament partial rupture, tendon and/or ligament full rupture or tendon and/or ligament degeneration.

Thus, as a further embodiment, the present invention provides the use of a compound of formula (I) in free form or in pharmaceutically acceptable salt form, for the manufacture of a medicament. In a further embodiment, the medicament is for treatment of a disease which may be treated by induction of scleraxis. In another embodiment, the disease is selected from the afore-mentioned list, suitably tendon and/or ligament injury, more suitably tendon and/or ligament partial rupture, tendon and/or ligament full rupture or tendon and/or ligament degeneration.

In one embodiment of the present invention, there is provided 1-((4-(3-amino-4-methyl-1H-indazol-5-yl)-3-methylphenyl)sulfonyl)-4,4-difluoropyrrolidin-2-yl)methanol for use in the treatment of tendon injury.

In one embodiment of the present invention, there is provided 1-((4-(3-amino-4-methyl-1H-indazol-5-yl)-3-methylphenyl)sulfonyl)-4,4-difluoropyrrolidin-2-yl)methanol for use in the treatment of ligament injury.

In one embodiment of the present invention, there is provided 1-((4-(3-amino-4-methyl-1H-indazol-5-yl)-3-methylphenyl)sulfonyl)-4,4-difluoropyrrolidin-2-yl)methanol for use in the treatment of tendon partial rupture, tendon full rupture or tendon degeneration.

In one embodiment of the present invention, there is provided 1-((4-(3-amino-4-methyl-1H-indazol-5-yl)-3-methylphenyl)sulfonyl)-4,4-difluoropyrrolidin-2-yl)methanol for use in the treatment of ligament partial rupture, ligament full rupture or ligament degeneration.

In one embodiment of the present invention, there is provided (S)-(1-((4-(3-amino-4-methyl-1H-indazol-5-yl)-3-methylphenyl)sulfonyl)-4,4-difluoropyrrolidin-2-yl)methanol for use in the treatment of tendon injury.

In one embodiment of the present invention, there is provided (S)-(1-((4-(3-amino-4-methyl-1H-indazol-5-yl)-3-methylphenyl)sulfonyl)-4,4-difluoropyrrolidin-2-yl)methanol for use in the treatment of ligament injury.

In one embodiment of the present invention, there is provided (S)-(1-((4-(3-amino-4-methyl-1H-indazol-5-yl)-3-methylphenyl)sulfonyl)-4,4-difluoropyrrolidin-2-yl)methanol for use in the treatment of tendon partial rupture, tendon full rupture or tendon degeneration.

In one embodiment of the present invention, there is provided (S)-(1-((4-(3-amino-4-methyl-1H-indazol-5-yl)-3-methylphenyl)sulfonyl)-4,4-difluoropyrrolidin-2-yl)methanol for use in the treatment of ligament partial rupture, ligament full rupture or ligament degeneration.

In one embodiment of the present invention, there is provided (R)-(1-((4-(3-amino-4-methyl-1H-indazol-5-yl)-3-methylphenyl)sulfonyl)-4,4-difluoropyrrolidin-2-yl)methanol for use in the treatment of tendon injury.

In one embodiment of the present invention, there is provided (R)-(1-((4-(3-amino-4-methyl-1H-indazol-5-yl)-3-methylphenyl)sulfonyl)-4,4-difluoropyrrolidin-2-yl)methanol for use in the treatment of ligament injury.

In one embodiment of the present invention, there is provided (R)-(1-((4-(3-amino-4-methyl-1H-indazol-5-yl)-3-methylphenyl)sulfonyl)-4,4-difluoropyrrolidin-2-yl)methanol for use in the treatment of tendon partial rupture, tendon full rupture or tendon degeneration.

In one embodiment of the present invention, there is provided (R)-(1-((4-(3-amino-4-methyl-1H-indazol-5-yl)-3-methylphenyl)sulfonyl)-4,4-difluoropyrrolidin-2-yl)methanol for use in the treatment of ligament partial rupture, ligament full rupture or ligament degeneration.

In one embodiment of the present invention, the tendon is the Achilles tendon. In another embodiment, the tendon is a rotator cuff tendon.

In addition, the compounds shown in Table 1 as inducers of scleraxis and other tendon-related genes (tenomodulin and collagen) may also be useful in the treatment of tendon and/or ligament injuries.

Thus, in an embodiment, the invention relates to a compound of Table 1 in free form or in pharmaceutically acceptable salt form for use in the treatment of tendon and/or ligament injury.

TABLE 1

|  | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK1 (IC$_{50}$ uM) | JAK2 (IC$_{50}$ uM) | JAK3 (IC$_{50}$ uM) | TYK2 (IC$_{50}$ uM) |
|---|---|---|---|---|---|---|---|---|
| 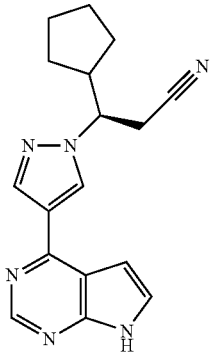 [SMILES: N#CC[C@H](C1CCCC1)n1cc(-c2ncnc3[nH]ccc23)cn1] | 0.12 | 3.13 | 0.74 | 2.64 | 1E−3 | 2E−3 | 0.2 | 6E−3 |
| 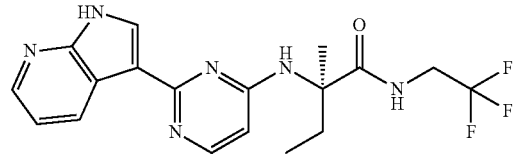 [SMILES: CC[C@@](C)(Nc1ccnc(-c2c[nH]c3ncccc23)n1)C(=O)NCC(F)(F)F] | 0.03 | 1.65 | 1.77 | 0.88 | 0.02 | 0.13 | 0.01 | 1.5 |
| 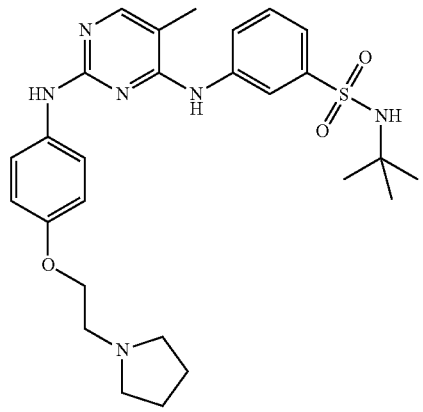 [SMILES: Cc1cnc(Nc2ccc(OCCN3CCCC3)cc2)nc1Nc1cccc(S(=O)(=O)NC(C)(C)C)c1] | 0.62 | n.d. | n.d. | n.d. | 0.02 | 8E−3 | 1.5 | 0.31 |
| 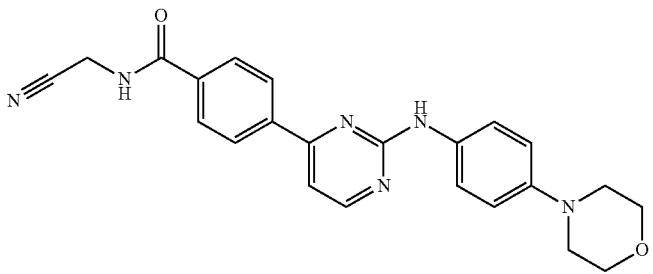 [SMILES: N#CCNC(=O)c1ccc(-c2ccnc(Nc3ccc(N4CCOCC4)cc3)n2)cc1] | 0.12 | 3.92 | 3.27 | 4.67 | 0.02 | 0.02 | 0.21 | 0.03 |

TABLE 1-continued

| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK1 (IC$_{50}$ uM) | JAK2 (IC$_{50}$ uM) | JAK3 (IC$_{50}$ uM) | TYK2 (IC$_{50}$ uM) |
|---|---|---|---|---|---|---|---|---|
| structure 1 | 8E-3 | 3.37 | 3.30 | 2.61 | 2E-4 | 7E-4 | 0.06 | 2E-3 |
| structure 2 | 2.06 | 5.65 | 3.82 | 3.97 | 4E-3 | 0.15 | 10 | 0.11 |
| structure 3 | 1.42 | 3.56 | 3.69 | 3.62 | n.d. | n.d. | n.d. | n.d. |
| structure 4 | 2.69 | 4.27 | 6.38 | 6.62 | n.d. | n.d. | n.d. | n.d. |

TABLE 1-continued
| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK1 (IC$_{50}$ uM) | JAK2 (IC$_{50}$ uM) | JAK3 (IC$_{50}$ uM) | TYK2 (IC$_{50}$ uM) |
|---|---|---|---|---|---|---|---|---|
| 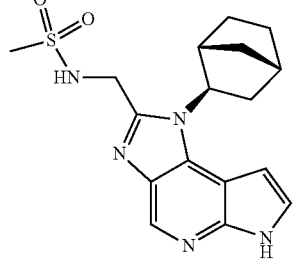 | 0.18 | 3.22 | 4.57 | 3.76 | 1E−3 | 0.19 | 0.95 | 0.14 |
| 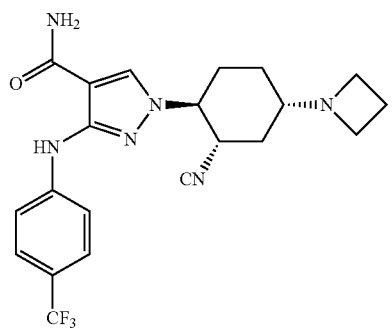 | 2.05 | 1.16 | 0.08 | 0.42 | 0.04 | 2.7 | 10 | 1.8 |
| 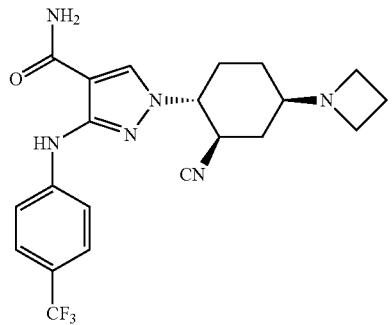 | 0.40 | 5.63 | 5.76 | 3.65 | 2E−3 | 0.24 | 10 | 0.12 |
| 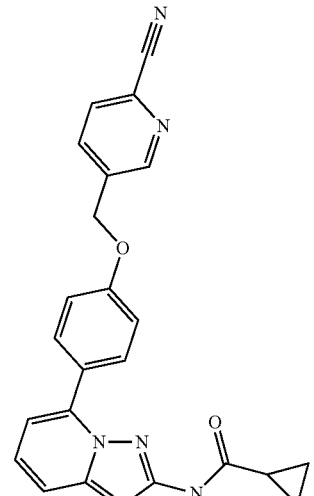 | 0.22 | 5.77 | 1.31 | 0.90 | 1E−3 | 0.03 | 0.38 | 0.11 |

TABLE 1-continued

| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK1 (IC$_{50}$ uM) | JAK2 (IC$_{50}$ uM) | JAK3 (IC$_{50}$ uM) | TYK2 (IC$_{50}$ uM) |
|---|---|---|---|---|---|---|---|---|
| [structure] | 1.24 | 0.85 | 4.83 | 0.94 | n.d. | n.d. | n.d. | n.d. |
| [structure] | 0.82 | 3.31 | 4.19 | 4.32 | n.d. | n.d. | n.d. | n.d. |
| [structure] | 0.02 | 0.36 | 5.99 | 0.40 | n.d. | n.d. | n.d. | n.d. |
| [structure] | 0.51 | 0.47 | 0.08 | 1.15 | n.d. | n.d. | n.d. | n.d. |

TABLE 1-continued

| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK1 (IC$_{50}$ uM) | JAK2 (IC$_{50}$ uM) | JAK3 (IC$_{50}$ uM) | TYK2 (IC$_{50}$ uM) |
|---|---|---|---|---|---|---|---|---|
| | 1.34 | 0.08 | 6.11 | 4.66 | n.d. | n.d. | n.d. | n.d. |
| | 4.32 | 5.34 | 6.93 | 5.01 | 0.05 | 0.46 | 9.4 | 0.78 |
| | 0.30 | 2.49 | 2.52 | 1.78 | 7E−4 | 0.004 | 0.25 | 0.03 |
| | 0.37 | 1.46 | 1.26 | 2.75 | 4E−3 | 0.03 | 0.02 | 0.23 |

TABLE 1-continued

| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK1 (IC$_{50}$ uM) | JAK2 (IC$_{50}$ uM) | JAK3 (IC$_{50}$ uM) | TYK2 (IC$_{50}$ uM) |
|---|---|---|---|---|---|---|---|---|
| 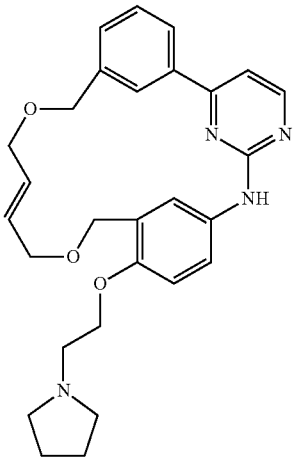 [SMILES: C1=C/COCc2cc(ccc2OCCN2CCCC2)Nc2nccc(n2)-c2cccc(c2)COC/1] | 1.06 | 3.32 | 6.71 | 3.11 | n.d. | n.d. | n.d. | n.d. | n.d.: not determined

The compounds shown in Table 1 also exhibit biochemical activity as JAK1, JAK2, JAK3 and/or TYK2 inhibitors.

The assays used to measure JAK1, JAK2, JAK3 and/or TYK2 activity are described below:

A kinase selectivity panel which measures substrate peptide phosphorylation was set-up for recombinant human Jak1 (aa 866-1154), Jak2 (aa808-1132), Jak3 (aa811-1124) and Tyk2 (aa888-1187). The technology used for the described assay is based on the separation and quantification of substrate and product in an electrical field. In the course of the kinase reaction the peptide substrate is phosphorylated by a kinase. The transfer of a phosphate residue also causes the introduction of two additional negative charges and hence to a change in the net charge of the phospho-peptide compared to the unphosphorylated peptide. Due to this difference in charge the phosphorylated und unphosphorylated peptides migrate with different velocities in an electrical field.

In the applied method, this separation takes place inside a chip that contains a complex capillary system for simultaneous analysis of 12 samples ("12-sipper chip", Caliper Technologies Corp., Mountain View, USA). In order to allow the detection and quantification of the peptides in the capillary system, the peptides carry a fluorescent label (fluorescein). With this label the peptides can be quantified by fluorescence intensity through the instruments laser and detection system (LC3000, Caliper Life Sciences).

The assays were performed in 384-well, low volume microtiter assay plates in a final reaction volume of 9 ul. Dose-response curves were generated by incubating 3 nM of each kinase together with 2 uM of a fluorescently labeled substrate peptide specific for each enzyme (Jak1 and Jak3 substrate FITC-Ahx-KKSRGDYMTMQIG-NH2, Jak2 and Tyk2 substrate 5(6)-Carboxyfluorescein-Ahx-GGEEEEY-FELVKKKK) in 50 mM Hepes pH 7.5, 0.02% Tween 20, 0.02% BSA, 1 mM DTT, 10 uM Na$_3$VO$_4$, 10 mM ß-Glycerolphosphate, specific concentrations of MgCl$_2$ (Jak1 12 mM, Jak2 and Tyk2 9 mM, Jak3 1.5 mM) and 45 uM ATP for 60 min at 30° C. in the presence or absence of compound diluted in DMSO. Kinase reaction were terminated by adding 15 ul STOP buffer (100 mM HEPES pH 7.5, 5% DMSO, 0.1% Caliper coating reagent, 10 mM EDTA, and 0.015% Brij35.

Plates with terminated kinase reactions were transferred to the Caliper LC3000 workstation (Caliper Technologies Corp., Mountain View, USA) for reading. The relative amount of phosphorylated peptide r, was calculated using the heights of the substrate peak, s, and the product peak, p: r=p/(p+s).

Having regard to their biochemical activity shown in Table 1, and without wishing to be bound by theory, it is hypothesized that inhibition of JAK1 and/or JAK2 and/or JAK3 and/or TYK2 may have a positive effect on tendon and/or ligament injury.

Therefore, in an embodiment, the invention relates to the use of a JAK1 inhibitor compound for the treatment of tendon injury.

In another embodiment, the invention relates to the use of a JAK1 inhibitor compound for the treatment of ligament injury.

In another embodiment, the invention relates to the use of a JAK2 inhibitor compound for the treatment of tendon injury.

In another embodiment, the invention relates to the use of a JAK2 inhibitor compound for the treatment of ligament injury.

In another embodiment, the invention relates to the use of a JAK3 inhibitor compound for the treatment of tendon injury.

In another embodiment, the invention relates to the use of a JAK3 inhibitor compound for the treatment of ligament injury.

In another embodiment, the invention relates to the use of a TYK2 inhibitor compound for the treatment of tendon injury.

In another embodiment, the invention relates to the use of a TYK2 inhibitor compound for the treatment of ligament injury.

In another embodiment, the invention relates to the use of a JAK1/TYK2 inhibitor compound for the treatment of tendon injury.

In another embodiment, the invention relates to the use of a JAK1/TYK2 inhibitor compound for the treatment of ligament injury.

Having regard to their known activity as JAK inhibitors, the following compounds shown in Table 2 may also be useful in the treatment of tendon and/or ligament injury. Thus, in an embodiment, the invention relates to a compound of Table 2 in free form or in pharmaceutically acceptable salt form for use in the treatment of tendon and/or ligament injury.

TABLE 2

| Compound | Structure |
| --- | --- |
| Upadacitinib | 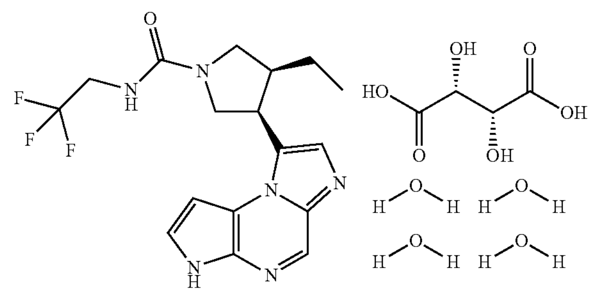 |
| ENMD-2076 ((E)-N-(5-Methyl-1H-pyrazol-3-yl)-6-(4-methylpiperazin-1-yl)-2-styrylpyrimidin-4-amine) | 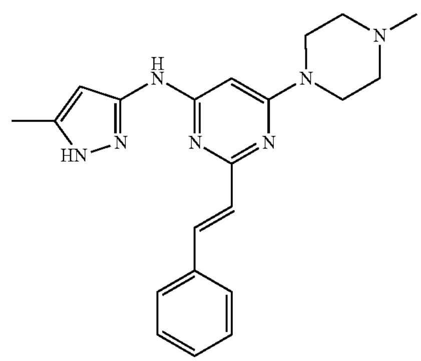 |
| JTE-052 (from company Japanese Tobacco International, LEO Pharma) | Structure unknown |
| R-333 (from Rigel) | Structure unknown |
| BMS-911543 (N,N-dicyclopropyl-4-((1,5-dimethyl-1H-pyrazol-3-yl)amino)-6-ethyl-1-methyl-1,6-dihydroimidazo[4,5-d]pyrrolo[2,3-b]pyridine-7-carboxamide) | 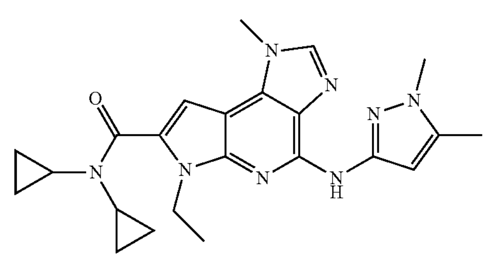 [SMILES: CCn1c(C(=O)N(C2CC2)C2CC2)cc2c3c(ncn3C)c(Nc3cc(C)n(C)n3)nc21] |
| gandotinib | 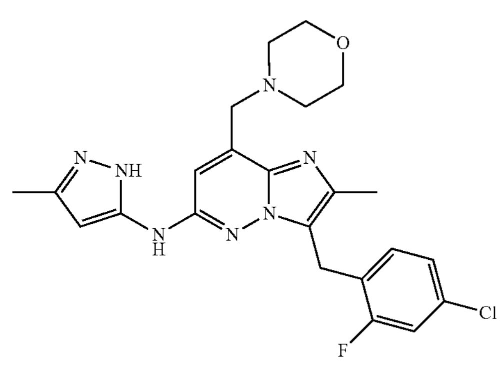 [SMILES: Cc1cc(Nc2cc(CN3CCOCC3)c3nc(C)c(Cc4ccc(Cl)cc4F)n3n2)[nH]n1] |

TABLE 2-continued

| Compound | Structure |
|---|---|
| PF-06263276 (from Pfizer) | Structure unknown |
| INCB-52793 (from Incyte) | Structure unknown |
| AC-410 ([(S)-(4-fluorophenyl)(4-((5-methyl-1H-pyrazol-3-yl)amino)quinazolin-2-yl)methanol]) | 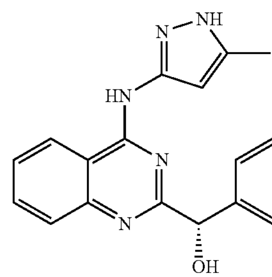 |
| cerdulatinib | 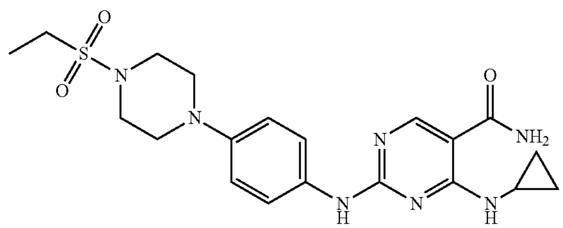 [SMILES: CCS(=O)(=O)N1CCN(c2ccc(Nc3ncc(C(N)=O)c(NC4CC4)n3)cc2)CC1] |
| TG-02, also known as SB-1317 from Tragara Pharmaceuticals | 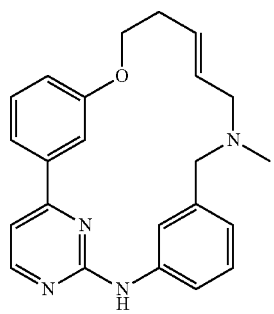 [SMILES: CN1C/C=C/CCOc2cccc(c2)-c2ccnc(n2)Nc2cccc(c2)C1] |
| LS-104 (from Aegera Therapeutics) | Structure unknown |
| peficitinib | Structure unknown |
| itacitinib | Structure unknown |
| R-348 (from Rigel) | Structure unknown |
| ganetespib | Structure unknown |
| lestaurtinib | 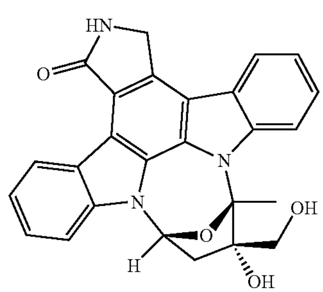 [SMILES: C[C@]12O[C@H](C[C@]1(O)CO)n1c3ccccc3c3c4c(c5c6ccccc6n2c5c31)CNC4=O] |
| PF-04965842 (from Pfizer) | 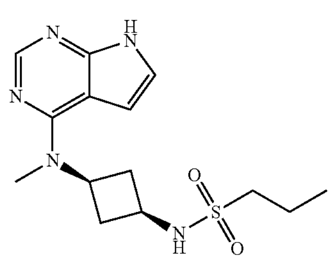 [SMILES: CCCS(=O)(=O)N[C@H]1C[C@@H](N(C)c2ncnc3[nH]ccc23)C1] |
| ASN-002 (from Asana Biosciences) | Structure unknown |
| NS-018 (from Nippon Shinyaku) | Structure unknown |

TABLE 2-continued

| Compound | Structure |
| --- | --- |
| TD-1473 (from Theravance Biopharma) | Structure unknown |
| R-548 (from Aclaris) | Structure unknown |
| CT-1578 (from Cell Therapeutics) | Structure unknown |

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) in free form or in pharmaceutically acceptable salt form and at least one other therapeutic agent as a combined preparation for simultaneous, separate or sequential use in therapy. In one embodiment, the therapy is the treatment of tendon and/or ligament injury. Products provided as a combined preparation include a composition comprising the compound of formula (I) in free form or in pharmaceutically acceptable salt form and the other therapeutic agent(s) together in the same pharmaceutical composition, or the compound of formula (I) in free form or in pharmaceutically acceptable salt form and the other therapeutic agent(s) in separate form, e.g. in the form of a kit.

In one embodiment, the invention provides a pharmaceutical composition comprising a compound of formula (I) in free form or in pharmaceutically acceptable salt form and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I) in free form or in pharmaceutically acceptable salt form. In one embodiment, the kit comprises means for separately retaining said compositions, such as a container, divided bottle, or divided foil packet.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) in free form or in pharmaceutically acceptable salt form for treating tendon and/or ligament injury, wherein the medicament is prepared for administration with another therapeutic agent. The invention also provides the use of another therapeutic agent for tendon and/or ligament injury, wherein the medicament is administered with a compound of formula (I) in free form or in pharmaceutically acceptable salt form.

The invention also provides a compound of formula (I) in free form or in pharmaceutically acceptable salt form for use in a method of treating tendon and/or ligament injury, wherein the compound of formula (I) is prepared for administration with another therapeutic agent. The invention also provides another therapeutic agent for use in a method of treating tendon and/or ligament injury, wherein the other therapeutic agent is prepared for administration with a compound of formula (I) in free form or in pharmaceutically acceptable salt form. The invention also provides a compound of formula (I) for use in a method of treating tendon and/or ligament injury, wherein the compound of formula (I) is administered with another therapeutic agent. The invention also provides another therapeutic agent for use in a method of treating tendon and/or ligament injury, wherein the other therapeutic agent is administered with a compound of formula (I) in free form or in pharmaceutically acceptable salt form.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either peritendinously or intratendinously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

EXAMPLES

Abbreviations

δ chemical shift
ACN acetonitrile
aq. aqueous
API-MS atmospheric pressure ionization mass spectroscopy
DCM methylene chloride
DIPEA diisopropylethylamine
DMSO-$d_6$ dimethylsulfoxide-d6
EtOAc ethyl acetate
EtOH ethanol
ESI-MS electron-spray ionization mass spectroscopy
FIA-MS flow injection analysis mass spectroscopy
h hour
HPLC high performance liquid chromatography
$K_2CO_3$ potassium carbonate
KOAc potassium acetate
L liter
$LiAlH_4$ lithium aluminium hydride
M molar
mg milligram
mM millimolar
MeOH methanol
min minute
mL milliliter
$MgSO_4$ magnesium sulfate
MHz megahertz
MW microwave
N normal
$Na_2SO_4$ sodium sulfate
$NaHCO_3$ sodium bicarbonate
NaOH sodium hydroxide
$NH_4Cl$ ammonium chloride
$NH_4OH$ ammonium hydroxide
NMR nuclear magnetic resonance
PCy3 tricyclohexylphosphine
$PdCl_2$(dppf) [1,1'-bis(diphenylphosphino)ferrocene]dichloropalladium(II)
ppm parts per million
RT room temperature
sat. aq. saturated aqueous
SFC supercritical fluid chromatography
THF tetrahydrofuran
$t_R$ retention time
UPLC-MS ultra high performance liquid chromatography mass spectroscopy Analytical UPLC-MS Methods
Method A
  Column: Waters Acquity HSS T3, 1.8 μm, 2.1×50 mm, oven at 60° C. Flow: 0.9 mL/min. Gradient: 10% to 90% B in 1.35 min, then 100% B for 0.30 min, then 10% B for 0.35 min; A=water+0.05% TFA (v/v), B=acetonitrile+0.035% TFA (v/v). Detection UV/VIS (DAD), ESI (+/−). Mass spectrometer range: 100-1000 Da.
Method B
  Column: Waters Acquity HSS T3, 1.8 μm, 2.1×50 mm, oven at 60° C. Flow: 0.9 mL/min. Gradient: 10% to 100% B in 1.35 min, then 100% B for 0.60 min, then 10% B for 0.05 min; A=water+0.05% TFA (v/v), B=acetonitrile+0.035% TFA (v/v). Detection UV/VIS (DAD), ESI (+/−). Mass spectrometer range: 100-1000 Da.
Method C
  Column: Waters Acquity HSS T3, 1.8 μm, 2.1×50 mm, oven at 60° C. Flow: 1.0 mL/min. Gradient: 5% to 98% B in 1.40 min, then 98% B for 0.40 min, 98% to 5% B in 0.10 min, 5% B for 0.10 min; A=water+0.05% formic acid+3.75 mM ammonium acetate, B=acetonitrile+0.04% formic acid. Detection UV/VIS (DAD), ESI (+/−). Mass spectrometer range: 100-1200 Da.

Preparative Chromatography Methods
METHOD 1: Preparative Reverse Phase HPLC
  Waters 2525 or 2545 Binary Pump
  Waters 2488 UV Detector
  Waters QDA, ZQ, or 3100 mass spectrometer
  Waters 2767 Autosampler/Fraction Collector
  Waters 515 makeup flow pump
  Column: 10 um 19×50 mm Waters Atlantis T3 5 u C18
  Flow Rate: 100 mL/min
  Run Time: 4.25 minutes
  Solvent A: H2O+0.05% TFA
  Solvent B: ACN+0.035% TFA
METHOD 2: Preparative Reverse Phase Column Chromatography (RPCC)
  Teledyne ISCO CombiFlash system
  Column: Redisep Rf Gold C18 High Performance, 15 g or 50 g pre-packed columns, 20-40 um particle size, 10 nm average pore size
  Mobile phase: Water and Acetonitrile
METHOD 3: Silica Qel Flash Column Chromatography (FCC)
  Teledyne ISCO CombiFlash system
  Column: Redisep Rf Gold normal phase silica gel, 12 g, 24 g, 40 g, or 80 g pre-packed columns, 20-40 um particle size, 6 nm average pore size
  Mobile phases: 0-20% methanol in dichloromethane; 0-100% ethyl acetate in hexanes or heptane; 0-100% (3:1 ethyl acetate/ethanol) in hexanes or heptane Intermediates Intermediate 1: 2-chloro-6-fluoro-3-(4,4,5,5-tetramethyl-1,3,2-dioxaborolan-2-yl)benzonitrile A mixture of 3-bromo-2-chloro-6-fluorobenzonitrile (500 mg, 2.133 mmol), 4,4,4',4',5,5,5',5'-octamethyl-2,2'-bi(1,3,2-dioxaborolane) (812 mg, 3.20 mmol), KOAc (523 mg, 5.33 mmol), PdCl2(dppf) (78 mg, 0.107 mmol), and dioxane (15 mL) was sparged with nitrogen and was heated at 110° C. in a sealed vial for 2 hours with stirring under microwave irradiation. The two replicate reaction mixtures were combined, filtered and concentrated and the resulting residue was used without further purification or analysis. The identity of Intermediate I was established by conversion to Intermediate 5.

Intermediate 2: 6-fluoro-2-methyl-3-(4,4,5,5-tetramethyl-1,3,2-dioxaborolan-2-yl)benzonitrile To a solution of 3-bromo-6-fluoro-2-methylbenzonitrile (CAS number 1255207-46-6) (1000 mg, 4.67 mmol) in dioxane was added 4,4,4',4',5,5,5',5'-octamethyl-2,2'-bi(1,3,2-dioxaborolane) (Sigma-Aldrich) (1780 mg, 7.01 mmol), KOAc (1146 mg, 11.68 mmol) and PdCl2(dppf) (171 mg, 0.234 mmol). The mixture was degassed by two brief vacuum/backfill cycles with nitrogen gas, and then was heated at 110° C. in a sealed vial for 2 hr with stirring under microwave irradiation. The cooled mixture was filtered through celite, and the filtrate was concentrated. The residue was taken up in ethyl acetate, and the solution was washed with water and brine. The organic layer was diluted with hexanes and then filtered through silica gel to give a yellow filtrate, which was concentrated. The residue was used without further purification or analysis. The identity of Intermediate 2 was established by conversion to Intermediate 6.

Intermediate 3: 2,6-difluoro-3-(4,4,5,5-tetramethyl-1,3,2-dioxaborolan-2-yl)benzonitrile The title compound was prepared in an analogous manner to 2-chloro-6-fluoro-3-(4,4,5,5-tetramethyl-1,3,2-dioxaborolan-2-yl)benzonitrile (Intermediate 1), using 3-bromo-2,6-difluorobenzonitrile in place of 3-bromo-2-chloro-6-fluorobenzonitrile. The crude residue was used without further purification or analysis. The identity of Intermediate 3 was established by conversion to Intermediate 7.

Intermediate 5: 4-chloro-5-(4,4,5,5-tetramethyl-1,3,2-dioxaborolan-2-yl)-1H-indazol-3-amine A solution of crude 2-chloro-6-fluoro-3-(4,4,5,5-tetramethyl-1,3,2-dioxaborolan-2-yl)benzonitrile (Intermediate 1) (1.2 g, 4.26 mmol) and hydrazine hydrate (1.07 g, 21.3 mmol) in ethanol (43 mL) was warmed at 80° C. for 1 h. The cooled reaction mixture was concentrated and the residue was purified by FCC to provide the title compound. (UPLC-MS, METHOD B) $t_R$ 1.54 min; API-MS 294.2 [M+H]$^+$.

Intermediate 6: 4-methyl-5-(4,4,5,5-tetramethyl-1,3,2-dioxaborolan-2-yl)-1H-indazol-3-amine To a solution of 6-fluoro-2-methyl-3-(4,4,5,5-tetramethyl-1,3,2-dioxaborolan-2-yl)benzonitrile (Intermediate 2) (1.0 g, 3.83 mmol) in ethanol was added hydrazine (0.601 mL, 19.15 mmol). The mixture was heated at 90° C. for 6 hrs, then the cooled reaction mixture was concentrated, and the residue was diluted with ethyl acetate and water. The organic layer was collected and washed with water and brine, then was dried over anhydrous sodium sulfate, filtered, and concentrated. The residue was purified by FCC to provide the title compound. (UPLC-MS, METHOD A) $t_R$ 1.42 min; API-MS 274.1 [M+H]$^+$.

Intermediate 7: 4-fluoro-5-(4,4,5,5-tetramethyl-1,3,2-dioxaborolan-2-yl)-1H-indazol-3-amine The title compound was prepared in an analogous manner to 4-chloro-5-(4,4,5,5-tetramethyl-1,3,2-dioxaborolan-2-yl)-1H-indazol-3-amine (Intermediate 5), using 2,6-difluoro-3-(4,4,5,5-tetramethyl-1,3,2-dioxaborolan-2-yl)benzonitrile (Intermediate 3) in place of 2-chloro-6-fluoro-3-(4,4,5,5-tetramethyl-1,3,2-dioxaborolan-2-yl)benzonitrile (Intermediate 1).

Two separate reaction runs were combined for purification by FCC to afford the title compound 4-fluoro-5-(4,4,5,5-tetramethyl-1,3,2-dioxaborolan-2-yl)-1H-indazol-3-amine, and separated by-product 4-fluoro-7-(4,4,5,5-tetramethyl-1,3,2-dioxaborolan-2-yl)-1H-indazol-3-amine. Title compound: (UPLC-MS, METHOD B) $t_R$ 1.43 min; API-MS 278.1 [M+H]$^+$.

Intermediate 8: 4-methoxy-5-(4,4,5,5-tetramethyl-1,3,2-dioxaborolan-2-yl)-1H-indazol-3-amine Step 1:
A solution of 2-fluoro-6-methoxybenzonitrile (10 g, 66.2 mmol) in trifluoromethanesulfonic acid (100 mL) at 0° C. was treated with N-bromosuccinimide (12.4 g, 69.5 mmol) and the mixture was allowed to warm to RT and was stirred for 3 days. The reaction mixture was cooled to 0° C., quenched with ice, and made basic with 6 M KOH, and the resulting solid was collected by filtration. The filter cake was dissolved in ethyl acetate and dried over sodium sulfate, and the mixture was filtered. The filtrate was concentrated to afford an approximately 1:1 mixture of 3-bromo-6-fluoro-2-methoxybenzonitrile and 3-bromo-2-fluoro-6-methoxybenzonitrile, which was used in the next step without purification or analysis.

Step 2:
A solution of the above crude mixture of 3-bromo-6-fluoro-2-methoxybenzonitrile and 3-bromo-2-fluoro-6-methoxybenzonitrile (6.7 g, 29.1 mmol combined), 4,4,4',4',5,5,5',5'-octamethyl-2,2'-bi(1,3,2-dioxaborolane) (8.14 g, 32.0 mmol), potassium acetate (6.29 g, 64.1 mmol), and Siliacate DPP-Pd (2.5 g, 29.1 mmol) in 2-propanol (291 ml) was degassed with nitrogen and was warmed at 95° C. for 24 hours. The cooled reaction mixture was filtered, then hydrazine hydrate (7.08 ml, 146 mmol) was added and the reaction mixture was warmed at 95° C. for 5 h. Celite was added to the cooled reaction mixture, and the mixture was concentrated, and the residue purified by FCC to afford the title compound 4-methoxy-5-(4,4,5,5-tetramethyl-1,3,2-dioxaborolan-2-yl)-1H-indazol-3-amine and separated by-product 4-methoxy-7-(4,4,5,5-tetramethyl-1,3,2-dioxaborolan-2-yl)-1H-indazol-3-amine. Title compound: (UPLC-MS, METHOD B) $t_R$ 1.36 min; API-MS 290.2 [M+H]$^+$.

Intermediate 9: 4-bromo-N-((1s,3s)-3-hydroxy-3-(trifluoromethyl)cyclobutyl)-3-methylbenzenesulfonamide A solution of (1s,3s)-3-amino-1-(trifluoromethyl)cyclobutanol (249 mg, 1.30 mmol) in pyridine (6.5 ml) was treated with 4-bromo-3-methylbenzene-1-sulfonyl chloride (350 mg, 1.30 mmol) and stirred at 50° C. for 3 h. The reaction mixture was concentrated under reduced pressure and the resulting product was purified by FCC to afford the title compound. (UPLC-MS, METHOD B) $t_R$ 1.67 min; API-MS 388.0 [M+H]$^+$.

Intermediate 10: ((2S,4S)-1-((4-bromo-3-methylphenyl)sulfonyl)-4-fluoropyrrolidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9) using ((2S,4S)-4-fluoropyrrolidin-2-yl)methanol to give the title compound. (UPLC-MS, METHOD B) $t_R$ 1.46 min; API-MS 352.1 [M+H]$^+$.

Intermediate 11: meso-(3R,4S)-1-((4-bromo-3-methylphenyl)sulfonyl)-3,4-difluoropyrrolidine The title compound was prepared in an analogous manner to 4-bromo-N-((1s,3s)-3-hydroxy-3-(trifluoromethyl)cyclobutyl)-3-methylbenzenesulfonamide (Intermediate 9) using meso-(3R,4S)-3,4-difluoropyrrolidine to give the title compound. (UPLC-MS, METHOD B) $t_R$ 1.91 min; API-MS 340.0 [M+H]$^+$.

Intermediate 12: (R)-(1-((4-bromo-3-methylphenyl)sulfonyl)pyrrolidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9)

using (R)-pyrrolidin-2-yl)methanol to give the title compound. (UPLC-MS, METHOD B) $t_R$ 1.65 min; API-MS 334.0 [M+H]$^+$.

Intermediate 13: (R)-1-((4-bromo-3-chlorophenyl)sulfonyl)pyrrolidin-3-ol

The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-chlorobenzene-1-sulfonyl chloride and (R)-pyrrolidin-3-ol. The reaction mixture was stirred at 0° C. for 60 min. The title compound was obtained as a yellow solid. (UPLC-MS, METHOD C) $t_R$ 0.91 min; ESI-MS 340.0/342.1 [M+H]$^+$.

Intermediate 14: (R)-1-((4-bromo-3-fluorophenyl)sulfonyl)pyrrolidin-3-ol

The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-fluorobenzene-1-sulfonyl chloride and (R)-pyrrolidin-3-ol. (UPLC-MS, METHOD B) $t_R$ 1.46 min; API-MS 324.0 [M+H]$^+$.

Intermediate 15: (R)-1-((4-bromo-3-methylphenyl)sulfonyl)pyrrolidin-3-ol

The title compound was prepared in an analogous manner to 4-bromo-N-((1s,3s)-3-hydroxy-3-(trifluoromethyl)cyclobutyl)-3-methylbenzenesulfonamide (Intermediate 9) using (R)-pyrrolidin-3-ol. (UPLC-MS, METHOD B) $t_R$ 1.42 min; API-MS 320.0 [M+H]$^+$.

Intermediate 16: 1-((S)-1-((4-bromo-3-methylphenyl)sulfonyl)pyrrolidin-2-yl)ethan-1-ol (Diastereomer Mix)

Step 1: (S)-1-((4-bromo-3-methylphenyl)sulfonyl)pyrrolidine-2-carbaldehyde

A solution of (S)-(1-((4-bromo-3-methylphenyl)sulfonyl)pyrrolidin-2-yl)methanol (Intermediate 22, vida infra) (150 mg, 0.47 mmol) in DCM (4.7 mL) was treated with Dess-Martin periodinane (298 mg, 0.70 mmol) at RT and the resulting mixture was stirred at RT for 16 h. Celite was added and the mixture was concentrated. The residue was purified by FCC to provide the title compound. (UPLC-MS, METHOD B) $t_R$ 1.66 min; API-MS 332.0 [M+H]$^+$.

Step 2: 1-((S)-1-((4-bromo-3-methylphenyl)sulfonyl)pyrrolidin-2-yl)ethanol

A solution of (S)-1-((4-bromo-3-methylphenyl)sulfonyl)pyrrolidine-2-carbaldehyde (150 mg, 0.452 mmol) in THF (Volume: 4.5 ml) at 0° C. was treated with methylmagnesium bromide solution (3.0 M, 181 µl, 0.542 mmol) and was stirred at RT for 3 h. The reaction mixture was quenched with sat. aq. ammonium chloride, diluted with DCM and passed through a phase separator. The DCM layer was concentrated and purified by FCC to afford the title compound as a mixture of diastereomers. (UPLC-MS, METHOD B) $t_R$ 1.68 min; API-MS 348.0 [M+H]$^+$.

Intermediate 17: (S)-(1-((4-bromo-3-chlorophenyl)sulfonyl)-4,4-difluoropyrrolidin-2-yl)methanol A solution of (S)-(4,4-difluoropyrrolidin-2-yl)methanol (120 mg, 0.69 mmol) in pyridine (3.5 ml) was treated with 4-bromo-3-chlorobenzene-1-sulfonyl chloride (200 mg, 0.69 mmol) and was stirred at RT for 20 h. The reaction mixture was concentrated and the residue was purified by FCC to afford the title compound. (UPLC-MS, METHOD B) $t_R$ 1.66 min; API-MS 390.0 [M+H]$^+$.

Intermediate 18: (S)-(1-((4-bromo-3-chlorophenyl)sulfonyl)pyrrolidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-chlorobenzene-1-sulfonyl chloride and (S)-(pyrrolidin-2-yl)methanol to give the title compound. (UPLC-MS, METHOD B) $t_R$ 1.02 min; ESI-MS 356.0 [M+H]$^+$.

Intermediate 19: (S)-(1-((4-bromo-3-fluorophenyl)sulfonyl)-4,4-difluoropyrrolidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-fluorobenzene-1-sulfonyl chloride and (S)-(4,4-difluoropyrrolidin-2-yl)methanol. (UPLC-MS, METHOD B) $t_R$ 1.85 min; API-MS 374.0 [M+H]$^+$.

Intermediate 20: (S)-(1-((4-bromo-3-methylphenyl)sulfonyl)-4,4-difluoropyrrolidin-2-yl)methanol A solution of (S)-(4,4-difluoropyrrolidin-2-yl)methanol (CAS number 771473-90-6) (258 mg, 1.48 mmol) in pyridine (7.4 ml) was treated with 4-bromo-3-methylbenzene-1-sulfonyl chloride (CAS number 77256-93-0) (400 mg, 1.48 mmol) and was stirred at RT for 16 h. The reaction mixture was concentrated and the residue was purified by FCC to afford the title compound. (UPLC-MS, METHOD B) $t_R$ 1.67 min; API-MS 370.0 [M+H]$^+$.

Intermediate 21: (S)-(1-((4-bromo-3-methylphenyl)sulfonyl)azetidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9) using (S)-azetidin-2-yl)methanol. (UPLC-MS, METHOD B) $t_R$ 1.61 min; API-MS 320.0 [M+H]$^+$.

Intermediate 22: (S)-(1-((4-bromo-3-methylphenyl)sulfonyl)pyrrolidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9) using (S)-(pyrrolidin-2-yl)methanol to give the title compound. (UPLC-MS, METHOD B) $t_R$ 1.66 min; API-MS 334.1 [M+H]$^+$.

Intermediate 23: (S)-1-((4-bromo-3-methylphenyl)sulfonyl)-4,4-difluoropyrrolidine-2-carboxamide The title compound was prepared in an analogous manner to 4-bromo-N-((1s,3s)-3-hydroxy-3-(trifluoromethyl)cyclobutyl)-3-methylbenzenesulfonamide (Intermediate 9) using (S)-4,4-difluoropyrrolidine-2-carboxamide to give the title compound. (UPLC-MS, METHOD B) $t_R$ 1.78 min; API-MS 383.0 [M+H]$^+$.

Intermediate 24: (S)-1-((4-bromo-3-methylphenyl) sulfonyl)pyrrolidin-3-ol

The title compound was prepared in an analogous manner to 4-bromo-N-((1s,3s)-3-hydroxy-3-(trifluoromethyl)cyclobutyl)-3-methylbenzenesulfonamide (Intermediate 9) using (S)-pyrrolidin-3-ol to give the title compound. (UPLC-MS, METHOD A) $t_R$ 1.41 min; API-MS 320.0 $[M+H]^+$.

Intermediate 25: 1-((4-bromo-3-chlorophenyl)sulfonyl)-3,3-dimethylazetidine

To a stirred solution of 4-bromo-3-chlorobenzene-1-sulfonyl chloride (200 mg, 0.69 mmol) in pyridine (4 mL) was added 3,3-dimethylazetidine (59 mg, 0.69 mmol) at 0° C. The reaction mixture was allowed to warm to rt and was stirred for additional 1 h. The reaction was quenched with 1N HCl and extracted with ethyl acetate. The organic layer was washed with 1N HCl and brine successively and was then dried over anhydrous sodium sulfate. The filtered organic layer was concentrated under vacuum to afford the title compound. (UPLC-MS, METHOD A) $t_R$ 1.69 min. API-MS 337.9 $[M+H]^+$.

Intermediate 26: 1-((4-bromo-3-fluorophenyl)sulfonyl)pyrrolidin-3-ol

The title compound was prepared in an analogous manner to (R)-1-((4-bromo-3-fluorophenyl)sulfonyl)pyrrolidin-3-ol (Intermediate 14). (UPLC-MS, METHOD A) $t_R$ 1.46 min; API-MS 324.0 $[M+H]^+$.

Intermediate 27: 1-((4-bromo-3-methylphenyl)sulfonyl)-3-(trifluoromethyl)pyrrolidin-3-ol The title compound was prepared in an analogous manner to 4-bromo-N-((1s,3s)-3-hydroxy-3-(trifluoromethyl)cyclobutyl)-3-methylbenzenesulfonamide (Intermediate 9) using 3-(trifluoromethyl)pyrrolidin-3-ol to give the title compound. (UPLC-MS, METHOD B) $t_R$ 1.59 min; API-MS 388.1 $[M+H]^+$.

Intermediate 28: 1-((4-bromo-3-methylphenyl)sulfonyl)-3,3-difluoroazetidine

The title compound was prepared in an analogous manner to 4-bromo-N-((1s,3s)-3-hydroxy-3-(trifluoromethyl)cyclobutyl)-3-methylbenzenesulfonamide (Intermediate 9) using 3,3-difluoroazetidine to give the title compound. (UPLC-MS, METHOD B) $t_R$ 1.98 min; API-MS 326.0 $[M+H]^+$.

Intermediate 29: 1-((4-bromo-3-methylphenyl)sulfonyl)-3,3-difluoropiperidine The title compound was prepared in an analogous manner to 4-bromo-N-((1s,3s)-3-hydroxy-3-(trifluoromethyl)cyclobutyl)-3-methylbenzenesulfonamide (Intermediate 9) using 3,3-difluoropiperidine to give the title compound. (UPLC-MS, METHOD B) $t_R$ 1.99 min; API-MS 354.1 $[M+H]^+$.

Intermediate 30: 1-((4-bromo-3-methylphenyl)sulfonyl)-3,3-difluoropyrrolidine The title compound was prepared in an analogous manner to 4-bromo-N-((1s,3s)-3-hydroxy-3-(trifluoromethyl)cyclobutyl)-3-methylbenzenesulfonamide (Intermediate 9) using 3,3-difluoropyrrolidine to give the title compound (UPLC-MS, METHOD B) $t_R$ 1.96 min; API-MS 340.0 $[M+H]^+$.

Intermediate 31: 1-((4-bromo-3-methylphenyl)sulfonyl)-3-methylazetidin-3-ol

The title compound was prepared in an analogous manner to 4-bromo-N-((1s,3s)-3-hydroxy-3-(trifluoromethyl)cyclobutyl)-3-methylbenzenesulfonamide (Intermediate 9) using 3-methylazetidin-3-ol to give the title compound. (UPLC-MS, METHOD B) $t_R$ 1.57 min; API-MS 320.0 $[M+H]^+$.

Intermediate 32: 1-((4-bromo-3-methylphenyl)sulfonyl)-3-methylpyrrolidin-3-ol

Step 1: 1-((4-bromo-3-methylphenyl)sulfonyl)pyrrolidin-3-one

The title compound was prepared in an analogous manner to 4-bromo-N-((1s,3s)-3-hydroxy-3-(trifluoromethyl)cyclobutyl)-3-methylbenzenesulfonamide (Intermediate 9) using pyrrolidin-3-one to give the title compound. (UPLC-MS, METHOD B) $t_R$ 1.65 min; API-MS 318.0 $[M+H]^+$.

Step 2: 1-((4-bromo-3-methylphenyl)sulfonyl)-3-methylpyrrolidin-3-ol

A solution of 1-((4-bromo-3-methylphenyl)sulfonyl)pyrrolidin-3-one (70 mg, 0.22 mmol) in THF (2.2 mL) at 0° C. was treated with methylmagnesium bromide solution (3.0 M, 88 μl, 0.264 mmol) and was allowed to warm to RT and was stirred for 3 h. Additional methylmagnesium bromide solution (3.0 M, 88 μl, 0.264 mmol) was added and the reaction mixture was stirred for 18 h. The reaction mixture was quenched with sat. aq. ammonium chloride, diluted with DCM and passed through a phase separator. The DCM layer was concentrated and purified by FCC to afford the title compound. (UPLC-MS, METHOD B) $t_R$ 1.59 min; API-MS 334.1 $[M+H]^+$.

Intermediate 33: 1-((4-bromo-3-methylphenyl)sulfonyl)-4,4-difluoropiperidine The title compound was prepared in an analogous manner to 4-bromo-N-((1s,3s)-3-hydroxy-3-(trifluoromethyl)cyclobutyl)-3-methylbenzenesulfonamide (Intermediate 9) using 4,4-difluoropiperidine to give the title compound. (UPLC-MS, METHOD B) $t_R$ 2.03 min; API-MS 354.1 $[M+H]^+$.

Intermediate 34: 1-((4-bromo-3-methylphenyl)sulfonyl)-4-cyanopiperidine

The title compound was prepared in an analogous manner to 4-bromo-N-((1s,3s)-3-hydroxy-3-(trifluoromethyl)cyclobutyl)-3-methylbenzenesulfonamide (Intermediate 9) using 4-cyanopiperidine to give the title compound. (UPLC-MS, METHOD B) $t_R$ 1.76 min; API-MS 343.0 $[M+H]^+$.

Intermediate 35: 1-((4-bromo-3-methylphenyl)sulfonyl)-azetidin-3-ol

The title compound was prepared in an analogous manner to 4-bromo-N-((1s,3s)-3-hydroxy-3-(trifluoromethyl)cyclobutyl)-3-methylbenzenesulfonamide (Intermediate 9) using azetidin-3-ol to give the title compound. (UPLC-MS, METHOD B) $t_R$ 1.51 min; API-MS 306.0 [M+H]$^+$.

Intermediate 36: 1-((4-bromo-3-methylphenyl)sulfonyl)azetidine-3-carbonitrile

The title compound was prepared in an analogous manner to 4-bromo-N-((1s,3s)-3-hydroxy-3-(trifluoromethyl)cyclobutyl)-3-methylbenzenesulfonamide (Intermediate 9) using azetidin-3-carbonitrile to give the title compound. (UPLC-MS, METHOD B) $t_R$ 1.65 min; API-MS 315.0 [M+H]$^+$.

Intermediate 37: 1-((4-bromo-3-methylphenyl)sulfonyl)piperidin-4-ol

The title compound was prepared in an analogous manner to 4-bromo-N-((1s,3s)-3-hydroxy-3-(trifluoromethyl)cyclobutyl)-3-methylbenzenesulfonamide (Intermediate 9) using piperidin-4-ol to give the title compound. (UPLC-MS, METHOD B) $t_R$ 1.62 min; API-MS 334.0 [M+H]$^+$.

Intermediate 38: 4-bromo-3-chloro-N-((1R,2S)-2-hydroxycyclopentyl)benzenesulfonamide The title compound was prepared in an analogous manner to (S)-(1-((4-bromo-3-chlorophenyl)sulfonyl)-4,4-difluoropyrrolidin-2-yl)methanol (Intermediate 17) using (1R,2S)-2-hydroxycyclopentylamine to give the title compound. (UPLC-MS, METHOD B) $t_R$ 1.68 min; API-MS 354.0 [M+H]$^+$.

Intermediate 39: 4-bromo-3-chloro-N-((1s,3s)-3-hydroxy-3-(trifluoromethyl)cyclobutyl)benzenesulfonamide The title compound was prepared in an analogous manner to (S)-(1-((4-bromo-3-chlorophenyl)sulfonyl)-4,4-difluoropyrrolidin-2-yl)methanol (Intermediate 17) using (1s,3s)-3-amino-1-(trifluoromethyl)cyclobutanol to give the title compound. (UPLC-MS, METHOD B) $t_R$ 1.68 min; API-MS 408.0 [M+H]$^+$.

Intermediate 41: 4-bromo-3-methyl-N-((1R,2S)-2-hydroxycyclopentyl)benzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (1R,2S)-2-hydroxycyclopentylamine to give the title compound. (UPLC-MS, METHOD B) $t_R$ 1.67 min; API-MS 334.1 [M+H]$^+$.

Intermediate 43: 4-bromo-3-methyl-N-(tetrahydro-2H-pyran-4-yl)benzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using 1-aminotetrahydro-2H-pyran to give the title compound. (UPLC-MS, METHOD B) $t_R$ 1.62 min; API-MS 334.1 [M+H]$^+$.

Intermediate 44: 4-bromo-N-((1R,2R)-2-hydroxycyclohexyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using—(1R,2R)-2-hydroxycyclohexylamine to give the title compound (UPLC-MS, METHOD B) $t_R$ 1.66 min; API-MS 348.1 [M+H]$^+$.

Intermediate 45: 4-bromo-N-((1R,2R)-2-hydroxycyclopentyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (1R,2R)-2-hydroxycyclopentylamine to give the title compound. (UPLC-MS, METHOD B) $t_R$1.56 min; API-MS 334.0 [M+H]$^+$.

Intermediate 46: 4-bromo-N-((1R,2S)-2-hydroxycyclohexyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (1R,2S)-2-hydroxycyclohexylamine to give the title compound (UPLC-MS, METHOD B) $t_R$ 1.68 min; API-MS 348.1 [M+H]$^+$.

Intermediate 47: 4-bromo-N-((1R,2S)-2-hydroxycyclopentyl)-N,3-dimethylbenzenesulfonamide Step 1: (1S,2R)-2-(methylamino)cyclopentanol A solution of (1S,2R)-2-aminocyclopentanol (200 mg, 1.45 mmol) and DIPEA (0.76 mL, 4.4 mmol) in THF (14.5 mL) was treated with methyl chloroformate (225 µl, 2.91 mmol) and the solution was stirred at 60° C. for 16 h. The reaction mixture was cooled to RT and was treated with LiAlH$_4$ solution (1.0 M, 7.3 ml, 7.3 mmol) and was heated at 60° C. for 4 h. The cooled reaction mixture was treated with water, 1 N NaOH, and water, and the mixture was filtered. The resulting solution was concentrated, and the residue was used without further purification. (UPLC-MS, METHOD B) $t_R$ 0.39 min; API-MS 116.2 [M+H]$^+$.

Step 2: 4-bromo-N-((1R,2S)-2-hydroxycyclopentyl)-N,3-dimethylbenzenesulfonamide

A solution of crude (1S,2R)-2-(methylamino)cyclopentanol (167 mg, 1.45 mmol) in pyridine (7.3 mL) was treated with 4-bromo-3-methylbenzene-1-sulfonyl chloride (390 mg, 1.45 mmol) and the mixture was stirred at 60° C. for 18 h. The cooled reaction mixture was concentrated and the residue was purified by FCC to afford the title compound. (UPLC-MS, METHOD B) $t_R$ 1.95 min; API-MS 348.1 [M+H]$^+$.

Intermediate 48: 4-bromo-N-((1R,3R)-3-cyanocyclohexyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-methylbenzene-1-sulfonyl chloride and (1R,3R)-3-aminocyclohexane-1-carbonitrile to give the title compound (UPLC-MS, METHOD B) $t_R$ 1.64 min; API-MS 357.1 [M+H]$^+$.

Intermediate 49: 4-bromo-N-((1r,3r)-3-hydroxycyclobutyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (1r,3r)-3-aminocyclobutan-1-ol to give the title compound (UPLC-MS, METHOD B) $t_R$ 1.47 min; API-MS 320.0 [M+H]$^+$.

Intermediate 50: 4-bromo-N-((1R,3S)-3-hydroxycyclopentyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (1R,3S)-3-hydroxycyclopentylamine to provide the title compound. (UPLC-MS, METHOD B) $t_R$ 1.55 min; API-MS 334.0 [M+H]$^+$.

Intermediate 51: 4-bromo-N-((1S,2R)-2-hydroxycyclopentyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (1S,2R)-2-hydroxycyclopentylamine to give the title compound (UPLC-MS, METHOD B) $t_R$ 1.68 min; API-MS 334.1 [M+H]$^+$.

Intermediate 52: 4-bromo-N-((1s,3s)-3-hydroxy-1-methylcyclobutyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (1s,3s)-3-hydroxy-1-methylcyclobutylamine to give the title compound (UPLC-MS, METHOD B) $t_R$ 1.49 min; API-MS 334.0 [M+H]$^+$.

Intermediate 53: 4-bromo-N-((1s,3s)-3-hydroxy-3-methylcyclobutyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (1s,3s)-3-hydroxy-3-methylcyclobutylamine to give the title compound (UPLC-MS, METHOD B) $t_R$ 1.49 min; API-MS 356.0 [M+Na]$^+$.

Intermediate 54: 4-bromo-3-chloro-N-((1s,3s)-3-hydroxycyclobutyl)benzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-chlorobenzene-1-sulfonyl chloride and (1s,3s)-3-aminocyclobutanol to give the title compound. (UPLC-MS, METHOD B) $t_R$ 1.45 min; API-MS 340.0 [M+H]$^+$.

Intermediate 55: 4-bromo-N-((1s,3s)-3-hydroxycyclobutyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-chlorobenzene-1-sulfonyl chloride and (1s,3s)-3-aminocyclobutanol to give the title compound. (UPLC-MS, METHOD B) $t_R$ 1.46 min; API-MS 320.0 [M+H]$^+$.

Intermediate 56: 4-bromo-N-((1s,4s)-4-cyanocyclohexyl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-methylbenzene-1-sulfonyl chloride and (1s,4s)-4-aminocyclohexane-1-carbonitrile to give the title compound (UPLC-MS, METHOD B) $t_R$ 1.58 min; API-MS 357.1 [M+H]$^+$ Intermediate 57: 4-bromo-N-((3R,4R)-4-hydroxytetrahydro-2H-pyran-3-yl)-3-methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using (3R,4R)-3-aminotetrahydro-2H-pyran-4-ol to give the title compound (UPLC-MS, METHOD B) $t_R$ 1.44 min; API-MS 350.0 [M+H]$^+$.

Intermediate 58: 4-bromo-N-(3,3-difluorocyclobutyl)-3-chlorobenzenesulfonamide

The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-chlorobenzene-1-sulfonyl chloride and 1-amino-3,3-difluorocyclobutane to give the title compound. (UPLC-MS, METHOD B) $t_R$ 1.72 min; API-MS 360.0 [M+H]$^+$.

Intermediate 59: 4-bromo-N-(3,3-difluorocyclobutyl)-3-methylbenzenesulfonamide methylbenzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9) using 1-amino-3,3-difluorocyclobutane to give the title compound. (UPLC-MS, METHOD B) $t_R$ 1.60 min; API-MS 340.0 [M+H]$^+$.

Intermediate 60: 4-bromo-N-(3,3-difluorocyclobutyl)-N,3-dimethylbenzenesulfonamide A mixture of 4-bromo-N-(3,3-difluorocyclobutyl)-3-methylbenzenesulfonamide (Intermediate 80) (100 mg, 0.29 mmol), potassium carbonate (81 mg, 0.59 mmol), and DMF (4 mL) was treated with methyl iodide (0.037 mL, 0.588 mmol) and was stirred at RT for 4 h. The reaction mixture was concentrated under a stream of nitrogen overnight. The resulting residue was taken up in DCM and was filtered and purified directly by FCC to afford the title compound. (UPLC-MS, METHOD B) $t_R$ 1.71 min; API-MS 354.1 [M+H]$^+$.

Intermediate 61: 4-bromo-N-(3-cyclopropyl-3-hydroxycyclobutyl)-3-methylbenzenesulfonamide Step 1: 4-bromo-3-methyl-N-(3-oxocyclobutyl)benzenesulfonamide The title compound was prepared in an analogous manner to 4-bromo-N-((1s,3s)-3-hydroxy-3-(trifluoromethyl)cyclobutyl)-3-methylbenzenesulfonamide (Intermediate 9)

using 3-aminocyclobutanone to give the title compound. (UPLC-MS, METHOD B) $t_R$ 1.59 min; API-MS 318.0 [M+H]$^+$.

Step 2: 4-bromo-N-(3-cyclopropyl-3-hydroxycyclobutyl)-3-methylbenzenesulfonamide A solution of 4-bromo-3-methyl-N-(3-oxocyclobutyl) benzenesulfonamide (25 mg, 0.079 mmol) in 2-Me-THF (1.6 mL) at 0° C. was treated with cyclopropylmagnesium bromide solution (0.5 M, 0.31 mL, 0.157 mmol) and was stirred and allowed to slowly warm to RT over 16 h. The reaction mixture was quenched with sat. aq. NH4Cl, diluted with DCM and passed through a phase separator. The DCM layer was concentrated and was purified by FCC to afford the title compound. (UPLC-MS, METHOD B) $t_R$ 1.61 min; API-MS 382.0 [M+Na]$^+$.

Intermediate 62: 4-bromo-N-(3-ethyl-3-hydroxycyclobutyl)-3-methylbenzenesulfonamide The title compound was prepared in an analogous manner to 4-bromo-N-(3-cyclopropyl-3-hydroxycyclobutyl)-3-methylbenzenesulfonamide (Intermediate 82) using ethylmagnesium bromide in Step 2 in place of cyclopropylmagnesium bromide to give the title compound. (UPLC-MS, METHOD B) $t_R$ 1.60 min; API-MS 370.0 [M+Na]$^+$.

Intermediate 63: 4-bromo-N-((1s,3s)-3-hydroxy-3-(trifluoromethyl)cyclobutyl)-N,3-dimethylbenzenesulfonamide The title compound was prepared in an analogous manner to 4-bromo-N-((1R,2S)-2-hydroxycyclopentyl)-N,3-dimethylbenzenesulfonamide (Intermediate 47) using (1s,3s)-3-amino-1-(trifluoromethyl)cyclobutanol in place of (1S,2R)-2-aminocyclopentanol in Step 1 to give the title compound. (UPLC-MS, METHOD B) $t_R$ 1.90 min; API-MS 402.1 [M+H]$^+$.

Intermediate 64: 4-bromo-N-(3-hydroxy-3-phenylcyclobutyl)-3-methylbenzenesulfonamide The title compound was prepared in an analogous manner to 4-bromo-N-(3-cyclopropyl-3-hydroxycyclobutyl)-3-methylbenzenesulfonamide (Intermediate 61) using phenylmagnesium bromide in Step 2 in place of cyclopropylmagnesium bromide, to provide the title compound. (UPLC-MS, METHOD B) $t_R$ 1.73 min; API-MS 418.1 [M+Na]$^+$.

Intermediate 65: 4-bromo-N-(3-hydroxycyclohexyl)-3-methylbenzenesulfonamide

The title compound was prepared in an analogous manner to 4-bromo-N-((1s,3s)-3-hydroxy-3-(trifluoromethyl)cyclobutyl)-3-methylbenzenesulfonamide (Intermediate 9) using 4-bromo-3-methylbenzene-1-sulfonyl chloride and (1R,3R)-3-aminocyclohexane-1-carbonitrile to give the title compound (UPLC-MS, METHOD B) $t_R$ 1.46 min; API-MS 348.1 [M+H]$^+$.

Intermediate 66: 4-bromo-N-(4,4-difluorocyclohexyl)-3-methylbenzenesulfonamide

The title compound was prepared in an analogous manner to 4-bromo-N-((1s,3s)-3-hydroxy-3-(trifluoromethyl)cyclobutyl)-3-methylbenzenesulfonamide (Intermediate 9) using 4,4-difluorocyclohexanamine to give the title compound. (UPLC-MS, METHOD B) $t_R$ 1.58 min; API-MS 368.0 [M+H]$^+$.

Intermediate 67: (S)-(1-((4-bromo-2-methylphenyl)sulfonyl)-4,4-difluoropyrrolidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9), using 4-bromo-2-methylbenzene-1-sulfonyl chloride and (S)-4,4-(difluoropyrrolidin-2-yl)methanol to give the title compound. (UPLC-MS, METHOD B) $t_R$ 1.55 min; API-MS 370.1 [M+H]$^+$.

Intermediate 68: (S)-(1-((4-bromo-2-fluorophenyl)sulfonyl)-4,4-difluoropyrrolidin-2-yl)methanol 4-bromo-2-fluorobenzene-1-sulfonyl chloride (95 mg, 0.35 mmol) was added to a solution of (S)-(4,4-difluoropyrrolidin-2-yl)methanol hydrochloride (60 mg, 0.35 mmol) and DIEA (0.15 mL, 0.86 mmol) in THF (2 mL) at 0° C. The mixture was stirred at 0° C. for 1 hr, then was concentrated. The residue was purified by FCC to give the title compound. (UPLC-MS, METHOD B) $t_R$ 1.50 min; API-MS 374.1 [M+H]$^+$.

Intermediate 69: (S)-(1-((4-bromo-3,5-difluorophenyl)sulfonyl)-4,4-difluoropyrrolidin-2-yl)methanol The title compound was prepared in an analogous manner to (S)-(1-((4-bromo-2-fluorophenyl)sulfonyl)-4,4-difluoropyrrolidin-2-yl)methanol (Intermediate 68), using 4-bromo-3,5-difluorobenzene-1-sulfonyl chloride and (S)-4,4-(difluoropyrrolidin-2-yl)methanol to give the title compound. (UPLC-MS, METHOD B) $t_R$ 1.58 min; API-MS 392.0 [M+H]$^+$.

Intermediate 70: N-(3-benzyl-3-hydroxycyclobutyl)-4-bromo-3-methylbenzenesulfonamide The title compound was prepared in an analogous manner to 4-bromo-N-(3-cyclopropyl-3-hydroxycyclobutyl)-3-methylbenzenesulfonamide (Intermediate 61) using benzylmagnesium chloride in Step 2 in place of cyclopropylmagnesium bromide, to give the title compound. (UPLC-MS, METHOD B) $t_R$ 1.74 min; API-MS 432.1 [M+Na]$^+$.

Intermediate 71: ((2S,4R)-1-((4-bromo-3-methylphenyl)sulfonyl)-4-fluoropyrrolidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9), using ((2S,4R)-4-fluoropyrrolidin-2-yl)methanol to give the title compound. (UPLC-MS, METHOD B) $t_R$ 1.47 min; API-MS 352.1 [M+H]$^+$.

Intermediate 72: (R)-(1-((4-bromo-3-methylphenyl)sulfonyl)-4,4-difluoropyrrolidin-2-yl)methanol The title compound was prepared in an analogous manner to 4-bromo-N-((1s,3s)-3-hydroxy-3-(trifluoromethyl)cyclobutyl)-3-methylbenzenesulfonamide (Intermediate 9), using (R)-4,4-(difluoropyrrolidin-2-yl)methanol to give the title compound. (UPLC-MS, METHOD B) $t_R$ 1.56 min; API-MS 370.0 [M+H]$^+$.

Example 1: 5-(2-chloro-4-((3,3-dimethylazetidin-1-yl)sulfonyl)phenyl)-4-methyl-1H-indazol-3-amine

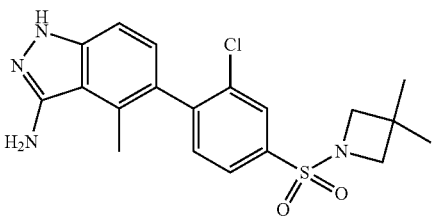 [SMILES: Cc1c(-c2ccc(S(=O)(=O)N3CC(C)(C)C3)cc2Cl)ccc2[nH]nc(N)c12]

A solution of 4-methyl-5-(4,4,5,5-tetramethyl-1,3,2-dioxaborolan-2-yl)-1H-indazol-3-amine (Intermediate 6) (20 mg, 0.073 mmol), 1-((4-bromo-3-chlorophenyl)sulfonyl)-3,3-dimethylazetidine (Intermediate 25) (25 mg, 0.073 mmol), cesium carbonate (72 mg, 0.220 mmol) and PdCl$_2$(dppf) (5.4 mg, 7.3 μmol) was evacuated by high vacuum and then purged with nitrogen gas. Degassed DME/water (4:1, 2 ml) was added to the flask, and the mixture was heated at 150° C. for 30 min under microwave irradiation. The cooled reaction mixture was filtered through celite, and then the reaction mixture was purified by RPCC (METHOD 2). (UPLC-MS, METHOD A) $t_R$ 1.52 min; API-MS 405.1 [M+H]$^+$.

Example 2: (R)-1-((4-(3-amino-4-methyl-1H-indazol-5-yl)-3-chlorophenyl)sulfonyl)pyrrolidin-3-ol

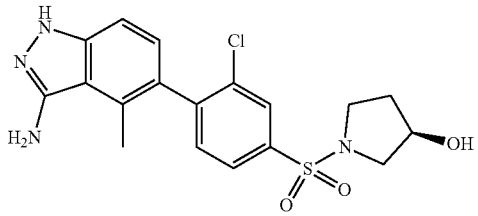 [SMILES: Cc1c(-c2ccc(S(=O)(=O)N3CC[C@@H](O)C3)cc2Cl)ccc2[nH]nc(N)c12]

The title compound was prepared in an analogous manner to Example 1, using (R)-1-((4-bromo-3-chlorophenyl)sulfonyl)pyrrolidin-3-ol (Intermediate 13) in place of 1-((4-bromo-3-chlorophenyl)sulfonyl)-3,3-dimethylazetidine (Intermediate 25). (UPLC-MS, METHOD A) $t_R$ 1.24 min; API-MS 407.05 [M+H]$^+$.

Example 3: 1-((4-(3-amino-4-methyl-1H-indazol-5-yl)-3-fluorophenyl)sulfonyl)pyrrolidin-3-ol

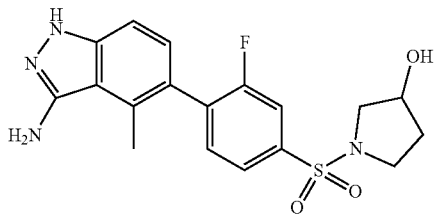 [SMILES: Cc1c(-c2ccc(S(=O)(=O)N3CCC(O)C3)cc2F)ccc2[nH]nc(N)c12]

Step 1: 2',4-difluoro-4'-((3-hydroxypyrrolidin-1-yl)sulfonyl)-2-methyl-[1,1'-biphenyl]-3-carbonitrile The title compound was prepared in an analogous manner to Example 1, using 1-((4-bromo-3-fluorophenyl)sulfonyl)pyrrolidin-3-ol (Intermediate 26) in place of 1-((4-bromo-3-chlorophenyl)sulfonyl)-3,3-dimethylazetidine (Intermediate 25), and using 6-fluoro-2-methyl-3-(4,4,5,5-tetramethyl-1,3,2-dioxaborolan-2-yl)benzonitrile (Intermediate 2) in place of 4-methyl-5-(4,4,5,5-tetramethyl-1,3,2-dioxaborolan-2-yl)-1H-indazol-3-amine (Intermediate 6). The crude reaction mixture was diluted with ethyl acetate and water and then the organic layer was washed with water and brine, dried over sodium sulfate, filtered, and the filtrate concentrated to provide the title compound, which was used without further purification or analysis. The identity of the reaction product was established by its conversion to 1-((4-(3-amino-4-methyl-1H-indazol-5-yl)-3-fluorophenyl)sulfonyl)pyrrolidin-3-ol in Step 2.

Step 2: 1-((4-(3-amino-4-methyl-1H-indazol-5-yl)-3-fluorophenyl)sulfonyl)pyrrolidin-3-ol To a solution of 2',4-difluoro-4'-((3-hydroxypyrrolidin-1-yl)sulfonyl)-2-methyl-[1,1'-biphenyl]-3-carbonitrile (prepared in Step 1) (30 mg, 0.079 mmol) in ethanol was added hydrazine (0.025 mL, 0.793 mmol) and the resulting reaction mixture was refluxed for 2 h. The cooled reaction mixture was purified directly by RPCC (METHOD 2). (UPLC-MS, METHOD A) $t_R$ 1.20 min; API-MS 391.1 [M+H]$^+$.

Example 4: (R)-1-((4-(3-amino-4-methyl-1H-indazol-5-yl)-3-methylphenyl)sulfonyl)pyrrolidin-3-ol

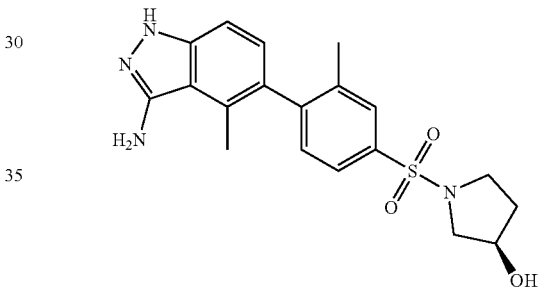

The title compound was prepared in an analogous manner to Example 1, using (R)-1-((4-bromo-3-methylphenyl)sulfonyl)pyrrolidin-3-ol (Intermediate 15) in place of 1-((4-bromo-3-chlorophenyl)sulfonyl)-3,3-dimethylazetidine (Intermediate 25). The filtered reaction mixture was purified directly by reverse phase HPLC (METHOD 1). The initial product was taken up in methanol and passed through a Varian Inc. stratosphere SPE PL-HCO3 MP resin. The eluant was concentrated under vacuum to provide the title compound. (UPLC-MS, METHOD A) $t_R$ 1.25 min; API-MS 387.1 [M+H]$^+$.

Example 5: (S)-1-((4-(3-amino-4-methyl-1H-indazol-5-yl)-3-methylphenyl)sulfonyl)pyrrolidin-3-ol

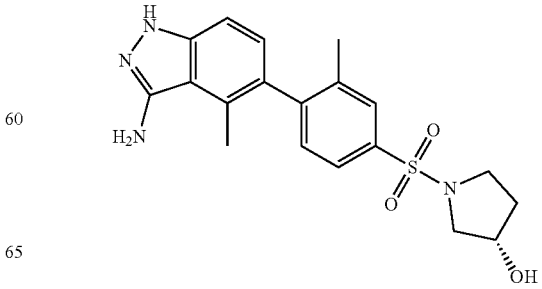

The title compound was prepared in an analogous manner to Example 1, using (S)-1-((4-bromo-3-methylphenyl)sulfonyl)pyrrolidin-3-ol (Intermediate 24) in place of 1-((4-bromo-3-chlorophenyl)sulfonyl)-3,3-dimethylazetidine (Intermediate 25). The filtered reaction mixture was purified directly by reverse phase HPLC (METHOD 1). The initial product was taken up in methanol and passed through a Varian Inc. stratosphere SPE PL-HCO3 MP resin. The eluant was concentrated under vacuum to provide the title compound. (UPLC-MS, METHOD A) $t_R$ 1.25 min; API-MS 387.1 [M+H]$^+$.

Example 6: (R)-1-((4-(3-amino-4-chloro-1H-indazol-5-yl)-3-fluorophenyl)sulfonyl)pyrrolidin-3-ol

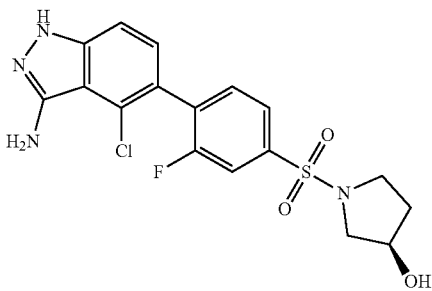 [SMILES: Nc1n[nH]c2ccc(-c3ccc(S(=O)(=O)N4CC[C@@H](O)C4)cc3F)c(Cl)c12]

A mixture of 4-chloro-5-(4,4,5,5-tetramethyl-1,3,2-dioxaborolan-2-yl)-1H-indazol-3-amine (Intermediate 5) (20 mg, 0.068 mmol), (R)-1-((4-bromo-3-fluorophenyl)sulfonyl)pyrrolidin-3-ol (Intermediate 14) (24 mg, 0.075 mmol), tricyclohexylphosphine (4.6 mg, 0.016 mmol), Pd$_2$(dba)$_3$ (6.2 mg, 6.8 μmol), K$_3$PO$_4$ (43 mg, 0.20 mmol) and dioxane/water (6:1, 3.4 ml) was sparged with nitrogen and was heated at 150° C. for 1 h. The cooled reaction mixture was concentrated and the residue purified directly by FCC to afford the title compound. $^1$H NMR (400 MHz, DMSO-d6) δ 12.02 (s, 1H), 7.77-7.71 (m, 2H), 7.66 (d, J=6.9 Hz, 1H), 7.32 (d, J=8.6 Hz, 1H), 7.22 (d, J=8.6 Hz, 1H), 5.32 (s, 2H), 4.98 (d, J=3.3 Hz, 1H), 4.21 (s, 1H), 3.39-3.36 (m, 3H), 3.16-3.11 (m, 1H), 1.87-1.60 (m, 2H). (UPLC-MS, METHOD B) $t_R$ 1.34 min; API-MS 411.1 [M+H]$^+$.

Example 7: (R)-1-((4-(3-amino-4-chloro-1H-indazol-5-yl)-3-methylphenyl)sulfonyl)pyrrolidin-3-ol

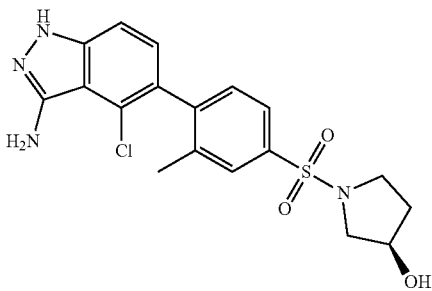 [SMILES: Cc1cc(S(=O)(=O)N2CC[C@@H](O)C2)ccc1-c1ccc2[nH]nc(N)c2c1Cl]

The title compound was prepared in an analogous manner to Example 6, using (R)-1-((4-bromo-3-methylphenyl)sulfonyl)pyrrolidin-3-ol (Intermediate 15) in place of (R)-1-((4-bromo-3-fluorophenyl)sulfonyl)pyrrolidin-3-ol (Intermediate 14). (UPLC-MS, METHOD B) $t_R$ 1.32 min; API-MS 407.1 [M+H]$^+$.

Example 8: (R)-1-((4-(3-amino-4-chloro-1H-indazol-5-yl)-3-chlorophenyl)sulfonyl)pyrrolidin-3-ol

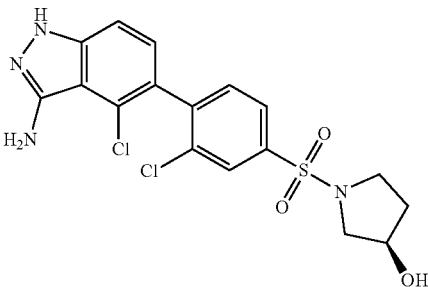 [SMILES: Nc1n[nH]c2ccc(-c3ccc(S(=O)(=O)N4CC[C@@H](O)C4)cc3Cl)c(Cl)c12]

The title compound was prepared in an analogous manner to Example 6, using (R)-1-((4-bromo-3-chlorophenyl)sulfonyl)pyrrolidin-3-ol (Intermediate 13) in place of (R)-1-((4-bromo-3-fluorophenyl)sulfonyl)pyrrolidin-3-ol (Intermediate 14). $^1$H NMR (400 MHz, DMSO-d6) δ 12.01 (s, 1H), 7.86-7.76 (m, 2H), 7.63 (d, J=8.0 Hz, 1H), 7.31 (d, J=8.5 Hz, 1H), 7.22-7.19 (m, 1H), 5.29 (s, 2H), 4.99 (d, J=3.3 Hz, 1H), 4.22 (s, 1H), 3.36 (dd, J=3.1, 1.1 Hz, 3H), 3.14 (d, J=10.9 Hz, 1H), 1.88-1.58 (m, 2H). (UPLC-MS, METHOD B) $t_R$ 1.40 min; API-MS 427.1 [M+H]$^+$. (UPLC-MS, METHOD B) $t_R$ 1.32 min; API-MS 407.1 [M+H]$^+$.

Example 9: 4-(3-amino-4-methyl-1H-indazol-5-yl)-N-((1r,3r)-3-hydroxycyclobutyl)-3-methylbenzenesulfonamide

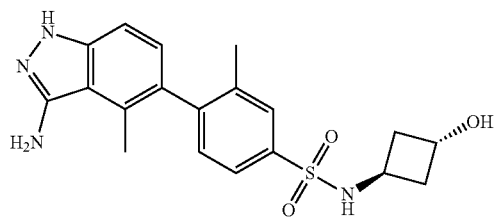 [SMILES: Cc1cc(S(=O)(=O)N[C@H]2C[C@H](O)C2)ccc1-c1ccc2[nH]nc(N)c2c1C]

4-methyl-5-(4,4,5,5-tetramethyl-1,3,2-dioxaborolan-2-yl)-1H-indazol-3-amine (Intermediate 6), 4-bromo-N-((1r,3r)-3-hydroxycyclobutyl)-3-methylbenzenesulfonamide (Intermediate 49) (10 mg, 0.037 mmol), (–, 0.040 mmol), tricyclohexylphosphine (6.3 μl, 8.8 μmol), Pd$_2$(dba)$_3$ (3.3 mg, 3.66 μmol), K$_3$PO$_4$ (23 mg, 0.110 mmol), and dioxane (6:1, 5.5 ml) was degassed with nitrogen and was heated at 150° C. for 30 minutes under microwave irradiation. The cooled reaction mixture was concentrated and the residue purified by FCC to afford the title compound. $^1$H NMR (400 MHz, DMSO-d6) δ 11.57 (s, 1H), 7.89 (s, 1H), 7.70 (d, J=1.7 Hz, 1H), 7.62 (dd, J=7.9, 1.7 Hz, 1H), 7.29 (d, J=8.0 Hz, 1H), 7.11 (d, J=8.4 Hz, 1H), 6.91 (d, J=8.5 Hz, 1H), 5.01-4.91 (m, 3H), 4.19-4.10 (m, 1H), 3.79 (s, 1H), 2.28 (s, 3H), 2.09 (s, 3H), 2.04-1.95 (m, 2H), 1.91 (ddd, J=9.8, 7.9, 3.9 Hz, 2H), 1.80 (d, J=8.2 Hz, 1H). (UPLC-MS, METHOD B) $t_R$ 1.02 min; API-MS 387.2 [M+H]$^+$.

Example 10: (S)-(1-((4-(3-amino-4-methyl-1H-indazol-5-yl)-3-methylphenyl)sulfonyl)azetidin-2-yl)methanol

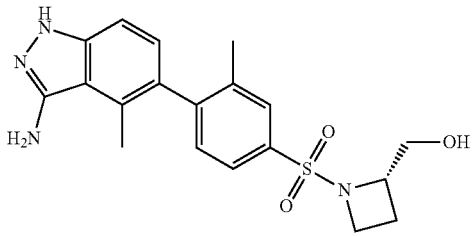 [SMILES: Cc1cc(S(=O)(=O)N2CC[C@H]2CO)ccc1-c1ccc2[nH]nc(N)c2c1C]

The title compound was prepared in an analogous manner to Example 9, using (S)-(1-((4-bromo-3-methylphenyl)sulfonyl)azetidin-2-yl)methanol (Intermediate 21) in place of 4-bromo-N-((1r,3r)-3-hydroxycyclobutyl)-3-methylbenzenesulfonamide (Intermediate 49). $^1$H NMR (400 MHz, DMSO-d6) δ 11.59 (s, 1H), 7.75 (d, J=1.6 Hz, 1H), 7.66 (dd, J=7.9, 1.7 Hz, 1H), 7.39 (d, J=7.9 Hz, 1H), 7.13 (d, J=8.5 Hz, 1H), 6.95 (d, J=8.5 Hz, 1H), 4.99 (s, 2H), 4.90 (t, J=5.7 Hz, 1H), 3.95-3.87 (m, 1H), 3.69-3.49 (m, 4H), 2.31 (s, 3H), 2.14 (s, 3H), 2.13-2.08 (m, 1H), 1.93-1.84 (m, 1H). (UPLC-MS, METHOD B) $t_R$ 1.29 min; API-MS 387.2 [M+H]$^+$.

Example 11: 1-((4-(3-amino-4-methyl-1H-indazol-5-yl)-3-methylphenyl)sulfonyl)azetidin-3-ol

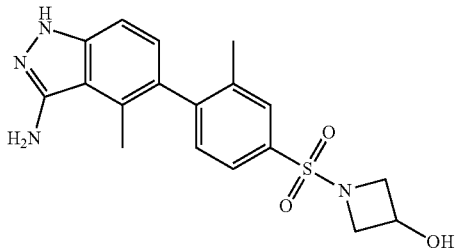 [SMILES: Cc1cc(S(=O)(=O)N2CC(O)C2)ccc1-c1ccc2[nH]nc(N)c2c1C]

The title compound was prepared in an analogous manner to Example 9, using 1-((4-bromo-3-methylphenyl)sulfonyl)-azetidin-3-ol (Intermediate 35) in place of 4-bromo-N-((1r,3r)-3-hydroxycyclobutyl)-3-methylbenzenesulfonamide (Intermediate 49). $^1$H NMR (400 MHz, DMSO-d6) δ 11.59 (s, 1H), 7.75 (d, J=1.6 Hz, 1H), 7.66 (dd, J=7.9, 1.7 Hz, 1H), 7.39 (d, J=7.9 Hz, 1H), 7.13 (d, J=8.5 Hz, 1H), 6.95 (d, J=8.5 Hz, 1H), 5.79 (s, 1H), 5.00 (s, 2H), 4.32 (s, 1H), 3.97-3.88 (m, 2H), 3.46-3.39 (m, 2H), 2.31 (s, 3H), 2.14 (s, 3H). (UPLC-MS, METHOD B) $t_R$ 1.12 min; API-MS 373.2 [M+H]$^+$.

Example 12: 4-(3-amino-4-methyl-1H-indazol-5-yl)-N-((1s,3s)-3-hydroxycyclobutyl)-3-methylbenzenesulfonamide

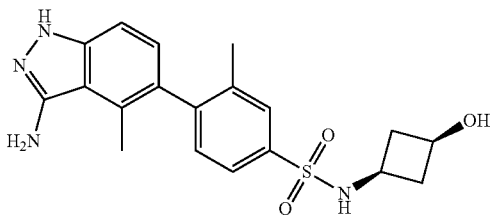 [SMILES: Cc1cc(S(=O)(=O)N[C@H]2C[C@@H](O)C2)ccc1-c1ccc2[nH]nc(N)c2c1C]

The title compound was prepared in an analogous manner to Example 9, using 4-bromo-N-((1s,3s)-3-hydroxycyclobutyl)-3-methylbenzenesulfonamide (Intermediate 55) in place 4-bromo-N-((1r,3r)-3-hydroxycyclobutyl)-3-methylbenzenesulfonamide (Intermediate 49). $^1$H NMR (400 MHz, DMSO-d6) δ 11.57 (s, 1H), 7.89 (s, 1H), 7.70 (d, J=1.7 Hz, 1H), 7.62 (dd, J=7.9, 1.7 Hz, 1H), 7.29 (d, J=8.0 Hz, 1H), 7.11 (d, J=8.4 Hz, 1H), 6.91 (d, J=8.5 Hz, 1H), 5.01-4.91 (m, 3H), 4.19-4.10 (m, 1H), 3.79 (s, 1H), 2.28 (s, 3H), 2.09 (s, 3H), 2.04-1.95 (m, 2H), 1.91 (ddd, J=9.8, 7.9, 3.9 Hz, 2H). (UPLC-MS, METHOD B) $t_R$ 1.11 min; API-MS 387.2 [M+H]$^+$.

Example 13: 1-((4-(3-amino-4-methyl-1H-indazol-5-yl)-3-methylphenyl)sulfonyl)-3-methylazetidin-3-ol

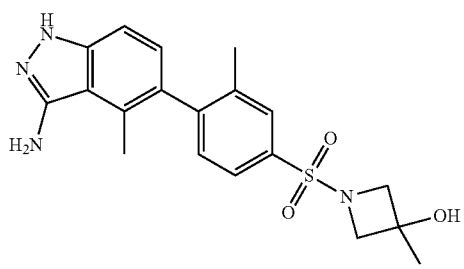 [SMILES: Cc1cc(S(=O)(=O)N2CC(C)(O)C2)ccc1-c1ccc2[nH]nc(N)c2c1C]

The title compound was prepared in an analogous manner to Example 9, using 1-((4-bromo-3-methylphenyl)sulfonyl)-3-methylazetidin-3-ol (Intermediate 31) in place of 4-bromo-N-((1r,3r)-3-hydroxycyclobutyl)-3-methylbenzenesulfonamide (Intermediate 49). $^1$H NMR (400 MHz, DMSO-d6) δ 11.58 (s, 1H), 7.76 (d, J=1.6 Hz, 1H), 7.66 (dd, J=7.9, 1.7 Hz, 1H), 7.39 (d, J=7.9 Hz, 1H), 7.13 (d, J=8.5 Hz, 1H), 6.93 (d, J=8.5 Hz, 1H), 5.67 (s, 1H), 4.99 (s, 2H), 3.66-3.51 (m, 4H), 2.30 (s, 3H), 2.14 (s, 3H), 1.17 (s, 3H). (UPLC-MS, METHOD B) $t_R$ 1.25 min; API-MS 387.2 [M+H]$^+$.

Example 14: 1-((4-(3-amino-4-methyl-1H-indazol-5-yl)-3-methylphenyl)sulfonyl)piperidin-4-ol

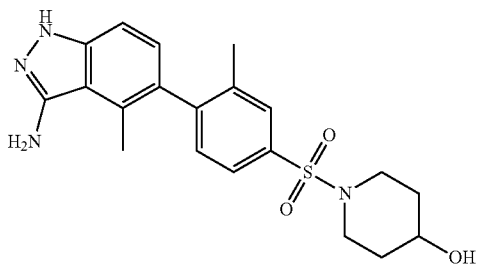 [SMILES: Cc1cc(S(=O)(=O)N2CCC(O)CC2)ccc1-c1ccc2[nH]nc(N)c2c1C]

The title compound was prepared in an analogous manner to Example 9, using 1-((4-bromo-3-methylphenyl)sulfonyl)piperidin-4-ol (Intermediate 37) in place of 4-bromo-N-((1r,3r)-3-hydroxycyclobutyl)-3-methylbenzenesulfonamide (Intermediate 49). $^1$H NMR (400 MHz, DMSO-d6) δ 11.58 (s, 1H), 7.68 (d, J=1.6 Hz, 1H), 7.59 (dd, J=7.9, 1.7 Hz, 1H), 7.34 (d, J=7.9 Hz, 1H), 7.12 (d, J=8.5 Hz, 1H), 6.93 (d, J=8.5 Hz, 1H), 4.99 (s, 2H), 4.72 (d, J=3.4 Hz, 1H), 3.62-3.53 (m, 1H), 3.21 (ddd, J=10.7, 6.5, 3.4 Hz, 2H), 2.85-2.76 (m, 2H), 2.30 (s, 3H), 2.11 (s, 3H), 1.67 (m, 2H), 1.47 (dtd, J=11.8, 8.0, 3.6 Hz, 2H). (UPLC-MS, METHOD B) $t_R$ 1.26 min; API-MS 401.2 [M+H]$^+$.

Example 15: 4-(3-amino-4-methyl-1H-indazol-5-yl)-N-((1R,2R)-2-hydroxycyclopentyl)-3-methylbenzenesulfonamide

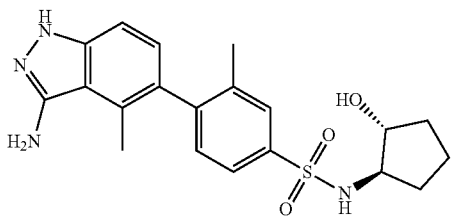 [SMILES: Cc1cc(S(=O)(=O)N[C@@H]2CCC[C@H]2O)ccc1-c1ccc2[nH]nc(N)c2c1C]

The title compound was prepared in an analogous manner to Example 9, using 4-bromo-N-((1R,2R)-2-hydroxycyclopentyl)-3-methylbenzenesulfonamide (Intermediate 45) in place of 4-bromo-N-((1r,3r)-3-hydroxycyclobutyl)-3-methylbenzenesulfonamide (Intermediate 49). $^1$H NMR (400 MHz, DMSO-d6) δ 11.57 (s, 1H), 7.75 (s, 1H), 7.67 (dd, J=7.9, 1.9 Hz, 1H), 7.54 (d, J=6.8 Hz, 1H), 7.29 (d, J=7.9 Hz, 1H), 7.12 (d, J=8.5 Hz, 1H), 6.92 (d, J=8.5 Hz, 1H), 4.98 (s, 2H), 4.71 (d, J=4.3 Hz, 1H), 3.88-3.79 (m, 1H), 3.24 (p, J=6.8 Hz, 1H), 2.29 (s, 3H), 2.09 (s, 3H), 1.80-1.66 (m, 2H), 1.54 (p, J=7.4 Hz, 2H), 1.37 (dtd, J=11.0, 7.3, 6.8, 4.4 Hz, 1H), 1.28 (td, J=12.8, 7.5 Hz, 1H). (UPLC-MS, METHOD B) $t_R$ 1.26 min; API-MS 401.2 [M+H]$^+$.

Example 16: 4-(3-amino-4-methyl-1H-indazol-5-yl)-N-((1R,2R)-2-hydroxycyclohexyl)-3-methylbenzenesulfonamide

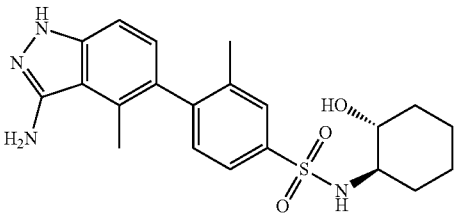 [SMILES: Cc1cc(S(=O)(=O)N[C@@H]2CCCC[C@H]2O)ccc1-c1ccc2[nH]nc(N)c2c1C]

The title compound was prepared in an analogous manner to Example 9, using 4-bromo-N-((1R,2R)-2-hydroxycyclohexyl)-3-methylbenzenesulfonamide (Intermediate 44) in place of 4-bromo-N-((1r,3r)-3-hydroxycyclobutyl)-3-methylbenzenesulfonamide (Intermediate 49). $^1$H NMR (400 MHz, DMSO-d6) δ 11.56 (s, 1H), 7.78 (s, 1H), 7.69 (d, J=7.9 Hz, 1H), 7.46 (d, J=7.1 Hz, 1H), 7.26 (d, J=7.9 Hz, 1H), 7.11 (d, J=8.5 Hz, 1H), 6.91 (d, J=8.5 Hz, 1H), 4.97 (s, 2H), 4.55 (dd, J=4.6, 1.6 Hz, 1H), 3.24 (dq, J=8.3, 4.2 Hz, 1H), 2.92-2.82 (m, 1H), 2.29 (s, 3H), 2.08 (s, 3H), 1.79 (d, J=11.0 Hz, 1H), 1.66 (d, J=9.1 Hz, 1H), 1.58-1.45 (m, 2H), 1.13 (dq, J=19.4, 11.4, 10.5 Hz, 4H). (UPLC-MS, METHOD B) $t_R$ 1.35 min; API-MS 415.2 [M+H]$^+$.

Example 17: 4-(3-amino-4-methyl-1H-indazol-5-yl)-N-((1R,2S)-2-hydroxycyclohexyl)-3-methylbenzenesulfonamide

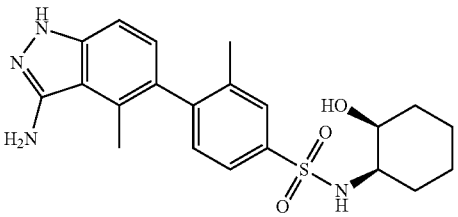 [SMILES: Cc1cc(S(=O)(=O)N[C@@H]2CCCC[C@@H]2O)ccc1-c1ccc2[nH]nc(N)c2c1C]

The title compound was prepared in an analogous manner to Example 9, using 4-bromo-N-((1R,2S)-2-hydroxycyclohexyl)-3-methylbenzenesulfonamide (Intermediate 46) in place of 4-bromo-N-((1r,3r)-3-hydroxycyclobutyl)-3-methylbenzenesulfonamide (Intermediate 49). (UPLC-MS, METHOD B) $t_R$ 1.36 min; API-MS 415.2 [M+H]$^+$.

Example 18: 4-(3-amino-4-methyl-1H-indazol-5-yl)-N-((1R,2S)-2-hydroxycyclopentyl)-3-methylbenzenesulfonamide

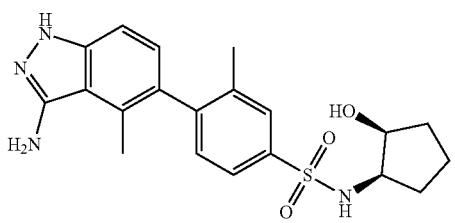 [SMILES: Cc1cc(S(=O)(=O)N[C@@H]2CCC[C@@H]2O)ccc1-c1ccc2[nH]nc(N)c2c1C]

The title compound was prepared in an analogous manner to Example 9, using 4-bromo-3-methyl-N-((1R,2S)-2-hydroxycyclopentyl)benzenesulfonamide (Intermediate 41) in place of 4-bromo-N-((1r,3r)-3-hydroxycyclobutyl)-3-methyl benzenesulfonamide (Intermediate 49). (UPLC-MS, METHOD B) $t_R$ 1.28 min; API-MS 401.2 [M+H]$^+$.

Example 19: (S)-(1-((4-(3-amino-4-methyl-1H-indazol-5-yl)-3-methylphenyl)sulfonyl)pyrrolidin-2-yl)methanol

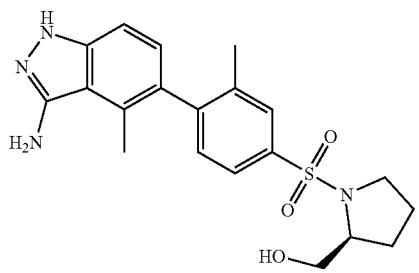 [SMILES: Cc1cc(S(=O)(=O)N2CCC[C@H]2CO)ccc1-c1ccc2[nH]nc(N)c2c1C]

The title compound was prepared in an analogous manner to Example 9, using (S)-(1-((4-bromo-3-methylphenyl)sulfonyl)pyrrolidin-2-yl)methanol (Intermediate 22) in place of 4-bromo-N-((1r,3r)-3-hydroxycyclobutyl)-3-methylbenzenesulfonamide (Intermediate 49). $^1$H NMR (400 MHz, DMSO-d6) δ 11.58 (s, 1H), 7.76 (s, 1H), 7.67 (d, J=7.9 Hz, 1H), 7.34 (d, J=7.9 Hz, 1H), 7.12 (d, J=8.5 Hz, 1H), 6.92 (d, J=8.5 Hz, 1H), 4.99 (s, 2H), 4.86 (t, J=5.6 Hz, 1H), 3.64-3.54 (m, 2H), 3.38-3.29 (m, 2H), 3.15 (qd, J=7.2, 4.0 Hz, 1H), 2.29 (s, 3H), 2.11 (s, 3H), 1.81 (dq, J=11.7, 7.1, 5.3 Hz, 2H), 1.47 (dt, J=16.7, 6.9 Hz, 2H). (UPLC-MS, METHOD B) $t_R$ 1.33 min; API-MS 401.2 [M+H]$^+$.

Example 20: (R)-(1-((4-(3-amino-4-methyl-1H-indazol-5-yl)-3-methylphenyl)sulfonyl)pyrrolidin-2-yl)methanol

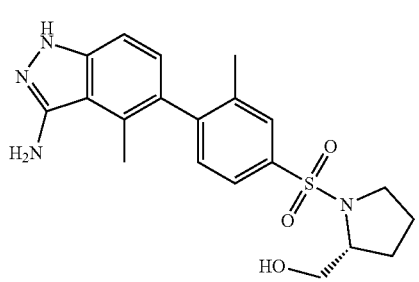 [SMILES: Cc1cc(S(=O)(=O)N2CCC[C@@H]2CO)ccc1-c1ccc2[nH]nc(N)c2c1C]

The title compound was prepared in an analogous manner to Example 9, using (R)-(1-((4-bromo-3-methylphenyl)sulfonyl)pyrrolidin-2-yl)methanol (Intermediate 12) in place of 4-bromo-N-((1r,3r)-3-hydroxycyclobutyl)-3-methylbenzenesulfonamide (Intermediate 49). $^1$H NMR (400 MHz, DMSO-d6) δ 11.58 (s, 1H), 7.76 (s, 1H), 7.67 (d, J=8.0 Hz, 1H), 7.34 (d, J=7.9 Hz, 1H), 7.12 (d, J=8.5 Hz, 1H), 6.92 (d, J=8.5 Hz, 1H), 4.99 (s, 2H), 4.86 (t, J=5.4 Hz, 1H), 3.64-3.54 (m, 2H), 3.38-3.30 (m, 2H), 3.20-3.09 (m, 1H), 2.29 (s, 3H), 2.11 (s, 3H), 1.85-1.75 (m, 2H), 1.54-1.40 (m, 2H). (UPLC-MS, METHOD B) $t_R$ 1.28 min; API-MS 401.2 [M+H]$^+$.

Example 21: 4-(3-amino-4-methyl-1H-indazol-5-yl)-3-methyl-N-(tetrahydro-2H-pyran-4-yl)benzenesulfonamide

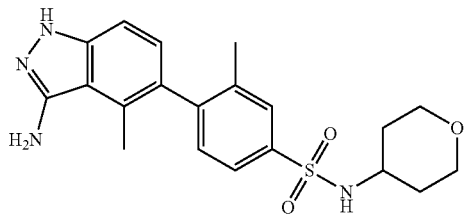 [SMILES: Cc1cc(S(=O)(=O)NC2CCOCC2)ccc1-c1ccc2[nH]nc(N)c2c1C]

The title compound was prepared in an analogous manner to Example 9, using 4-bromo-3-methyl-N-(tetrahydro-2H-pyran-4-yl)benzenesulfonamide (Intermediate 43) in place of 4-bromo-N-((1r,3r)-3-hydroxycyclobutyl)-3-methylbenzenesulfonamide (Intermediate 49). $^1$H NMR (400 MHz, DMSO-d6) δ 11.57 (s, 1H), 7.79 (d, J=7.3 Hz, 1H), 7.76 (d, J=1.4 Hz, 1H), 7.68 (dd, J=7.9, 1.7 Hz, 1H), 7.29 (d, J=8.0 Hz, 1H), 7.11 (d, J=8.5 Hz, 1H), 6.91 (d, J=8.5 Hz, 1H), 4.98 (s, 2H), 3.74 (dd, J=8.2, 3.3 Hz, 2H), 3.30-3.20 (m, 3H), 2.28 (s, 3H), 2.09 (s, 3H), 1.56 (d, J=10.3 Hz, 2H), 1.46-1.33 (m, 2H). (UPLC-MS, METHOD B) $t_R$ 1.31 min; API-MS 401.2 [M+H]$^+$.

Example 22: 1-((4-(3-amino-4-methyl-1H-indazol-5-yl)-3-methylphenyl)sulfonyl)azetidine-3-carbonitrile

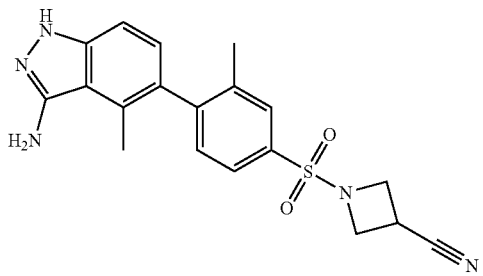 [SMILES: Cc1cc(S(=O)(=O)N2CC(C#N)C2)ccc1-c1ccc2[nH]nc(N)c2c1C]

The title compound was prepared in an analogous manner to Example 9, using 1-((4-bromo-3-methylphenyl)sulfonyl)azetidine-3-carbonitrile (Intermediate 36) in place of 4-bromo-N-((1r,3r)-3-hydroxycyclobutyl)-3-methylbenzenesulfonamide (Intermediate 49). $^1$H NMR (400 MHz, DMSO-d6) δ 11.59 (s, 1H), 7.81 (d, J=1.6 Hz, 1H), 7.71 (dd, J=7.9, 1.7 Hz, 1H), 7.43 (d, J=7.9 Hz, 1H), 7.13 (d, J=8.5 Hz, 1H), 6.93 (d, J=8.5 Hz, 1H), 4.99 (s, 2H), 4.08 (t, J=8.8 Hz, 2H), 3.89 (ddd, J=8.4, 6.1, 2.0 Hz, 2H), 3.68 (ddd, J=8.9, 6.1, 2.8 Hz, 1H), 2.32 (s, 3H), 2.15 (s, 3H). (UPLC-MS, METHOD B) $t_R$ 1.37 min; API-MS 382.2 [M+H]$^+$.

Example 23: 1-((4-(3-amino-4-methyl-1H-indazol-5-yl)-3-methylphenyl)sulfonyl)piperidine-4-carbonitrile

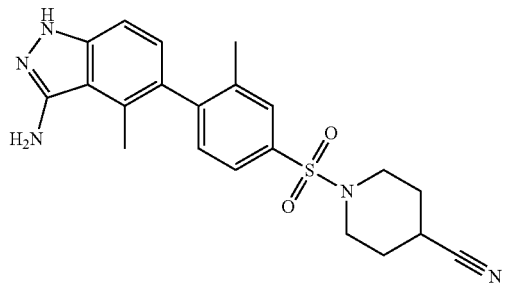 [SMILES: Cc1cc(S(=O)(=O)N2CCC(C#N)CC2)ccc1-c1ccc2[nH]nc(N)c2c1C]

The title compound was prepared in an analogous manner to Example 9, using 1-((4-bromo-3-methylphenyl)sulfonyl)-4-cyanopiperidine (Intermediate 34) in place of 4-bromo-N-((1r,3r)-3-hydroxycyclobutyl)-3-methylbenzenesulfonamide (Intermediate 49). $^1$H NMR (400 MHz, DMSO-d6) δ 11.58 (s, 1H), 7.70 (d, J=1.6 Hz, 1H), 7.61 (dd, J=7.9, 1.7 Hz, 1H), 7.36 (d, J=8.0 Hz, 1H), 7.12 (d, J=8.5 Hz, 1H), 6.92 (d, J=8.5 Hz, 1H), 4.99 (s, 2H), 3.28-3.20 (m, 2H), 2.98 (tt, J=8.4, 4.0 Hz, 1H), 2.85-2.75 (m, 2H), 2.29 (s, 3H), 2.12 (s, 3H), 1.98 (dq, J=9.4, 3.1 Hz, 2H), 1.79 (dtd, J=12.6, 8.9, 3.5 Hz, 2H). (UPLC-MS, METHOD B) $t_R$ 1.42 min; API-MS 410.2 [M+H]$^+$.

Example 24: 4-(3-amino-4-methyl-1H-indazol-5-yl)-N-(3,3-difluorocyclobutyl)-3-methylbenzenesulfonamide

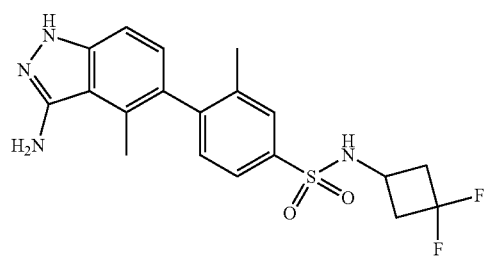 [SMILES: Cc1cc(S(=O)(=O)NC2CC(F)(F)C2)ccc1-c1ccc2[nH]nc(N)c2c1C]

The title compound was prepared in an analogous manner to Example 1, using 4-bromo-N-(3,3-difluorocyclobutyl)-3-methylbenzenesulfonamide (Intermediate 59) in place of 1-((4-bromo-3-chlorophenyl)sulfonyl)-3,3-dimethylazetidine (Intermediate 25). (UPLC-MS, METHOD B) $t_R$ 1.33 min; API-MS 407.2 [M+H]$^+$.

Example 25: 4-(3-amino-4-methyl-1H-indazol-5-yl)-N-(3-hydroxycyclohexyl)-3-methylbenzenesulfonamide

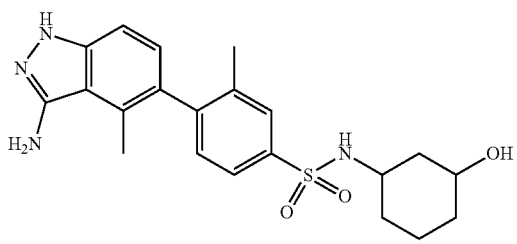 [SMILES: Cc1cc(S(=O)(=O)NC2CCCC(O)C2)ccc1-c1ccc2[nH]nc(N)c2c1C]

The title compound was prepared in an analogous manner to Example 1, using 4-bromo-N-(3-hydroxycyclohexyl)-3-methylbenzenesulfonamide (Intermediate 65) in place of 1-((4-bromo-3-chlorophenyl)sulfonyl)-3,3-dimethylazetidine (Intermediate 25). (UPLC-MS, METHOD B) $t_R$ 1.17 min; API-MS 415.2 [M+H]$^+$.

Example 26: 4-(3-amino-4-methyl-1H-indazol-5-yl)-N-((1R,3R)-3-cyanocyclohexyl)-3-methylbenzenesulfonamide

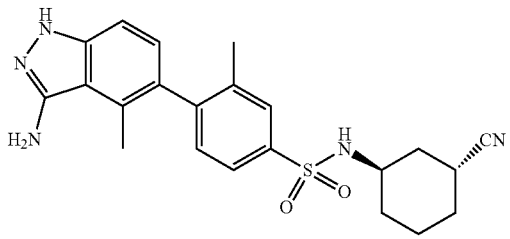 [SMILES: Cc1cc(S(=O)(=O)N[C@@H]2CCC[C@@H](C#N)C2)ccc1-c1ccc2[nH]nc(N)c2c1C]

The title compound was prepared in an analogous manner to Example 1, using 4-bromo-N-((1R,3R)-3-cyanocyclohexyl)-3-methylbenzenesulfonamide (Intermediate 48) in place of 1-((4-bromo-3-chlorophenyl)sulfonyl)-3,3-dimethylazetidine (Intermediate 25). (UPLC-MS, METHOD B) $t_R$ 1.31 min; API-MS 424.1 [M+H]$^+$.

Example 27: 4-(3-amino-4-methyl-1H-indazol-5-yl)-N-((1s,4s)-4-cyanocyclohexyl)-3-methylbenzenesulfonamide

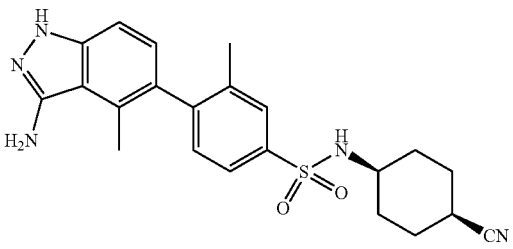 [SMILES: Cc1cc(S(=O)(=O)N[C@H]2CC[C@@H](C#N)CC2)ccc1-c1ccc2[nH]nc(N)c2c1C]

The title compound was prepared in an analogous manner to Example 1, using 4-bromo-N-((1s,4s)-4-cyanocyclohexyl)-3-methylbenzenesulfonamide (Intermediate 56) in place of 1-((4-bromo-3-chlorophenyl)sulfonyl)-3,3-dimethylazetidine (Intermediate 25). (UPLC-MS, METHOD B) $t_R$ 1.31 min; API-MS 424.2 [M+H]$^+$.

Example 28: (S)-(1-((4-(3-amino-4-chloro-1H-indazol-5-yl)-3-methylphenyl)sulfonyl)pyrrolidin-2-yl)methanol

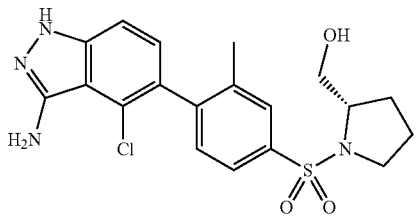 [SMILES: Cc1cc(S(=O)(=O)N2CCC[C@H]2CO)ccc1-c1ccc2[nH]nc(N)c2c1Cl]

A mixture of 4-chloro-5-(4,4,5,5-tetramethyl-1,3,2-dioxaborolan-2-yl)-1H-indazol-3-amine (Intermediate 5) (25 mg, 0.085 mmol), (S)-(1-((4-bromo-3-methylphenyl)sulfonyl)pyrrolidin-2-yl)methanol (Intermediate 22) (31 mg, 0.094 mmol), PdCl2(dppf) (3.1 mg, 4.3 µmol), potassium carbonate (24 mg, 0.17 mmol), and 4:1 dioxane/water (5 ml) was sparged with nitrogen and was heated at 150° C. for 1 h under microwave irradiation. The cooled reaction mixture was added to celite, concentrated, and purified by FCC to afford the title compound. $^1$H NMR (400 MHz, DMSO-d6) δ 11.96 (s, 1H), 7.79 (s, 1H), 7.70 (d, J=8.0 Hz, 1H), 7.41 (d, J=8.0 Hz, 1H), 7.30 (d, J=8.5 Hz, 1H), 7.11 (d, J=8.5 Hz, 1H), 5.26 (s, 2H), 4.87 (t, J=5.4 Hz, 1H), 4.11 (q, J=5.2 Hz, 1H), 3.63-3.55 (m, 2H), 3.38-3.34 (m, 1H), 3.16-3.11 (m, 1H), 2.17 (s, 3H), 1.87-1.75 (m, 2H), 1.47 (dq, J=17.5, 7.0, 5.7 Hz, 2H). (UPLC-MS, METHOD B) $t_R$ 1.37 min; API-MS 421.1 [M+H]$^+$.

Example 29: 4-(3-amino-4-chloro-1H-indazol-5-yl)-N-((1R,2S)-2-hydroxycyclopentyl)-3-methylbenzenesulfonamide

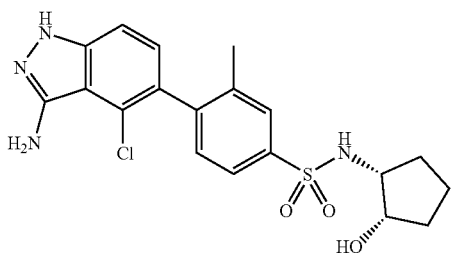

The title compound was prepared in an analogous manner to Example 28, using 4-bromo-3-methyl-N-((1R,2S)-2-hydroxycyclopentyl)benzenesulfonamide (Intermediate 41) in place of (S)-(1-((4-bromo-3-methylphenyl)sulfonyl)pyrrolidin-2-yl)methanol (Intermediate 22). $^1$H NMR (400 MHz, DMSO-d6) δ 11.95 (s, 1H), 7.81 (d, J=1.9 Hz, 1H), 7.73 (dt, J=8.0, 2.0 Hz, 1H), 7.36-7.26 (m, 3H), 7.09 (d, J=8.5 Hz, 1H), 5.25 (s, 2H), 4.68 (d, J=4.0 Hz, 1H), 3.82 (dd, J=4.2, 1.9 Hz, 1H), 3.31 (ddd, J=2.8, 1.3, 0.6 Hz, 1H), 1.71-1.56 (m, 2H), 1.53-1.42 (m, 3H), 1.36 (td, J=12.5, 12.0, 7.5 Hz, 1H). (UPLC-MS, METHOD B) $t_R$ 1.37 min; API-MS 421.1 [M+H]$^+$.

Example 30: 4-(3-amino-4-chloro-1H-indazol-5-yl)-N-((1s,3s)-3-hydroxycyclobutyl)-3-methylbenzenesulfonamide

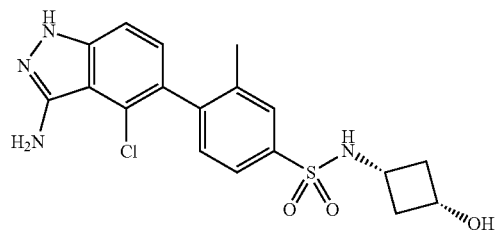 [SMILES: Cc1cc(S(=O)(=O)N[C@H]2C[C@@H](O)C2)ccc1-c1ccc2[nH]nc(N)c2c1Cl]

The title compound was prepared in an analogous manner to Example 28, using 4-bromo-N-((1s,3s)-3-hydroxycyclobutyl)-3-methylbenzenesulfonamide (Intermediate 55) in place of (S)-(1-((4-bromo-3-methylphenyl)sulfonyl)pyrrolidin-2-yl)methanol (Intermediate 22). $^1$H NMR (400 MHz, DMSO-d6) δ 11.95 (s, 1H), 7.89 (d, J=8.5 Hz, 1H), 7.73 (s, 1H), 7.66 (dd, J=8.0, 1.6 Hz, 1H), 7.35 (d, J=8.0 Hz, 1H), 7.29 (d, J=8.5 Hz, 1H), 7.08 (d, J=8.5 Hz, 1H), 5.25 (s, 2H), 5.04 (d, J=5.6 Hz, 1H), 3.73-3.64 (m, 1H), 3.14 (d, J=7.4 Hz, 1H), 2.27 (dp, J=9.4, 3.6 Hz, 2H), 2.14 (s, 3H), 1.63 (qd, J=8.7, 2.9 Hz, 2H). (UPLC-MS, METHOD B) $t_R$ 1.22 min; API-MS 407.1 [M+H]$^+$.

Example 31: 4-(3-amino-4-methyl-1H-indazol-5-yl)-N-((1s,3s)-3-hydroxy-3-(trifluoromethyl)cyclobutyl)-3-methylbenzenesulfonamide

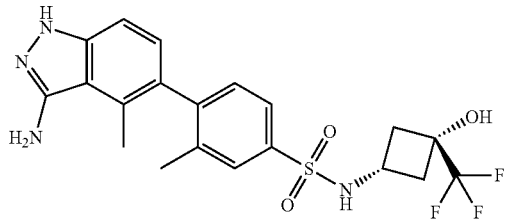 [SMILES: Cc1cc(S(=O)(=O)N[C@H]2C[C@](O)(C(F)(F)F)C2)ccc1-c1ccc2[nH]nc(N)c2c1C]

A mixture of 4-methyl-5-(4,4,5,5-tetramethyl-1,3,2-dioxaborolan-2-yl)-1H-indazol-3-amine (Intermediate 6) (10 mg, 0.037 mmol), 4-bromo-N-((1s,3s)-3-hydroxy-3-(trifluoromethyl)cyclobutyl)-3-methylbenzenesulfonamide (Intermediate 9) (14 mg, 0.037 mmol), PdCl$_2$(dppf) (1.339 mg, 1.831 μmol), potassium carbonate (10 mg, 0.073 mmol) and dioxane/water (4:1, 0.7 ml) was sparged with nitrogen and was then heated at 150° C. for 1 h. Celite was added and the mixture was concentrated, then the residue was purified by FCC to afford the title compound. $^1$H NMR (400 MHz, DMSO-d6) δ 11.57 (s, 1H), 8.14 (d, J=8.4 Hz, 1H), 7.73 (d, J=1.7 Hz, 1H), 7.64 (dd, J=7.9, 1.7 Hz, 1H), 7.30 (d, J=8.0 Hz, 1H), 7.11 (d, J=8.5 Hz, 1H), 6.90 (d, J=8.5 Hz, 1H), 6.63 (s, 1H), 4.97 (s, 2H), 3.44-3.37 (m, 1H), 2.53 (dd, J=6.8, 2.9 Hz, 2H), 2.28 (s, 3H), 2.09 (s, 3H), 2.04 (d, J=13.0 Hz, 2H). (UPLC-MS, METHOD B) $t_R$ 1.41 min; API-MS 455.2 [M+H]$^+$.

Example 32: (S)-(1-((4-(3-amino-4-methyl-1H-indazol-5-yl)-3-methylphenyl)sulfonyl)-4,4-difluoropyrrolidin-2-yl)methanol

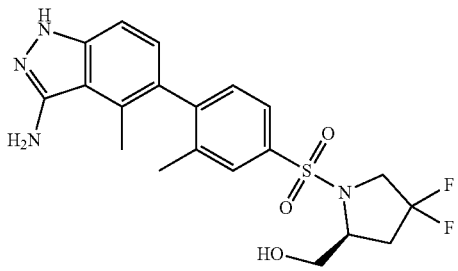 [SMILES: Cc1cc(S(=O)(=O)N2CC(F)(F)C[C@H]2CO)ccc1-c1ccc2[nH]nc(N)c2c1C]

A mixture of 4-methyl-5-(4,4,5,5-tetramethyl-1,3,2-dioxaborolan-2-yl)-1H-indazol-3-amine (Intermediate 6) (200 mg, 0.732 mmol), (S)-(1-((4-bromo-3-methylphenyl)sulfonyl)-4,4-difluoropyrrolidin-2-yl)methanol (Intermediate 20) (298 mg, 0.805 mmol), PdCl$_2$(dppf) (27 mg, 0.037 mmol), potassium carbonate (304 mg, 2.20 mmol), and dioxane/water (4:1, 15 ml) was sparged with nitrogen and was then heated at 150° C. under microwave irradiation for 1 h.

The reaction mixture was added to celite, then concentrated. The celite-adsorbed residue was purified by FCC to afford the title compound.

A mixture of 900 mg of the chromatographed product and 45 ml of isopropyl alcohol was heated to reflux. To the resulting solution was added 180 ml water and a white precipitate formed. The mixture was heated to 90° C. and the solution went clear. The mixture was allowed to cool to RT, and was then placed in a −20° C. freezer for 4 h. The mixture was then allowed to sit at RT for 20 h, during which time a precipitate formed. The precipitate was collected to provide the title compound as an off-white crystalline solid. $^1$H NMR (400 MHz, DMSO-d6) δ 11.58 (s, 1H), 7.85-7.80 (m, 1H), 7.72 (dt, J=7.9, 2.6 Hz, 1H), 7.33 (d, J=8.0 Hz, 1H), 7.12 (d, J=8.5 Hz, 1H), 6.91 (d, J=8.5 Hz, 1H), 5.11 (td, J=5.6, 0.8 Hz, 1H), 4.99 (s, 2H), 3.91 (ddd, J=8.6, 6.3, 3.7 Hz, 1H), 3.87-3.67 (m, 2H), 3.61 (dp, J=11.0, 5.8 Hz, 2H), 2.47-2.28 (m, 2H), 2.27 (s, 3H), 2.11 (s, 3H). (UPLC-MS, METHOD B) $t_R$ 1.27 min; API-MS 437.2 [M+H]$^+$.

Example 33: (S)-(1-((4-(3-amino-4-methyl-1H-indazol-5-yl)-3-methylphenyl)sulfonyl)-4-fluoro-2,5-dihydro-1H-pyrrol-2-yl)methanol

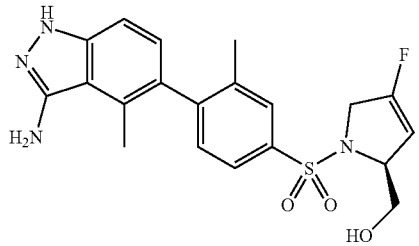 [SMILES: Cc1cc(S(=O)(=O)N2CC(F)=C[C@H]2CO)ccc1-c1ccc2[nH]nc(N)c2c1C]

A mixture of 4-methyl-5-(4,4,5,5-tetramethyl-1,3,2-dioxaborolan-2-yl)-1H-indazol-3-amine (Intermediate 6) (10.02 g, 36.7 mmol), (S)-(1-((4-bromo-3-methylphenyl)sulfonyl)-4,4-difluoropyrrolidin-2-yl)methanol (Intermediate 20) (14.94 g, 40.4 mmol), PdCl$_2$(dppf) (1.34 g, 1.83 mmol), potassium carbonate (15.2 g, 110 mmol), and dioxane/water (4:1, 366 ml) was sparged with argon, and was then refluxed for 4 h. Celite was added to the cooled reaction mixture, and the mixture was concentrated. The residue was purified by flash column chromatography (220 g column, 0-100% [3:1 ethyl acetate:ethanol]/DCM gradient). The partially purified product mixture was then subjected to RPCC (METHOD 2) to give the major product (S)-(1-((4-(3-amino-4-methyl-1H-indazol-5-yl)-3-methylphenyl)sulfonyl)-4,4-difluoropyrrolidin-2-yl)methanol as a white amorphous solid and (S)-(1-((4-(3-amino-4-methyl-1H-indazol-5-yl)-3-methylphenyl)sulfonyl)-4-fluoro-2,5-dihydro-1H-pyrrol-2-yl)methanol as a minor product. $^1$H NMR (400 MHz, DMSO-d6) δ 11.57 (s, 1H), 7.82 (s, 1H), 7.72 (d, J=9.8 Hz, 1H), 7.34 (d, J=8.0 Hz, 1H), 7.11 (d, J=8.5 Hz, 1H), 6.92 (d, J=8.5 Hz, 1H), 5.33-5.27 (m, 1H), 4.98 (s, 2H), 4.96 (t, J=8.0 Hz, 1H), 4.36 (brs, 1H), 4.18 (brs, 2H), 3.73-3.63 (m, 1H), 3.55-3.48 (m, 1H), 2.58-2.49 (m, 1H), 2.27 (s, 3H), 2.11 (s, 3H). (UPLC-MS, METHOD B) $t_R$ 1.29 min; API-MS 417.2 [M+H]$^+$.

Example 34: 4-(3-amino-4-methyl-1H-indazol-5-yl)-3-chloro-N-((1s,3s)-3-hydroxycyclobutyl)benzenesulfonamide

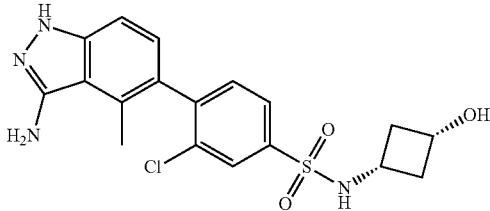 [SMILES: Cc1c(-c2ccc(S(=O)(=O)N[C@H]3C[C@@H](O)C3)cc2Cl)ccc2[nH]nc(N)c12]

The title compound was prepared in an analogous manner to Example 31, using 4-bromo-N-((1s,3s)-3-hydroxycyclobutyl)-3-chlorobenzenesulfonamide (Intermediate 54) in place of 4-bromo-N-((1s,3s)-3-hydroxy-3-(trifluoromethyl)cyclobutyl)-3-methylbenzenesulfonamide (Intermediate 9). $^1$H NMR (400 MHz, DMSO-d6) δ 11.64 (s, 1H), 8.08 (s, 1H), 7.91 (d, J=1.8 Hz, 1H), 7.78 (dd, J=8.0, 1.8 Hz, 1H), 7.53 (d, J=8.0 Hz, 1H), 7.13 (d, J=8.5 Hz, 1H), 6.96 (d, J=8.5 Hz, 1H), 5.09 (s, 1H), 5.03 (s, 2H), 3.69 (q, J=7.0 Hz, 1H), 3.21 (d, J=7.4 Hz, 1H), 2.34 (s, 3H), 2.28 (dt, J=10.7, 6.6 Hz, 2H), 1.63 (q, J=9.2 Hz, 2H). (UPLC-MS, METHOD B) $t_R$ 1.11 min; API-MS 407.1 [M+H]$^+$.

Example 35: 4-(3-amino-4-methyl-1H-indazol-5-yl)-N-((1R,3S)-3-hydroxycyclopentyl)-3-methylbenzenesulfonamide

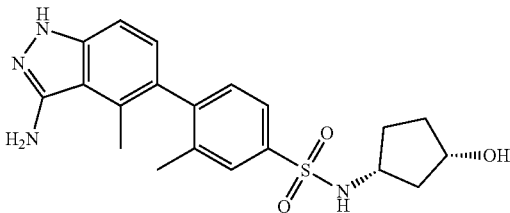 [SMILES: Cc1cc(S(=O)(=O)N[C@@H]2CC[C@H](O)C2)ccc1-c1ccc2[nH]nc(N)c2c1C]

The title compound was prepared in an analogous manner to Example 31, using 4-bromo-N-((1R,3S)-3-hydroxycyclopentyl)-3-methyl benzenesulfonamide (Intermediate 50) in place of 4-bromo-N-((1s,3s)-3-hydroxy-3-(trifluoromethyl)cyclobutyl)-3-methylbenzenesulfonamide (Intermediate 9). (UPLC-MS, METHOD B) $t_R$ 1.12 min; API-MS 401.2 [M+H]$^+$.

Example 36: 4-(3-amino-4-methyl-1H-indazol-5-yl)-N-((1s,3s)-3-hydroxy-1-methylcyclobutyl)-3-methylbenzenesulfonamide

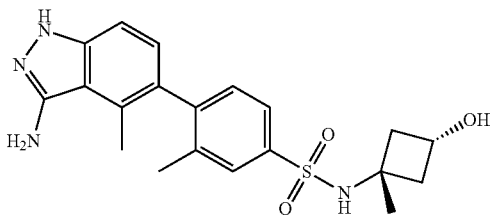 [SMILES: Cc1cc(S(=O)(=O)N[C@]2(C)C[C@H](O)C2)ccc1-c1ccc2[nH]nc(N)c2c1C]

The title compound was prepared in an analogous manner to Example 31, using 4-bromo-N-((1s,3s)-3-hydroxy-1-methylcyclobutyl)-3-methylbenzenesulfonamide (Intermediate 52) in place of 4-bromo-N-((1s,3s)-3-hydroxy-3-(trifluoromethyl)cyclobutyl)-3-methylbenzenesulfonamide (Intermediate 9). $^1$H NMR (400 MHz, DMSO-d6) δ 11.57 (s, 1H), 7.83 (s, 1H), 7.74 (d, J=1.7 Hz, 1H), 7.66 (dd, J=7.9, 1.7 Hz, 1H), 7.28 (d, J=8.0 Hz, 1H), 7.11 (d, J=8.5 Hz, 1H), 6.91 (d, J=8.5 Hz, 1H), 5.02 (d, J=5.7 Hz, 1H), 4.98 (s, 2H), 3.87 (h, J=7.3 Hz, 1H), 2.29 (s, 3H), 2.08 (s, 3H), 2.06 (dd, J=6.8, 2.6 Hz, 2H), 1.97 (t, J=9.5 Hz, 2H), 1.21 (s, 3H). (UPLC-MS, METHOD B) $t_R$ 1.11 min; API-MS 401.2 [M+H]$^+$.

Example 37: 4-(3-amino-4-chloro-1H-indazol-5-yl)-N-((1s,3s)-3-hydroxy-3-(trifluoromethyl)cyclobutyl)-3-methylbenzenesulfonamide

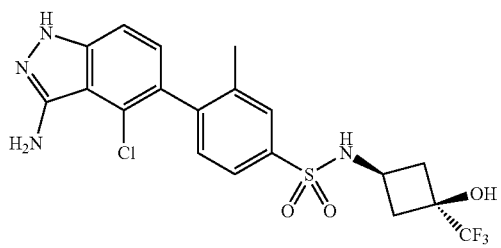 [SMILES: Cc1cc(S(=O)(=O)N[C@H]2C[C@](O)(C(F)(F)F)C2)ccc1-c1ccc2[nH]nc(N)c2c1Cl]

The title compound was prepared in an analogous manner to Example 28, using 4-bromo-N-((1s,3s)-3-hydroxy-3-(trifluoromethyl)cyclobutyl)-3-methylbenzenesulfonamide (Intermediate 9) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.96 (s, 1H), 8.18 (d, J=8.3 Hz, 1H), 7.75 (d, J=1.4 Hz, 1H), 7.67 (dd, J=8.0, 1.7 Hz, 1H), 7.38 (d, J=8.0 Hz, 1H), 7.30 (d, J=8.5 Hz, 1H), 7.09 (d, J=8.5 Hz, 1H), 6.63 (s, 1H), 5.25 (s, 2H), 3.46-3.37 (m, 1H), 2.55 (dd, J=6.9, 2.9 Hz, 2H), 2.15 (s, 3H), 2.10-2.03 (m, 2H). (UPLC-MS, METHOD B) $t_R$ 1.39 min; API-MS 475.1 [M+H]$^+$.

Example 38: (S)-(1-((4-(3-amino-4-methyl-1H-indazol-5-yl)-3-chlorophenyl)sulfonyl)pyrrolidin-2-yl)methanol The title compound was prepared in an analogous manner to Example 31, using (S)-(1-((4-bromo-3-chlorophenyl)sulfonyl)pyrrolidin-2-yl)methanol (Intermediate 18) in place of 4-bromo-N-((1s,3s)-3-hydroxy-3-(trifluoromethyl)cyclobutyl)-3-methylbenzenesulfonamide (Intermediate 9). $^1$H NMR (400 MHz, DMSO-d6) δ 11.64 (s, 1H), 7.94 (t, J=1.8 Hz, 1H), 7.84 (d, J=8.6 Hz, 1H), 7.57 (d, J=8.0 Hz, 1H), 7.13 (d, J=8.5 Hz, 1H), 6.98 (d, J=8.5 Hz, 1H), 5.03 (s, 2H), 4.94-4.85 (m, 1H), 3.67-3.54 (m, 2H), 3.41-3.35 (m, 2H), 3.21 (d, J=6.9 Hz, 1H), 2.34 (s, 3H), 1.83 (dd, J=10.8, 6.8 Hz, 2H), 1.52 (d, J=7.5 Hz, 2H). (UPLC-MS, METHOD B) $t_R$ 1.34 min; API-MS 421.2 [M+H]$^+$.

Example 39: 4-(3-amino-4-methyl-1H-indazol-5-yl)-3-chloro-N-((1R,2S)-2-hydroxycyclopentyl)benzenesulfonamide

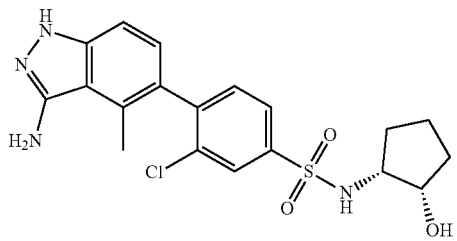 [SMILES: Cc1c(-c2ccc(S(=O)(=O)N[C@@H]3CCC[C@@H]3O)cc2Cl)ccc2[nH]nc(N)c12]

The title compound was prepared in an analogous manner to Example 31, using 4-bromo-3-chloro-N-((1R,2S)-2-hydroxycyclopentyl)benzenesulfonamide (Intermediate 38) in place of 4-bromo-N-((1s,3s)-3-hydroxy-3-(trifluoromethyl)cyclobutyl)-3-methylbenzenesulfonamide (Intermediate 9). $^1$H NMR (400 MHz, DMSO-d6) δ 11.62 (s, 1H), 8.02 (dd, J=5.4, 1.8 Hz, 1H), 7.87-7.81 (m, 1H), 7.58 (d, J=8.0 Hz, 1H), 7.51 (dd, J=8.0, 1.0 Hz, 1H), 7.13 (d, J=8.5 Hz, 1H), 6.96 (d, J=8.5 Hz, 1H), 5.02 (s, 2H), 4.74 (dd, J=3.9, 1.6 Hz, 1H), 3.86-3.77 (m, 1H), 3.41-3.38 (m, 1H), 2.33 (s, 3H), 1.70-1.58 (m, 2H), 1.54-1.41 (m, 3H), 1.37 (dd, J=12.7, 8.5 Hz, 1H). (UPLC-MS, METHOD B) $t_R$ 1.33 min; API-MS 421.1 [M+H]$^+$.

Example 40: 4-(3-amino-4-methyl-1H-indazol-5-yl)-N-((1s,3s)-3-hydroxy-3-methylcyclobutyl)-3-methylbenzenesulfonamide

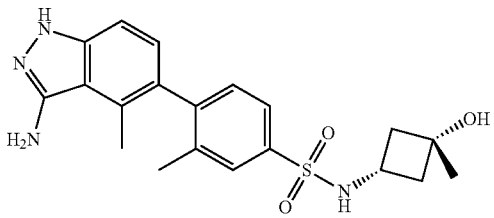 [SMILES: Cc1cc(S(=O)(=O)N[C@H]2C[C@@](C)(O)C2)ccc1-c1ccc2[nH]nc(N)c2c1C]

The title compound was prepared in an analogous manner to Example 31, using 4-bromo-N-((1s,3s)-3-hydroxy-3-methylcyclobutyl)-3-methylbenzenesulfonamide (Intermediate 53) in place of 4-bromo-N-((1s,3s)-3-hydroxy-3-(trifluoromethyl)cyclobutyl)-3-methylbenzenesulfonamide (Intermediate 9). $^1$H NMR (400 MHz, DMSO-d6) δ 11.56 (s, 1H), 7.85 (d, J=5.9 Hz, 1H), 7.71 (d, J=1.6 Hz, 1H), 7.63 (dd, J=7.9, 1.7 Hz, 1H), 7.27 (d, J=7.9 Hz, 1H), 7.11 (d, J=8.5 Hz, 1H), 6.90 (d, J=8.5 Hz, 1H), 4.97 (s, 2H), 4.93 (s, 1H), 3.26 (d, J=7.9 Hz, 1H), 2.28 (s, 3H), 2.08 (s, 3H), 2.04-1.95 (m, 2H), 1.82 (t, J=10.0 Hz, 2H), 1.12 (s, 3H). (UPLC-MS, METHOD B) $t_R$ 1.12 min; API-MS 401.2 [M+H]$^+$.

Example 41: (S)-(1-((4-(3-amino-4-methoxy-1H-indazol-5-yl)-3-fluorophenyl)sulfonyl)-4,4-difluoropyrrolidin-2-yl)methanol

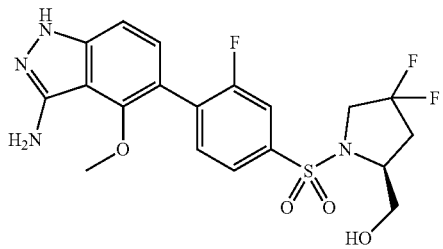 [SMILES: COc1c(-c2ccc(S(=O)(=O)N3CC(F)(F)C[C@H]3CO)cc2F)ccc2[nH]nc(N)c12]

The title compound was prepared in an analogous manner to Example 28, using 4-methoxy-5-(4,4,5,5-tetramethyl-1,3,2-dioxaborolan-2-yl)-1H-indazol-3-amine (Intermediate 8) in place of 4-chloro-5-(4,4,5,5-tetramethyl-1,3,2-dioxaborolan-2-yl)-1H-indazol-3-amine (Intermediate 5), and using (S)-(1-((4-bromo-3-fluorophenyl)sulfonyl)-4,4-difluoropyrrolidin-2-yl)methanol (Intermediate 19) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.71 (s, 1H), 7.84 (d, J=9.3 Hz, 1H), 7.78 (dd, J=8.1, 1.5 Hz, 1H), 7.71 (t, J=7.6 Hz, 1H), 7.15 (d, J=8.5 Hz, 1H), 7.08 (d, J=8.5 Hz, 1H), 5.18 (s, 2H), 5.12 (t, J=5.6 Hz, 1H), 3.98-3.89 (m, 2H), 3.74 (ddd, J=23.6, 13.0, 6.9 Hz, 1H), 3.61 (t, J=4.9 Hz, 2H), 3.47 (s, 3H), 2.35 (ddd, J=28.4, 15.9, 6.2 Hz, 2H). (UPLC-MS, METHOD B) $t_R$ 1.26 min; API-MS 457.2 [M+H]$^+$.

Example 42: (S)-(1-((4-(3-amino-4-methyl-1H-indazol-5-yl)-3-fluorophenyl)sulfonyl)-4,4-difluoropyrrolidin-2-yl)methanol

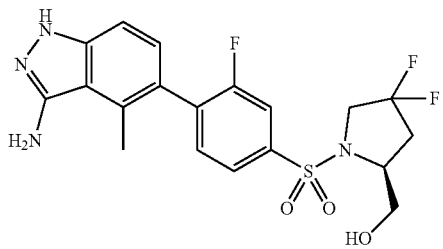 [SMILES: Cc1c(-c2ccc(S(=O)(=O)N3CC(F)(F)C[C@H]3CO)cc2F)ccc2[nH]nc(N)c12]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using (S)-(1-((4-bromo-3-fluorophenyl)sulfonyl)-4,4-difluoropyrrolidin-2-yl)methanol (Intermediate 19) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.65 (s, 1H), 7.85 (dd, J=9.2, 1.8 Hz, 1H), 7.78 (dd, J=8.0, 1.8 Hz, 1H), 7.58 (t, J=7.7 Hz, 1H), 7.16 (d, J=8.6 Hz, 1H), 7.05 (d, J=8.6 Hz, 1H), 5.13 (t, J=5.7 Hz, 1H), 5.06 (s, 2H), 3.95 (q, J=11.5, 8.0 Hz, 2H), 3.74 (ddd, J=23.4, 13.0, 7.0 Hz, 1H), 3.62 (t, J=5.1 Hz, 2H), 2.44-2.40

(m, 3H), 2.41-2.29 (m, 2H). (UPLC-MS, METHOD B) $t_R$ 1.26 min; API-MS 441.2 [M+H]$^+$.

Example 43: 4-(3-amino-4-methyl-1H-indazol-5-yl)-N-(4,4-difluorocyclohexyl)-3-methylbenzenesulfonamide

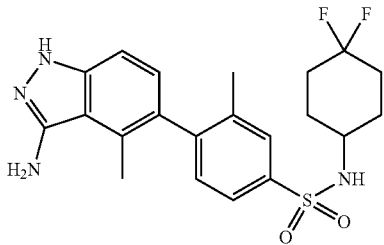 [SMILES: Cc1cc(S(=O)(=O)NC2CCC(F)(F)CC2)ccc1-c1ccc2[nH]nc(N)c2c1C]

The title compound was prepared in an analogous manner to Example 1, using 4-bromo-N-(4,4-difluorocyclohexyl)-3-methylbenzenesulfonamide (Intermediate 66) in place of 1-((4-bromo-3-chlorophenyl)sulfonyl)-3,3-dimethylazetidine (Intermediate 25). (UPLC-MS, METHOD B) $t_R$ 1.50 min; API-MS 435.2 [M+H]$^+$.

Example 44: (S)-(1-((4-(3-amino-4-fluoro-1H-indazol-5-yl)-3-methylphenyl)sulfonyl)-4,4-difluoropyrrolidin-2-yl)methanol

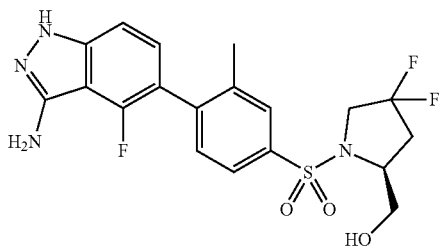 [SMILES: Cc1cc(S(=O)(=O)N2CC(F)(F)C[C@H]2CO)ccc1-c1ccc2[nH]nc(N)c2c1F]

The title compound was prepared in an analogous manner to Example 28, using 4-fluoro-5-(4,4,5,5-tetramethyl-1,3,2-dioxaborolan-2-yl)-1H-indazol-3-amine (Intermediate 7) in place of 4-chloro-5-(4,4,5,5-tetramethyl-1,3,2-dioxaborolan-2-yl)-1H-indazol-3-amine (Intermediate 5), with heating at 150° C. under microwave irradiation for 20 min. (UPLC-MS, METHOD B) $t_R$ 1.30 min; API-MS 441.2 [M+H]$^+$.

Example 45: 4-(3-amino-4-methyl-1H-indazol-5-yl)-N-((3R,4R)-4-hydroxytetrahydro-2H-pyran-3-yl)-3-methylbenzenesulfonamide

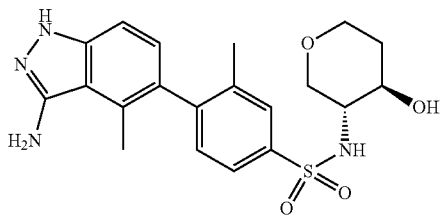 [SMILES: Cc1cc(S(=O)(=O)N[C@@H]2COCC[C@H]2O)ccc1-c1ccc2[nH]nc(N)c2c1C]

The title compound was prepared in an analogous manner to Example 1, using 4-bromo-N-((3R,4R)-4-hydroxytetrahydro-2H-pyran-3-yl)-3-methylbenzenesulfonamide (Intermediate 57) in place of 1-((4-bromo-3-chlorophenyl)sulfonyl)-3,3-dimethylazetidine (Intermediate 25). (UPLC-MS, METHOD B) $t_R$ 1.22 min; API-MS 417.2 [M+H]$^+$.

Example 46: (S)-(1-((4-(3-amino-4-fluoro-1H-indazol-5-yl)-3-chlorophenyl)sulfonyl)-4,4-difluoropyrrolidin-2-yl)methanol

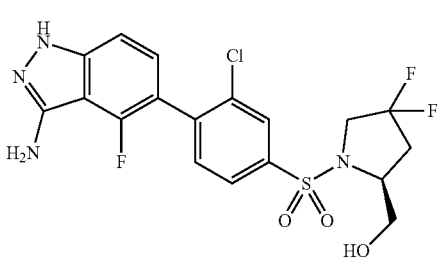 [SMILES: Nc1n[nH]c2ccc(-c3ccc(S(=O)(=O)N4CC(F)(F)C[C@H]4CO)cc3Cl)c(F)c12]

The title compound was prepared in an analogous manner to Example 28, using 4-fluoro-5-(4,4,5,5-tetramethyl-1,3,2-dioxaborolan-2-yl)-1H-indazol-3-amine (Intermediate 7) in place of 4-chloro-5-(4,4,5,5-tetramethyl-1,3,2-dioxaborolan-2-yl)-1H-indazol-3-amine (Intermediate 5), and using (S)-(1-((4-bromo-3-chlorophenyl)sulfonyl)-4,4-difluoropyrrolidin-2-yl)methanol (Intermediate 17) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.93 (s, 1H), 8.07 (d, J=1.9 Hz, 1H), 7.95-7.90 (m, 1H), 7.70 (d, J=8.1 Hz, 1H), 7.20-7.13 (m, 2H), 5.35 (s, 2H), 5.13 (t, J=5.7 Hz, 1H), 4.01-3.95 (m, 2H), 3.75 (ddd, J=23.3, 13.0, 7.0 Hz, 1H), 3.62 (t, J=5.2 Hz, 2H), 2.40 (ddt, J=18.9, 14.5, 7.3 Hz, 2H). (UPLC-MS, METHOD B) $t_R$ 1.32 min; API-MS 461.2 [M+H]$^+$.

Example 47: (S)-(1-((4-(3-amino-4-chloro-1H-indazol-5-yl)-3-fluorophenyl)sulfonyl)-4,4-difluoropyrrolidin-2-yl)methanol

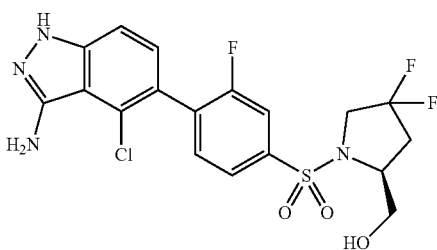 [SMILES: Nc1n[nH]c2ccc(-c3ccc(S(=O)(=O)N4CC(F)(F)C[C@H]4CO)cc3F)c(Cl)c12]

The title compound was prepared in an analogous manner to Example 28, using (S)-(1-((4-bromo-3-fluorophenyl)sulfonyl)-4,4-difluoropyrrolidin-2-yl)methanol (Intermediate 19) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 12.03 (s, 1H), 7.89 (dd, J=9.2, 1.8 Hz, 1H), 7.81 (dd, J=8.0, 1.8 Hz, 1H), 7.70-7.63 (m, 1H), 7.33 (d, J=8.5 Hz, 1H), 7.21 (d, J=8.5 Hz, 1H), 5.32 (s, 2H), 5.13 (t, J=5.7 Hz, 1H), 3.99-3.93 (m, 2H), 3.75 (ddd, J=23.0, 13.0, 7.1 Hz, 1H), 3.62 (t, J=5.1 Hz, 2H), 2.46-2.31 (m, 2H). (UPLC-MS, METHOD B) $t_R$ 1.31 min; API-MS 461.1 [M+H]$^+$.

Example 48: 4-(3-amino-4-methyl-1H-indazol-5-yl)-N-((1S,2R)-2-hydroxycyclopentyl)-3-methylbenzenesulfonamide

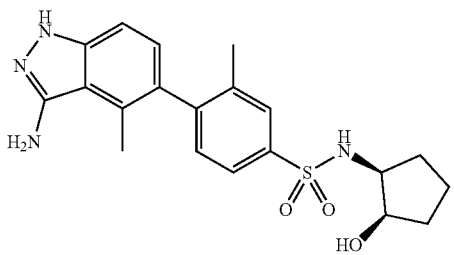 [SMILES: Cc1cc(S(=O)(=O)N[C@H]2CCC[C@H]2O)ccc1-c1ccc2[nH]nc(N)c2c1C]

The title compound was prepared in an analogous manner to Example 31, using 4-bromo-N-((1S,2R)-2-hydroxycyclopentyl)-3-methylbenzenesulfonamide (Intermediate 51) in place of 4-bromo-N-((1s,3s)-3-hydroxy-3-(trifluoromethyl)cyclobutyl)-3-methylbenzenesulfonamide (Intermediate 9). Heating was carried out with microwave irradiation. $^1$H NMR (400 MHz, DMSO-d6) δ 11.56 (s, 1H), 7.80-7.77 (m, 1H), 7.70 (dt, J=7.9, 2.4 Hz, 1H), 7.27 (d, J=8.0 Hz, 2H), 7.11 (d, J=8.5 Hz, 1H), 6.91 (d, J=8.5 Hz, 1H), 4.98 (s, 2H), 4.67 (d, J=4.0 Hz, 1H), 3.80 (dd, J=5.2, 3.3 Hz, 1H), 3.32-3.26 (m, 1H), 2.29 (s, 3H), 2.08 (s, 3H), 1.69-1.57 (m, 2H), 1.52-1.41 (m, 3H), 1.36 (td, J=12.1, 11.5, 7.1 Hz, 1H). (UPLC-MS, METHOD B) $t_R$ 1.28 min; API-MS 401.2 [M+H]$^+$.

Example 49: 4-(3-amino-4-methyl-1H-indazol-5-yl)-N-(3-ethyl-3-hydroxycyclobutyl)-3-methylbenzenesulfonamide

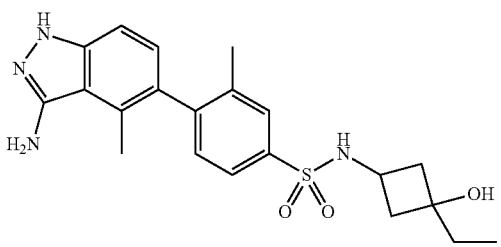 [SMILES: CCC1(O)CC(NS(=O)(=O)c2ccc(-c3ccc4[nH]nc(N)c4c3C)c(C)c2)C1]

The title compound was prepared in an analogous manner to Example 31, using 4-bromo-N-(3-ethyl-3-hydroxycyclobutyl)-3-methylbenzenesulfonamide (Intermediate 62) in place 4-bromo-N-((1s,3s)-3-hydroxy-3-(trifluoromethyl)cyclobutyl)-3-methylbenzenesulfonamide (Intermediate 9). (UPLC-MS, METHOD B) $t_R$ 1.32 min; API-MS 415.2 [M+H]$^+$.

Example 50: 4-(3-amino-4-methyl-1H-indazol-5-yl)-N-(3-cyclopropyl-3-hydroxycyclobutyl)-3-methylbenzenesulfonamide

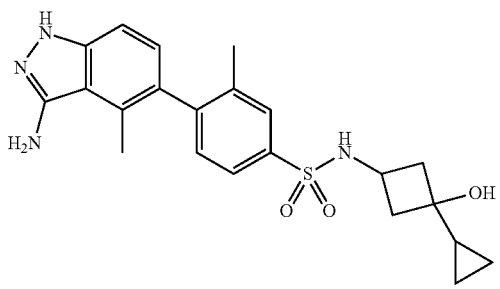 [SMILES: Cc1cc(S(=O)(=O)NC2CC(O)(C3CC3)C2)ccc1-c1ccc2[nH]nc(N)c2c1C]

The title compound was prepared in an analogous manner to Example 31, using 4-bromo-N-(3-cyclopropyl-3-hydroxycyclobutyl)-3-methylbenzenesulfonamide (Intermediate 61) in place of 4-bromo-N-((1s,3s)-3-hydroxy-3-(trifluoromethyl)cyclobutyl)-3-methylbenzenesulfonamide (Intermediate 9). (UPLC-MS, METHOD B) $t_R$ 1.33 min; API-MS 427.2 [M+H]$^+$.

Example 51: 4-(3-amino-4-methyl-1H-indazol-5-yl)-N-(3-benzyl-3-hydroxycyclobutyl)-3-methylbenzenesulfonamide

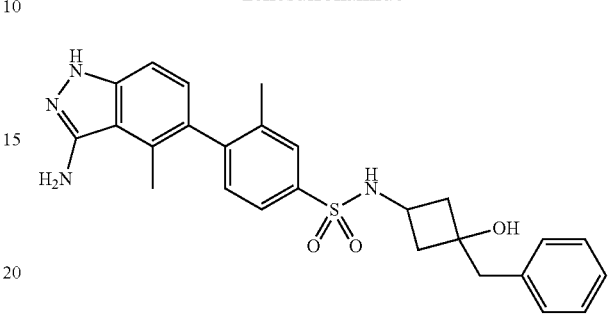

The title compound was prepared in an analogous manner to Example 31, using N-(3-benzyl-3-hydroxycyclobutyl)-4-bromo-3-methylbenzenesulfonamide (Intermediate 70) in place of 4-bromo-N-((1s,3s)-3-hydroxy-3-(trifluoromethyl)cyclobutyl)-3-methylbenzenesulfonamide (Intermediate 9). (UPLC-MS, METHOD B) $t_R$ 1.50 min; API-MS 477.2 [M+H]$^+$.

Example 52: 4-(3-amino-4-methyl-1H-indazol-5-yl)-N-(3-hydroxy-3-phenylcyclobutyl)-3-methylbenzenesulfonamide

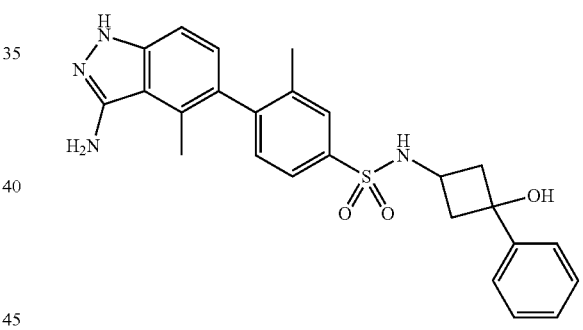

The title compound was prepared in an analogous manner to Example 31, using 4-bromo-N-(3-hydroxy-3-phenylcyclobutyl)-3-methylbenzenesulfonamide (Intermediate 64) in place 4-bromo-N-((1s,3s)-3-hydroxy-3-(trifluoromethyl)cyclobutyl)-3-methylbenzenesulfonamide (Intermediate 9). (UPLC-MS, METHOD B) $t_R$ 1.46 min; API-MS 463.2 [M+H]$^+$.

Example 53: (S)-(1-((4-(3-amino-4-chloro-1H-indazol-5-yl)-3-chlorophenyl)sulfonyl)-4,4-difluoropyrrolidin-2-yl)methanol

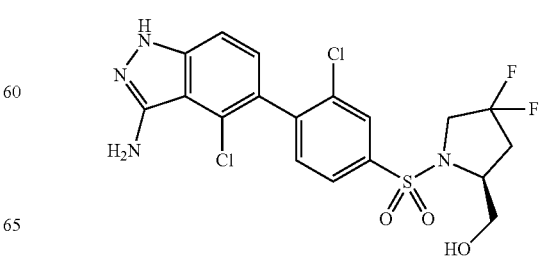

The title compound was prepared in an analogous manner to Example 28, using (S)-(1-((4-bromo-3-chlorophenyl)sulfonyl)-4,4-difluoropyrrolidin-2-yl)methanol (Intermediate 17) in place of (S)-(1-((4-bromo-3-methylphenyl)sulfonyl)pyrrolidin-2-yl)methanol (Intermediate 22), with heating at 150° C. under microwave irradiation for 20 min. ¹H NMR (400 MHz, DMSO-d6) δ 12.01 (s, 1H), 8.07 (d, J=1.9 Hz, 1H), 7.95-7.91 (m, 1H), 7.64 (dd, J=8.0, 1.1 Hz, 1H), 7.32 (d, J=8.5 Hz, 1H), 7.13 (dd, J=8.5, 0.8 Hz, 1H), 5.29 (s, 2H), 5.14 (t, J=5.7 Hz, 1H), 4.01-3.95 (m, 2H), 3.75 (ddd, J=23.5, 13.0, 6.9 Hz, 1H), 3.62 (t, J=5.1 Hz, 2H), 2.45-2.34 (m, 2H). (UPLC-MS, METHOD B) $t_R$ 1.35 min; API-MS 477.1 [M+H]⁺.

Example 54: (S)-(1-((4-(3-amino-4-chloro-1H-indazol-5-yl)-3-methylphenyl)sulfonyl)-4,4-difluoropyrrolidin-2-yl)methanol

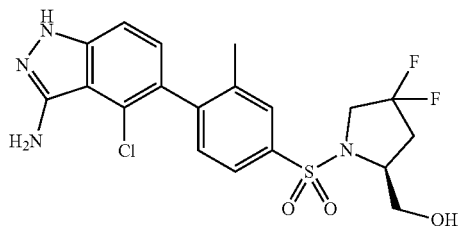 [SMILES: Cc1cc(S(=O)(=O)N2CC(F)(F)C[C@H]2CO)ccc1-c1ccc2[nH]nc(N)c2c1Cl]

The title compound was prepared in an analogous manner to Example 28, using (S)-(1-((4-bromo-3-methylphenyl)sulfonyl)-4,4-difluoropyrrolidin-2-yl)methanol (Intermediate 20) in place of (S)-(1-((4-bromo-3-methylphenyl)sulfonyl)pyrrolidin-2-yl)methanol (Intermediate 22), with heating at 150° C. under microwave irradiation for 30 min. (UPLC-MS, METHOD B) $t_R$ 1.42 min; API-MS 457.1 [M+H]⁺.

Example 55: 4-(3-amino-4-methyl-1H-indazol-5-yl)-3-chloro-N-((1s,3s)-3-hydroxy-3-(trifluoromethyl)cyclobutyl)benzenesulfonamide

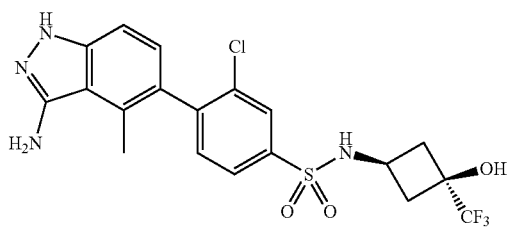 [SMILES: Cc1c(-c2ccc(S(=O)(=O)N[C@H]3C[C@](O)(C(F)(F)F)C3)cc2Cl)ccc2[nH]nc(N)c12]

The title compound was prepared in an analogous manner to Example 31, using 4-bromo-3-chloro-N-((1s,3s)-3-hydroxy-3-(trifluoromethyl)cyclobutyl)benzenesulfonamide (Intermediate 39) in place of 4-bromo-N-((1s,3s)-3-hydroxy-3-(trifluoromethyl)cyclobutyl)-3-methylbenzenesulfonamide (Intermediate 9), with heating at 150° C. under microwave irradiation for 30 min. ¹H NMR (400 MHz, DMSO-d6) δ 11.63 (s, 1H), 8.37 (d, J=8.3 Hz, 1H), 7.93 (d, J=1.9 Hz, 1H), 7.80 (dd, J=8.0, 1.9 Hz, 1H), 7.56 (d, J=8.0 Hz, 1H), 7.13 (d, J=8.5 Hz, 1H), 6.96 (d, J=8.6 Hz, 1H), 6.68 (s, 1H), 5.03 (s, 2H), 3.50-3.41 (m, 1H), 2.60-2.56 (m, 2H), 2.34 (s, 3H), 2.12-2.03 (m, 2H). (UPLC-MS, METHOD B) $t_R$ 1.28 min; API-MS 475.1 [M+H]⁺.

Example 56: (S)-(1-((4-(3-amino-4-methyl-1H-indazol-5-yl)-3-chlorophenyl)sulfonyl)-4,4-difluoropyrrolidin-2-yl)methanol

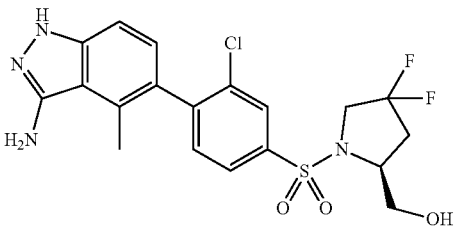 [SMILES: Cc1c(-c2ccc(S(=O)(=O)N3CC(F)(F)C[C@H]3CO)cc2Cl)ccc2[nH]nc(N)c12]

The title compound was prepared in an analogous manner to Example 31, using (S)-(1-((4-bromo-3-chlorophenyl)sulfonyl)-4,4-difluoropyrrolidin-2-yl)methanol (Intermediate 17) in place of 4-bromo-N-((1s,3s)-3-hydroxy-3-(trifluoromethyl)cyclobutyl)-3-methylbenzenesulfonamide (Intermediate 9), with heating at 150° C. under microwave irradiation for 30 min. ¹H NMR (400 MHz, DMSO-d6) δ 11.63 (s, 1H), 8.04 (dd, J=4.2, 1.9 Hz, 1H), 7.89 (ddd, J=8.0, 3.6, 1.9 Hz, 1H), 7.56 (d, J=8.0 Hz, 1H), 7.13 (d, J=8.5 Hz, 1H), 6.95 (d, J=8.5 Hz, 1H), 5.13 (t, J=5.7 Hz, 1H), 5.03 (s, 2H), 3.98-3.89 (m, 2H), 3.74 (ddd, J=24.0, 13.1, 6.9 Hz, 1H), 3.62 (t, J=5.2 Hz, 2H), 2.44-2.33 (m, 2H), 2.32 (d, J=1.2 Hz, 3H). (UPLC-MS, METHOD B) $t_R$ 1.40 min; API-MS 457.1 [M+H]⁺.

Example 57: 1-((4-(3-amino-4-methyl-1H-indazol-5-yl)-3-methylphenyl)sulfonyl)-3-methylpyrrolidin-3-ol

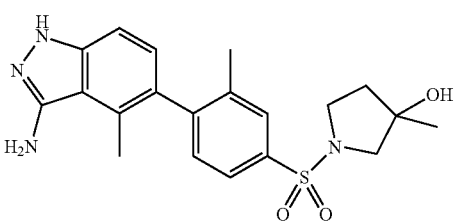 [SMILES: Cc1cc(S(=O)(=O)N2CCC(C)(O)C2)ccc1-c1ccc2[nH]nc(N)c2c1C]

The title compound was prepared in an analogous manner to Example 31, using 1-((4-bromo-3-methylphenyl)sulfonyl)-3-methylpyrrolidin-3-ol (Intermediate 32) in place of 4-bromo-N-((1s,3s)-3-hydroxy-3-(trifluoromethyl)cyclobutyl)-3-methylbenzenesulfonamide (Intermediate 9), with heating at 150° C. under microwave irradiation for 30 min. ¹NMR (400 MHz, DMSO-d6) δ 11.50 (s, 1H), 7.66 (s, 1H), 7.57 (dd, J=7.9, 1.8 Hz, 1H), 7.24 (d, J=7.9 Hz, 1H), 7.07-7.01 (m, 1H), 6.84 (d, J=8.5 Hz, 1H), 4.91 (s, 2H), 4.70 (s, 1H), 3.26-3.23 (m, 2H), 3.12-2.99 (m, 2H), 2.21 (s, 3H), 2.03 (s, 3H), 1.68 (dt, J=11.0, 5.2 Hz, 1H), 1.57 (dt, J=12.5, 8.6 Hz, 1H), 1.06 (s, 3H). (UPLC-MS, METHOD B) $t_R$ 1.32 min; API-MS 401.2 [M+H]⁺.

Example 58: 4-(3-amino-4-methyl-1H-indazol-5-yl)-N-((1S,2S)-2-hydroxy-2-methylcyclopentyl)-3-methylbenzenesulfonamide and Example 59

4-(3-amino-4-methyl-1H-indazol-5-yl)-N-((1S,2R)-2-hydroxy-2-methylcyclopentyl)-3-methylbenzenesulfonamide

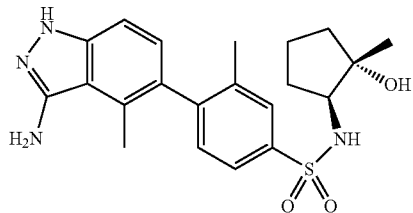

Example 58

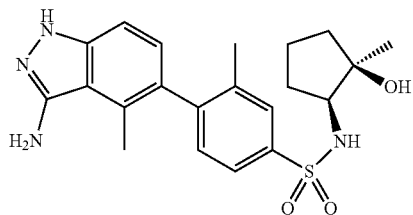

Example 59

Step 1: 4-bromo-3-methyl-N-(2-oxocyclopentyl)benzenesulfonamide

A solution of 4-bromo-N-((1S,2R)-2-hydroxycyclopentyl)-3-methylbenzenesulfonamide (Intermediate 51) (104 mg, 0.311 mmol) in DCM (3 mL) at RT was treated with Dess-Martin periodinane (198 mg, 0.467 mmol) and was stirred at RT for 16 h. The reaction mixture was concentrated onto celite and was purified by FCC to afford the title compound. (UPLC-MS, METHOD B) $t_R$ 1.63 min; API-MS 332.0 [M+H]$^+$.

Step 2: 4-bromo-N-((1S,2S)-2-hydroxy-2-methylcyclopentyl)-3-methylbenzenesulfonamide and 4-bromo-N-((1S,2R)-2-hydroxy-2-methylcyclopentyl)-3-methylbenzenesulfonamide (Diastereomer Mix)

A solution of 4-bromo-3-methyl-N-(2-oxocyclopentyl)benzenesulfonamide (81 mg, 0.24 mmol) in THF (24 mL) at 0° C. was treated with methylmagnesium bromide solution (3.0 M, 98 µl, 0.29 mmol) and was stirred at RT for 3 h. LCMS analysis showed product formation (masses as M−18 and M+23). The reaction mixture was quenched with sat. aq. ammonium chloride, diluted with DCM and passed through a phase separator. The DCM layer was concentrated and purified by FCC to afford 4-bromo-N-((1S,2R)-2-hydroxy-2-methylcyclopentyl)-3-methylbenzenesulfonamide (major) and 4-bromo-N-((1S,2S)-2-hydroxy-2-methylcyclopentyl)-3-methylbenzenesulfonamide (minor) as an inseparable mixture in an approximately 2:1 ratio. (UPLC-MS, METHOD B) $t_R$ 1.59 min (major) and 1.69 min (minor); API-MS 371.0 [M+Na]$^+$.

Step 3: 4-(3-amino-4-methyl-1H-indazol-5-yl)-N-((1S,2S)-2-hydroxy-2-methylcyclopentyl)-3-methylbenzenesulfonamide and 4-(3-amino-4-methyl-1H-indazol-5-yl)-N-((1S,2R)-2-hydroxy-2-methylcyclopentyl)-3-methylbenzenesulfonamide The title compounds were prepared in an analogous manner to Example 31, using the mixture of 4-bromo-N-((1S,2R)-2-hydroxy-2-methylcyclopentyl)-3-methylbenzenesulfonamide (major) and 4-bromo-N-((1S,2S)-2-hydroxy-2-methylcyclopentyl)-3-methylbenzenesulfonamide (minor) from Step 2 in place of 4-bromo-N-((1s,3s)-3-hydroxy-3-(trifluoromethyl)cyclobutyl)-3-methylbenzenesulfonamide (Intermediate 9), with heating at 150° C. under microwave irradiation for 30 min.

Example 58: 4-(3-amino-4-methyl-1H-indazol-5-yl)-N-((1S,2S)-2-hydroxy-2-methylcyclopentyl)-3-methylbenzenesulfonamide (minor product) $^1$H NMR (400 MHz, DMSO-d6) δ 11.56 (s, 1H), 7.80 (s, 1H), 7.70 (d, J=7.9 Hz, 1H), 7.46-7.41 (m, 1H), 7.26 (d, J=7.9 Hz, 1H), 7.11 (d, J=8.4 Hz, 1H), 6.90 (d, J=8.5 Hz, 1H), 4.97 (s, 2H), 4.32 (s, 1H), 3.09 (t, J=8.9 Hz, 1H), 2.27 (s, 3H), 2.11 (s, 1H), 2.07 (s, 3H), 1.58-1.54 (m, 2H), 1.48-1.46 (m, 2H), 1.38-1.30 (m, 1H), 1.04 (s, 3H). (UPLC-MS, METHOD B) $t_R$ 1.38 min; API-MS 415.2 [M+H]$^+$.

Example 59: 4-(3-amino-4-methyl-1H-indazol-5-yl)-N-((1S,2R)-2-hydroxy-2-methylcyclopentyl)-3-methylbenzenesulfonamide (major product) $^1$H NMR (400 MHz, DMSO-d6) δ 11.57 (s, 1H), 7.74 (s, 1H), 7.68-7.63 (m, 1H), 7.43 (d, J=9.0 Hz, 1H), 7.28 (d, J=7.9 Hz, 1H), 7.11 (d, J=8.5 Hz, 1H), 6.91 (d, J=8.5 Hz, 1H), 4.98 (s, 2H), 4.42 (s, 1H), 3.25 (q, J=8.0 Hz, 1H), 2.28 (s, 3H), 2.11 (s, 1H), 2.08 (s, 3H), 1.73 (dt, J=13.6, 7.3 Hz, 1H), 1.51 (s, 2H), 1.21-1.13 (m, 2H), 1.11 (s, 3H). (UPLC-MS, METHOD B) $t_R$ 1.29 min; API-MS 415.2 [M+H]$^+$.

Example 60: 1-((S)-1-((4-(3-amino-4-methyl-1H-indazol-5-yl)-3-methylphenyl)sulfonyl)pyrrolidin-2-yl)ethan-1-ol

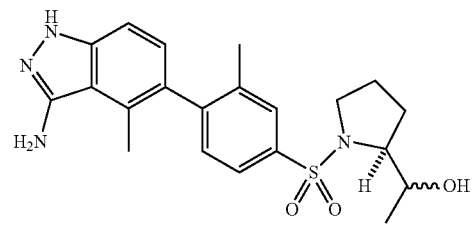 [SMILES: Cc1cc(S(=O)(=O)N2CCC[C@H]2C(C)O)ccc1-c1ccc2[nH]nc(N)c2c1C]

The title compound was prepared in an analogous manner to Example 31, using 1-((S)-1-((4-bromo-3-methylphenyl)sulfonyl)pyrrolidin-2-yl)ethan-1-ol (Intermediate 16) in place of 4-bromo-N-((1s,3s)-3-hydroxy-3-(trifluoromethyl)cyclobutyl)-3-methylbenzenesulfonamide (Intermediate 9), with heating at 150° C. under microwave irradiation for 30 min. $^1$H NMR (400 MHz, DMSO-d6) δ 11.58 (s, 1H), 7.77 (s, 1H), 7.68 (dd, J=7.9, 1.8 Hz, 1H), 7.33 (t, J=7.7 Hz, 1H), 7.12 (d, J=8.5 Hz, 1H), 6.92 (dd, J=8.5, 2.2 Hz, 1H), 4.99 (s, 2H), 4.73 (dd, J=6.9, 4.9 Hz, 1H), 3.92-3.81 (m, 1H), 3.51 (dt, J=8.1, 3.9 Hz, 1H), 3.31-3.22 (m, 2H), 2.28 (s, 3H), 2.11 (s, 3H), 1.94-1.65 (m, 2H), 1.39-1.22 (m, 2H), 1.11-1.05 (m, 3H). (UPLC-MS, METHOD B) $t_R$ 1.29 min; API-MS 415.2 [M+H]$^+$.

Example 61: (S)-(1-((4-(3-amino-4-fluoro-1H-indazol-5-yl)-3-fluorophenyl)sulfonyl)-4,4-difluoropyrrolidin-2-yl)methanol

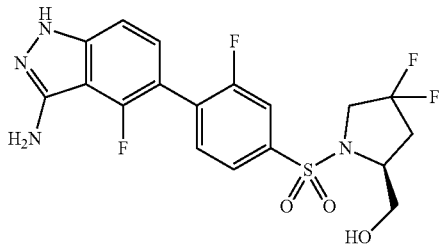

The title compound was prepared in an analogous manner to Example 28, using 4-fluoro-5-(4,4,5,5-tetramethyl-1,3,2-dioxaborolan-2-yl)-1H-indazol-3-amine (Intermediate 7) in place of 4-chloro-5-(4,4,5,5-tetramethyl-1,3,2-dioxaborolan-2-yl)-1H-indazol-3-amine (Intermediate 5), and using (S)-(1-((4-bromo-3-fluorophenyl)sulfonyl)-4,4-difluoropyrrolidin-2-yl)methanol (Intermediate 19) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.95 (s, 1H), 7.89 (dd, J=9.5, 1.7 Hz, 1H), 7.81 (dd, J=8.1, 1.8 Hz, 1H), 7.76-7.71 (m, 1H), 7.31-7.25 (m, 1H), 7.18 (d, J=8.6 Hz, 1H), 5.38 (s, 2H), 5.13 (t, J=5.7 Hz, 1H), 3.95 (s, 2H), 3.75 (ddd, J=20.3, 12.8, 7.2 Hz, 1H), 3.62 (t, J=5.1 Hz, 2H), 2.45-2.30 (m, 2H). (UPLC-MS, METHOD B) $t_R$ 1.29 min; API-MS 445.1 [M+H]$^+$.

Example 62: 1-((4-(3-amino-4-methyl-1H-indazol-5-yl)-3-methylphenyl)sulfonyl)-3-(trifluoromethyl)pyrrolidin-3-ol

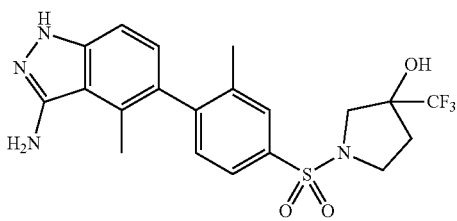 [SMILES: Cc1cc(S(=O)(=O)N2CCC(O)(C(F)(F)F)C2)ccc1-c1ccc2[nH]nc(N)c2c1C]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using 1-((4-bromo-3-methylphenyl)sulfonyl)-3-(trifluoromethyl)pyrrolidin-3-ol (Intermediate 27) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.57 (s, 1H), 7.78 (s, 1H), 7.68 (dt, J=7.9, 2.0 Hz, 1H), 7.34 (d, J=7.9 Hz, 1H), 7.12 (d, J=8.5 Hz, 1H), 6.90 (d, J=8.5 Hz, 1H), 6.52 (s, 1H), 4.98 (s, 2H), 3.55-3.49 (m, 1H), 3.47 (dd, J=11.4, 2.4 Hz, 1H), 3.33-3.28 (m, 2H), 2.27 (s, 3H), 2.11 (s, 3H), 2.00-1.92 (m, 2H). (UPLC-MS, METHOD B) $t_R$ 1.35 min; API-MS 455.2 [M+H]$^+$.

Example 63: 4-(3-amino-4-methyl-1H-indazol-5-yl)-N-(3,3-difluorocyclobutyl)-N,3-dimethylbenzenesulfonamide

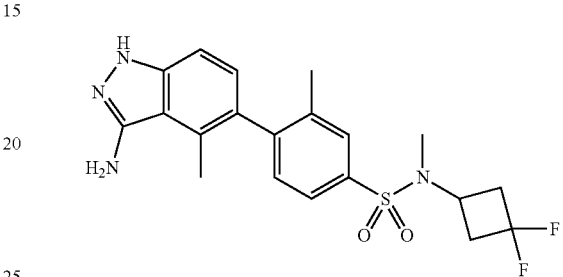

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using 4-bromo-N-(3,3-difluorocyclobutyl)-N,3-dimethylbenzenesulfonamide (Intermediate 60) in place of (S)-(1-((4-bromo-3-methylphenyl)sulfonyl)pyrrolidin-2-yl)methanol (Intermediate 22), with heating at 150° C. under microwave irradiation for 1 h. $^1$H NMR (400 MHz, DMSO-d6) δ 11.57 (s, 1H), 7.73 (d, J=1.7 Hz, 1H), 7.64 (dd, J=7.9, 1.7 Hz, 1H), 7.34 (d, J=8.0 Hz, 1H), 7.11 (d, J=8.5 Hz, 1H), 6.91 (d, J=8.5 Hz, 1H), 4.98 (s, 2H), 3.89 (tdd, J=8.0, 4.7, 1.4 Hz, 1H), 2.83-2.73 (m, 4H), 2.69 (s, 3H), 2.29 (s, 3H), 2.11 (s, 3H). (UPLC-MS, METHOD B) $t_R$ 1.44 min; API-MS 421.2 [M+H]$^+$.

Example 64: 4-(3-amino-4-chloro-1H-indazol-5-yl)-3-chloro-N-((1s,3s)-3-hydroxy-3-(trifluoromethyl)cyclobutyl)benzenesulfonamide

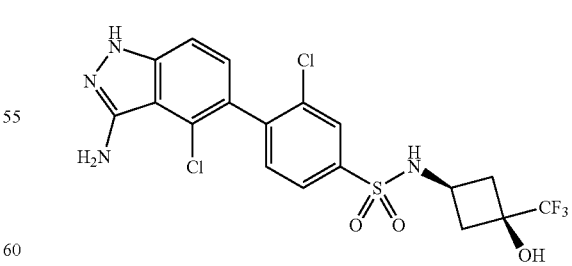

The title compound was prepared in an analogous manner to Example 28, using 4-bromo-3-chloro-N-((1s,3s)-3-hydroxy-3-(trifluoromethyl)cyclobutyl)benzenesulfonamide (Intermediate 39) in place 4-bromo-N-((1s,3s)-3-hydroxy-3-(trifluoromethyl)cyclobutyl)-3-methylbenzenesulfonamide (Intermediate 9), with heating at 150° C. under microwave irradiation for 20 min. $^1$H NMR (400 MHz, DMSO-d6) δ 12.01 (s, 1H), 8.40 (d, J=8.3 Hz, 1H), 7.95 (d, J=1.8 Hz, 1H), 7.83 (dd, J=8.0, 1.9 Hz, 1H), 7.63 (d, J=8.0 Hz, 1H), 7.31 (d, J=8.5 Hz, 1H), 7.15 (d, J=8.5 Hz, 1H), 6.68 (s, 1H), 5.29 (s, 2H), 3.44 (dt, J=16.4, 8.2 Hz, 1H), 2.57 (dd, J=12.9, 8.0 Hz, 2H), 2.13-2.02 (m, 2H). (UPLC-MS, METHOD B) $t_R$ 1.52 min; API-MS 495.0 [M+H]$^+$.

Example 65: 4-(3-amino-4-methoxy-1H-indazol-5-yl)-3-chloro-N-((1s,3s)-3-hydroxy-3-(trifluoromethyl)cyclobutyl)benzenesulfonamide

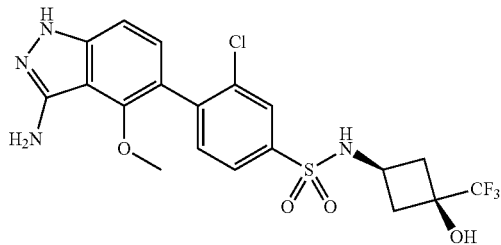 [SMILES: COc1c(-c2ccc(S(=O)(=O)N[C@H]3C[C@](O)(C(F)(F)F)C3)cc2Cl)ccc2[nH]nc(N)c12]

The title compound was prepared in an analogous manner to Example 28, using 4-methoxy-5-(4,4,5,5-tetramethyl-1,3,2-dioxaborolan-2-yl)-1H-indazol-3-amine (Intermediate 8) in place of 4-chloro-5-(4,4,5,5-tetramethyl-1,3,2-dioxaborolan-2-yl)-1H-indazol-3-amine (Intermediate 5), and using 4-bromo-3-chloro-N-((1s,3s)-3-hydroxy-3-(trifluoromethyl)cyclobutyl)benzenesulfonamide (Intermediate 39) in place of (S)-(1-((4-bromo-3-methylphenyl)sulfonyl)pyrrolidin-2-yl)methanol (Intermediate 22), with heating at 150° C. under microwave irradiation for 20 min. (UPLC-MS, METHOD B) $t_R$ 1.45 min; API-MS 491.1 [M+H]$^+$.

Example 66: 4-(3-amino-4-chloro-1H-indazol-5-yl)-N-(3,3-difluorocyclobutyl)-3-methylbenzenesulfonamide

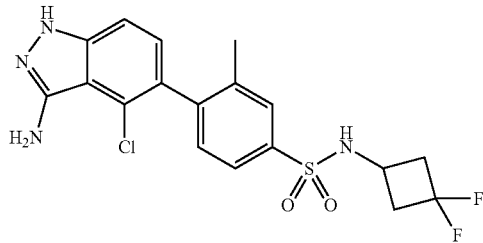 [SMILES: Cc1cc(S(=O)(=O)NC2CC(F)(F)C2)ccc1-c1ccc2[nH]nc(N)c2c1Cl]

The title compound was prepared in an analogous manner to Example 28, using 4-bromo-N-(3,3-difluorocyclobutyl)-3-methylbenzenesulfonamide (Intermediate 59) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.95 (s, 1H), 8.18 (d, J=7.6 Hz, 1H), 7.76 (d, J=1.6 Hz, 1H), 7.68 (dd, J=7.9, 1.6 Hz, 1H), 7.38 (d, J=8.0 Hz, 1H), 7.29 (d, J=8.5 Hz, 1H), 7.10 (d, J=8.5 Hz, 1H), 5.25 (s, 2H), 3.67-3.56 (m, 1H), 2.75 (tdd, J=14.5, 8.0, 3.9 Hz, 2H), 2.46-2.29 (m, 2H), 2.15 (s, 3H). (UPLC-MS, METHOD B) $t_R$ 1.53 min; API-MS 427.1 [M+H]$^+$.

Example 67: 4-(3-amino-4-chloro-1H-indazol-5-yl)-3-chloro-N-(3,3-difluorocyclobutyl)benzenesulfonamide

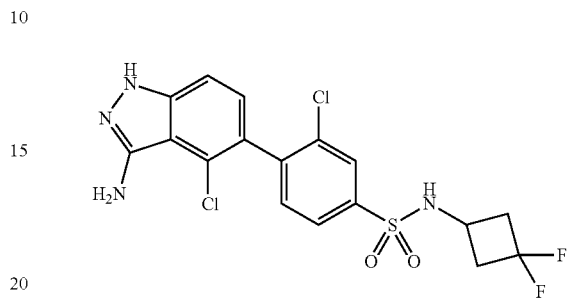

The title compound was prepared in an analogous manner to Example 28, using 4-bromo-N-(3,3-difluorocyclobutyl)-3-chlorobenzenesulfonamide (Intermediate 58) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 12.00 (s, 1H), 8.40 (d, J=7.4 Hz, 1H), 7.97-7.92 (m, 1H), 7.63 (d, J=8.0 Hz, 1H), 7.31 (d, J=8.5 Hz, 1H), 7.20-7.13 (m, 2H), 5.28 (s, 2H), 3.72-3.62 (m, 1H), 2.80 (tdd, J=13.3, 8.1, 5.5 Hz, 2H), 2.48-2.36 (m, 2H). (UPLC-MS, METHOD B) $t_R$ 1.55 min; API-MS 447.1 [M+H]$^+$.

Example 68: 4-(3-amino-4-methyl-1H-indazol-5-yl)-3-chloro-N-(3,3-difluorocyclobutyl)benzenesulfonamide

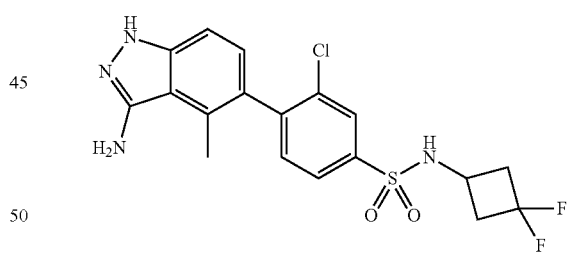

The title compound was prepared in an analogous manner to Example 31, using 4-bromo-N-(3,3-difluorocyclobutyl)-3-chlorobenzenesulfonamide (Intermediate 58) in place of 4-bromo-N-((1s,3s)-3-hydroxy-3-(trifluoromethyl)cyclobutyl)-3-methylbenzenesulfonamide (Intermediate 9), with heating under microwave irradiation at 150° C. for 30 min. $^1$H NMR (400 MHz, DMSO-d6) δ 11.95 (s, 1H), 8.18 (d, J=7.6 Hz, 1H), 7.76 (d, J=1.6 Hz, 1H), 7.68 (dd, J=7.9, 1.6 Hz, 1H), 7.38 (d, J=8.0 Hz, 1H), 7.29 (d, J=8.5 Hz, 1H), 7.10 (d, J=8.5 Hz, 1H), 5.25 (s, 2H), 3.67-3.56 (m, 1H), 2.75 (tdd, J=14.5, 8.0, 3.9 Hz, 2H), 2.46-2.29 (m, 2H), 2.15 (s, 3H). (UPLC-MS, METHOD B) $t_R$ 1.49 min; API-MS 427.1 [M+H]$^+$.

Example 69: 4-(3-amino-4-chloro-1H-indazol-5-yl)-3-chloro-N-((1R,2S)-2-hydroxycyclopentyl)benzenesulfonamide

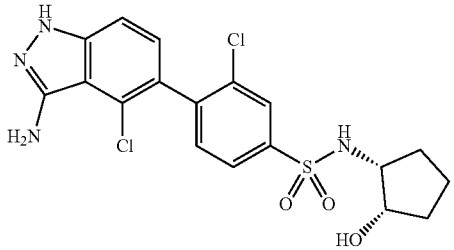

The title compound was prepared in an analogous manner to Example 28, using 4-bromo-3-chloro-N-((1R,2S)-2-hydroxycyclopentyl)benzenesulfonamide (Intermediate 38) in place of (S)-(1-((4-bromo-3-methylphenyl)sulfonyl)pyrrolidin-2-yl)methanol (Intermediate 22), and heating at 150° C. with heating under microwave irradiation for 30 min. Following FCC, the product was additionally purified by reverse phase HPLC (METHOD 1), followed by passage of the resulting product through a Varian Inc. stratosphere SPE PL-HCO3 MP resin, to provide the title compound. (UPLC-MS, METHOD B) $t_R$ 1.39 min; API-MS 441.0 [M+H]$^+$.

Example 70: 4-(3-amino-4-methoxy-1H-indazol-5-yl)-N-((1s,3s)-3-hydroxy-3-(trifluoromethyl)cyclobutyl)-3-methylbenzenesulfonamide

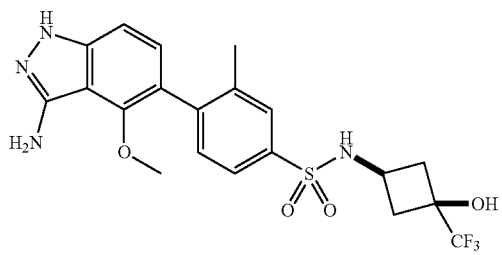

The title compound was prepared in an analogous manner to Example 28, using 4-methoxy-5-(4,4,5,5-tetramethyl-1,3,2-dioxaborolan-2-yl)-1H-indazol-3-amine (Intermediate 8) in place of 4-chloro-5-(4,4,5,5-tetramethyl-1,3,2-dioxaborolan-2-yl)-1H-indazol-3-amine (Intermediate 5), and using 4-bromo-N-((1s,3s)-3-hydroxy-3-(trifluoromethyl)cyclobutyl)-3-methylbenzenesulfonamide (Intermediate 9) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.62 (s, 1H), 8.15 (d, J=8.5 Hz, 1H), 7.73 (d, J=1.7 Hz, 1H), 7.66 (dd, J=8.0, 1.7 Hz, 1H), 7.46 (d, J=8.0 Hz, 1H), 7.06-6.98 (m, 2H), 6.63 (s, 1H), 5.12 (s, 2H), 3.43-3.39 (m, 1H), 3.38 (s, 3H), 2.49-2.45 (m, 2H), 2.23 (s, 3H), 2.09-2.00 (m, 2H). (UPLC-MS, METHOD B) $t_R$ 1.28 min; API-MS 471.0 [M+H]$^+$.

Example 71: 4-(3-amino-4-fluoro-1H-indazol-5-yl)-N-((1s,3s)-3-hydroxy-3-(trifluoromethyl)cyclobutyl)-3-methylbenzenesulfonamide

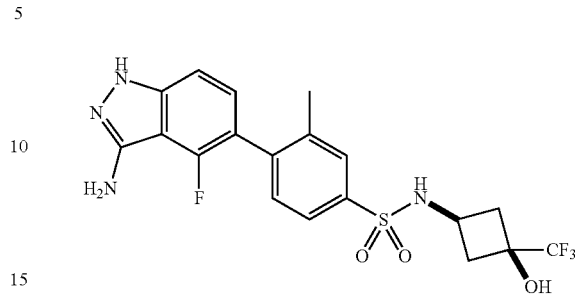

The title compound was prepared in an analogous manner to Example 28, using 4-fluoro-5-(4,4,5,5-tetramethyl-1,3,2-dioxaborolan-2-yl)-1H-indazol-3-amine (Intermediate 7) in place of 4-chloro-5-(4,4,5,5-tetramethyl-1,3,2-dioxaborolan-2-yl)-1H-indazol-3-amine (Intermediate 5), and using 4-bromo-N-((1s,3s)-3-hydroxy-3-(trifluoromethyl)cyclobutyl)-3-methylbenzenesulfonamide (Intermediate 9) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, Acetonitrile-d3) δ 10.10 (s, 1H), 7.80 (d, J=2.0 Hz, 1H), 7.72 (dd, J=8.0, 1.7 Hz, 1H), 7.47 (d, J=8.0 Hz, 1H), 7.23-7.17 (m, 2H), 6.14 (d, J=8.6 Hz, 1H), 4.59 (s, 2H), 4.42 (s, 1H), 3.64-3.52 (m, 1H), 2.75-2.67 (m, 2H), 2.30 (s, 3H), 2.10 (dddd, J=12.7, 6.5, 2.7, 1.3 Hz, 2H). (UPLC-MS, METHOD B) $t_R$ 1.37 min; API-MS 459.0 [M+H]$^+$.

Example 72: 4-(3-amino-4-fluoro-1H-indazol-5-yl)-3-chloro-N-((1s,3s)-3-hydroxy-3-(trifluoromethyl)cyclobutyl)benzenesulfonamide

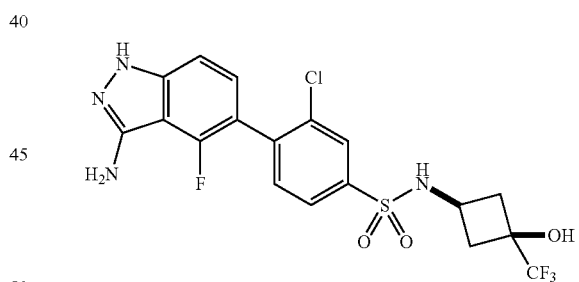

The title compound was prepared in an analogous manner to Example 28, using 4-fluoro-5-(4,4,5,5-tetramethyl-1,3,2-dioxaborolan-2-yl)-1H-indazol-3-amine (Intermediate 7) in place of 4-chloro-5-(4,4,5,5-tetramethyl-1,3,2-dioxaborolan-2-yl)-1H-indazol-3-amine (Intermediate 5), and using 4-bromo-3-chloro-N-((1s,3s)-3-hydroxy-3-(trifluoromethyl)cyclobutyl)benzenesulfonamide (Intermediate 39)) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.93 (s, 1H), 8.40 (d, J=8.2 Hz, 1H), 7.95 (d, J=1.9 Hz, 1H), 7.83 (dd, J=8.1, 1.9 Hz, 1H), 7.69 (d, J=8.1 Hz, 1H), 7.21-7.12 (m, 2H), 6.68 (s, 1H), 5.35 (s, 2H), 3.48-3.41 (m, 1H), 2.58 (ddd, J=11.1, 8.1, 3.0 Hz, 2H), 2.11-2.03 (m, 2H). (UPLC-MS, METHOD B) $t_R$ 1.39 min; API-MS 479.1 [M+H]$^+$.

Example 73: 4-(3-amino-4-methoxy-1H-indazol-5-yl)-N-((1R,2S)-2-hydroxycyclopentyl)-3-methylbenzenesulfonamide

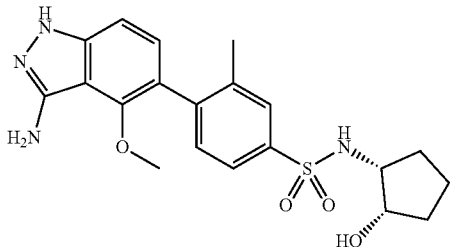 [SMILES: COc1c(-c2ccc(S(=O)(=O)N[C@@H]3CCC[C@@H]3O)cc2C)ccc2[nH]nc(N)c12]

The title compound was prepared in an analogous manner to Example 28, using 4-methoxy-5-(4,4,5,5-tetramethyl-1,3,2-dioxaborolan-2-yl)-1H-indazol-3-amine (Intermediate 8) in place of 4-chloro-5-(4,4,5,5-tetramethyl-1,3,2-dioxaborolan-2-yl)-1H-indazol-3-amine (Intermediate 5), and using: 4-bromo-3-methyl-N-((1R,2S)-2-hydroxycyclopentyl)benzenesulfonamide (Intermediate 41) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.61 (s, 1H), 7.79 (d, J=1.5 Hz, 1H), 7.71 (dd, J=8.0, 1.7 Hz, 1H), 7.41 (d, J=8.0 Hz, 1H), 7.26 (d, J=8.3 Hz, 1H), 7.05-6.98 (m, 2H), 5.11 (s, 2H), 4.66 (d, J=4.0 Hz, 1H), 3.79 (dt, J=4.3, 2.2 Hz, 1H), 3.39 (s, 3H), 3.32-3.29 (m, 1H), 2.21 (s, 3H), 1.61 (tt, J=13.0, 6.1 Hz, 2H), 1.52-1.38 (m, 3H), 1.38-1.31 (m, 1H). (UPLC-MS, METHOD B) $t_R$ 1.23 min; API-MS 417.2 [M+H]$^+$.

Example 74: 4-(3-amino-4-methoxy-1H-indazol-5-yl)-3-chloro-N-(1R,2S)-2-hydroxycyclopentyl)benzenesulfonamide

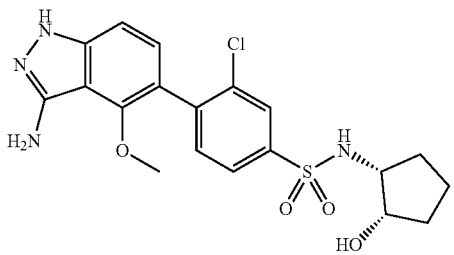 [SMILES: COc1c(-c2ccc(S(=O)(=O)N[C@@H]3CCC[C@@H]3O)cc2Cl)ccc2[nH]nc(N)c12]

The title compound was prepared in an analogous manner to Example 28, using 4-methoxy-5-(4,4,5,5-tetramethyl-1,3,2-dioxaborolan-2-yl)-1H-indazol-3-amine (Intermediate 8) in place of 4-chloro-5-(4,4,5,5-tetramethyl-1,3,2-dioxaborolan-2-yl)-1H-indazol-3-amine (Intermediate 5), and using 4-bromo-3-chloro-N-((1R,2S)-2-hydroxycyclopentyl)benzenesulfonamide (Intermediate 38) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.68 (s, 1H), 8.02 (d, J=1.8 Hz, 1H), 7.85 (dd, J=8.0, 1.9 Hz, 1H), 7.62 (d, J=8.0 Hz, 1H), 7.57 (d, J=8.5 Hz, 1H), 7.05 (s, 2H), 5.14 (s, 2H), 4.74 (d, J=4.0 Hz, 1H), 3.84-3.77 (m, 1H), 3.46 (s, 3H), 3.39-3.36 (m, 1H), 1.70-1.55 (m, 2H), 1.53-1.32 (m, 4H). (UPLC-MS, METHOD B) $t_R$ 1.29 min; API-MS 437.1 [M+H]$^+$.

Example 75: 4-(3-amino-4-fluoro-1H-indazol-5-yl)-N-((1R,2S)-2-hydroxycyclopentyl)-3-methylbenzenesulfonamide

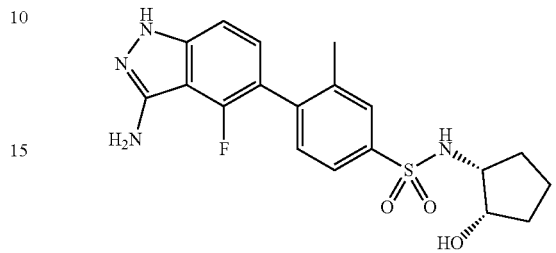

The title compound was prepared in an analogous manner to Example 28, using 4-fluoro-5-(4,4,5,5-tetramethyl-1,3,2-dioxaborolan-2-yl)-1H-indazol-3-amine (Intermediate 7) in place of 4-chloro-5-(4,4,5,5-tetramethyl-1,3,2-dioxaborolan-2-yl)-1H-indazol-3-amine (Intermediate 5), and using 4-bromo-3-methyl-N-((1R,2S)-2-hydroxycyclopentyl)benzenesulfonamide (Intermediate 41) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.86 (s, 1H), 7.81 (d, J=1.7 Hz, 1H), 7.73 (dd, J=8.0, 1.7 Hz, 1H), 7.41 (d, J=8.0 Hz, 1H), 7.32 (d, J=8.1 Hz, 1H), 7.15-7.09 (m, 2H), 5.29 (s, 2H), 4.68 (d, J=4.0 Hz, 1H), 3.81 (tq, J=4.3, 2.1 Hz, 1H), 3.31-3.27 (m, 1H), 2.24 (s, 3H), 1.63 (dtt, J=12.9, 8.2, 3.6 Hz, 2H), 1.47 (ddd, J=14.2, 8.7, 5.1 Hz, 3H), 1.41-1.31 (m, 1H). (UPLC-MS, METHOD B) $t_R$ 1.27 min; API-MS 405.1 [M+H]$^+$.

Example 76: 4-(3-amino-4-fluoro-1H-indazol-5-yl)-3-chloro-N-((1R,2S)-2-hydroxycyclopentyl)benzenesulfonamide

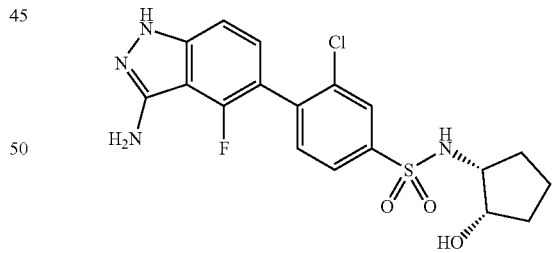

The title compound was prepared in an analogous manner to Example 28, using 4-fluoro-5-(4,4,5,5-tetramethyl-1,3,2-dioxaborolan-2-yl)-1H-indazol-3-amine (Intermediate 7) in place of 4-chloro-5-(4,4,5,5-tetramethyl-1,3,2-dioxaborolan-2-yl)-1H-indazol-3-amine (Intermediate 5), and using 4-bromo-3-chloro-N-((1R,2S)-2-hydroxycyclopentyl)benzenesulfonamide (Intermediate 38) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.91 (s, 1H), 8.04 (d, J=1.8 Hz, 1H), 7.87 (dd, J=8.0, 1.9 Hz, 1H), 7.66-7.59 (m, 2H), 7.20-7.13 (m, 2H), 5.34 (s, 2H), 4.75 (d, J=4.0 Hz, 1H), 3.85-3.77 (m, 1H), 3.40-3.32 (m, 1H), 1.63 (qt, J=7.5, 3.4 Hz, 2H), 1.52-1.41 (m, 3H), 1.41-1.34 (m, 1H). (UPLC-MS, METHOD B) $t_R$ 1.31 min; API-MS 425.1 [M+H]$^+$.

Example 77: 5-(4-(((3,3-difluoropyrrolidin-1-yl)sulfonyl)-2-methylphenyl)-4-methyl-1H-indazol-3-amine

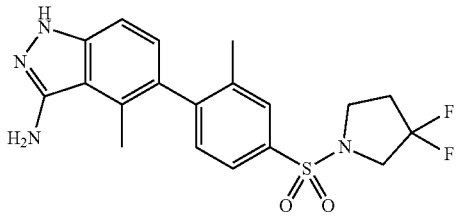 [SMILES: Cc1cc(S(=O)(=O)N2CCC(F)(F)C2)ccc1-c1ccc2[nH]nc(N)c2c1C]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using 1-((4-bromo-3-methylphenyl)sulfonyl)-3,3-difluoropyrrolidine (Intermediate 30) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.58 (s, 1H), 7.80 (d, J=1.6 Hz, 1H), 7.70 (dd, J=7.9, 1.7 Hz, 1H), 7.36 (d, J=8.0 Hz, 1H), 7.12 (d, J=8.5 Hz, 1H), 6.92 (d, J=8.5 Hz, 1H), 4.99 (s, 2H), 3.65 (t, J=13.0 Hz, 2H), 3.43 (t, J=7.3 Hz, 2H), 2.37 (tt, J=14.3, 7.3 Hz, 2H), 2.28 (s, 3H), 2.12 (s, 3H). (UPLC-MS, METHOD B) $t_R$ 1.84 min; API-MS 407.2 [M+H]$^+$.

Example 78: 5-(4-((3,3-difluoroazetidin-1-yl)sulfonyl)-2-methylphenyl)-4-methyl-1H-indazol-3-amine

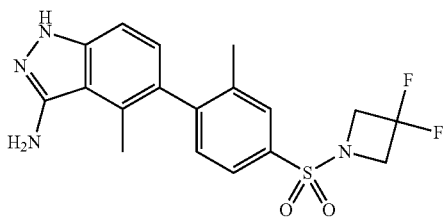 [SMILES: Cc1cc(S(=O)(=O)N2CC(F)(F)C2)ccc1-c1ccc2[nH]nc(N)c2c1C]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using 1-((4-bromo-3-methylphenyl)sulfonyl)-3,3-difluoroazetidine (Intermediate 28) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.59 (s, 1H), 7.86 (d, J=1.7 Hz, 1H), 7.76 (dd, J=7.9, 1.7 Hz, 1H), 7.42 (d, J=8.0 Hz, 1H), 7.13 (d, J=8.5 Hz, 1H), 6.93 (d, J=8.5 Hz, 1H), 5.00 (s, 2H), 4.32 (t, J=12.8 Hz, 4H), 2.29 (s, 3H), 2.14 (s, 3H). (UPLC-MS, METHOD B) $t_R$ 1.78 min; API-MS 393.1 [M+H]$^+$.

Example 79: 5-(4-(((3,3-difluoropiperidin-1-yl)sulfonyl)-2-methylphenyl)-4-methyl-1H-indazol-3-amine

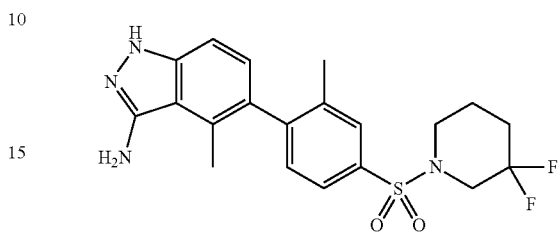

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using 1-((4-bromo-3-methylphenyl)sulfonyl)-3,3-difluoropiperidine (Intermediate 29) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.58 (s, 1H), 7.74 (d, J=1.7 Hz, 1H), 7.64 (dd, J=7.9, 1.7 Hz, 1H), 7.35 (d, J=8.0 Hz, 1H), 7.12 (d, J=8.5 Hz, 1H), 6.91 (d, J=8.5 Hz, 1H), 4.99 (s, 2H), 3.40-3.34 (m, 2H), 3.12-3.05 (m, 2H), 2.31 (s, 3H), 2.12 (s, 3H), 1.99 (dq, J=13.8, 6.8, 6.2 Hz, 2H), 1.74 (p, J=6.5 Hz, 2H). (UPLC-MS, METHOD B) $t_R$ 1.88 min; API-MS 421.2 [M+H]$^+$.

Example 80: 5-(4-(((4,4-difluoropiperidin-1-yl)sulfonyl)-2-methylphenyl)-4-methyl-1H-indazol-3-amine

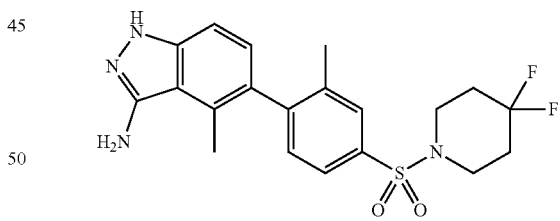

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using 1-((4-bromo-3-methylphenyl)sulfonyl)-4,4-difluoropiperidine (Intermediate 33) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.58 (s, 1H), 7.73 (d, J=1.6 Hz, 1H), 7.64 (dd, J=7.9, 1.8 Hz, 1H), 7.37 (d, J=8.0 Hz, 1H), 7.12 (d, J=8.5 Hz, 1H), 6.94 (d, J=8.5 Hz, 1H), 4.99 (s, 2H), 3.19-3.10 (m, 4H), 2.29 (s, 3H), 2.15-2.03 (m, 7H). (UPLC-MS, METHOD B) $t_R$ 1.88 min; API-MS 421.2 [M+H]$^+$.

Example 81: (S)-1-((4-(3-amino-4-methyl-1H-indazol-5-yl)-3-methylphenyl)sulfonyl)-4,4-difluoropyrrolidine-2-carboxamide

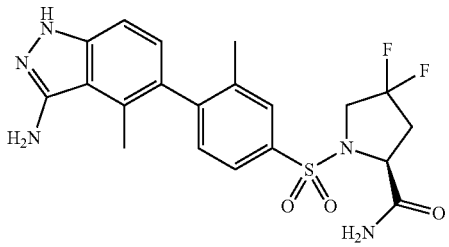 [SMILES: Cc1cc(S(=O)(=O)N2CC(F)(F)C[C@H]2C(N)=O)ccc1-c1ccc2[nH]nc(N)c2c1C]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using (S)-1-((4-bromo-3-methylphenyl)sulfonyl)-4,4-difluoropyrrolidine-2-carboxamide (Intermediate 23) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.58 (s, 1H), 7.86 (d, J=1.6 Hz, 1H), 7.76 (dd, J=7.9, 1.8 Hz, 1H), 7.65 (s, 1H), 7.39 (s, 1H), 7.36-7.32 (m, 1H), 7.13 (d, J=8.5 Hz, 1H), 6.91 (d, J=8.5 Hz, 1H), 4.99 (s, 2H), 4.33-4.26 (m, 1H), 3.86 (dd, J=13.4, 8.1 Hz, 2H), 2.48-2.32 (m, 2H), 2.28 (d, J=1.1 Hz, 3H), 2.12 (s, 3H). (UPLC-MS, METHOD B) $t_R$ 1.53 min; API-MS 450.2 [M+H]$^+$.

Example 82: Meso-5-(4-(((3R,4S)-3,4-difluoropyrrolidin-1-yl)sulfonyl)-2-methylphenyl)-4-methyl-1H-indazol-3-amine

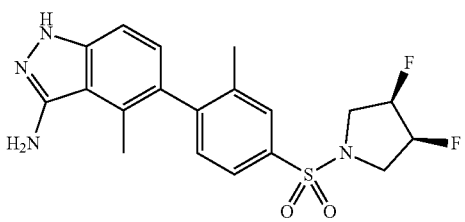 [SMILES: Cc1cc(S(=O)(=O)N2C[C@@H](F)[C@@H](F)C2)ccc1-c1ccc2[nH]nc(N)c2c1C]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using meso-(3R,4S)-1-((4-bromo-3-methylphenyl)sulfonyl)-3,4-difluoropyrrolidine (Intermediate 11) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.58 (s, 1H), 7.79 (d, J=1.7 Hz, 1H), 7.70 (dd, J=7.9, 1.7 Hz, 1H), 7.35 (d, J=8.0 Hz, 1H), 7.12 (d, J=8.5 Hz, 1H), 6.91 (d, J=8.5 Hz, 1H), 5.33-5.23 (m, 1H), 5.17 (dt, J=12.5, 4.5 Hz, 1H), 4.99 (s, 2H), 3.67 (ddd, J=21.2, 11.5, 5.4 Hz, 2H), 3.49-3.35 (m, 2H), 2.28 (s, 3H), 2.12 (s, 3H). (UPLC-MS, METHOD B) $t_R$ 1.64 min; API-MS 407.2 [M+H]$^+$.

Example 83: 4-(3-amino-4-methyl-1H-indazol-5-yl)-N-((1s,3s)-3-hydroxy-3-(trifluoromethyl)cyclobutyl)-N,3-dimethylbenzenesulfonamide

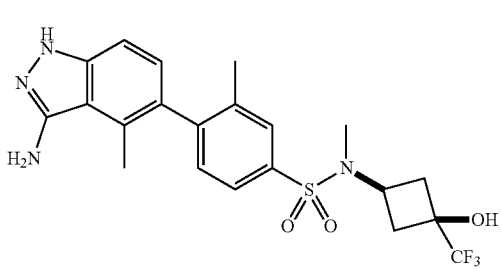

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using 4-bromo-N-((1s,3s)-3-hydroxy-3-(trifluoromethyl)cyclobutyl)-N,3-dimethylbenzenesulfonamide (Intermediate 63) in place of (S)-(1-((4-bromo-3-methylphenyl)sulfonyl)pyrrolidin-2-yl)methanol (Intermediate 22), with heating at 150° C. under microwave irradiation for 30 min. $^1$H NMR (400 MHz, DMSO-d6) δ 11.57 (s, 1H), 7.69 (d, J=1.7 Hz, 1H), 7.60 (dd, J=7.9, 1.7 Hz, 1H), 7.34 (d, J=8.0 Hz, 1H), 7.11 (d, J=8.5 Hz, 1H), 6.91 (d, J=8.5 Hz, 1H), 6.71 (s, 1H), 4.98 (s, 2H), 3.77 (p, J=8.4 Hz, 1H), 2.71 (s, 3H), 2.60-2.52 (m, 2H), 2.36-2.28 (m, 2H), 2.27 (s, 3H), 2.10 (s, 3H). (UPLC-MS, METHOD B) $t_R$ 1.37 min; API-MS 469.2 [M+H]$^+$.

Example 84: 4-(3-amino-4-methyl-1H-indazol-5-yl)-N-((1R,2S)-2-hydroxycyclopentyl)-N,3-dimethylbenzenesulfonamide

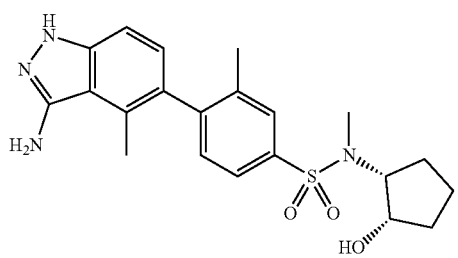 [SMILES: Cc1cc(S(=O)(=O)N(C)[C@@H]2CCC[C@@H]2O)ccc1-c1ccc2[nH]nc(N)c2c1C]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using 4-bromo-N-((1R,2S)-2-hydroxycyclopentyl)-N,3-dimethylbenzenesulfonamide (Intermediate 47) in place of (S)-(1-((4-bromo-3-methylphenyl)sulfonyl)pyrrolidin-2-yl)methanol (Intermediate 22), with heating at 150° C. under microwave irradiation for 20 min. $^1$H NMR (400 MHz, DMSO-d6) δ 11.57 (s, 1H), 7.73 (s, 1H), 7.63 (d, J=7.9 Hz, 1H), 7.30 (d, J=8.0 Hz, 1H), 7.11 (d, J=8.5 Hz, 1H), 6.92 (d, J=8.5 Hz, 1H), 4.99 (s, 2H), 4.83 (d, J=4.1 Hz, 1H), 4.02 (q, J=3.7, 3.2 Hz, 1H), 3.83 (ddt, J=12.2, 7.7, 4.1 Hz, 1H), 2.88 (d, J=1.5 Hz, 3H), 2.29 (s, 3H), 2.10 (s, 3H), 1.70 (dtd, J=16.6, 13.0, 12.2, 8.0 Hz, 3H), 1.44 (dd, J=12.9, 3.6 Hz, 2H), 1.28-1.20 (m, 1H). (UPLC-MS, METHOD B) $t_R$ 1.29 min; API-MS 415.3 [M+H]⁺.

Example 85: (S)-(1-((4-(3-amino-4-methoxy-1H-indazol-5-yl)-3-methylphenyl)sulfonyl)-4,4-difluoropyrrolidin-2-yl)methanol

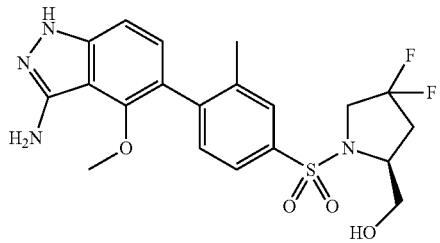 [SMILES: COc1c(-c2ccc(S(=O)(=O)N3CC(F)(F)C[C@H]3CO)cc2C)ccc2[nH]nc(N)c12]

The title compound was prepared in an analogous manner to Example 28, using 4-methoxy-5-(4,4,5,5-tetramethyl-1,3,2-dioxaborolan-2-yl)-1H-indazol-3-amine (Intermediate 8) in place of 4-chloro-5-(4,4,5,5-tetramethyl-1,3,2-dioxaborolan-2-yl)-1H-indazol-3-amine (Intermediate 5), and using (S)-(1-((4-bromo-3-methylphenyl)sulfonyl)-4,4-difluoropyrrolidin-2-yl)methanol (Intermediate 20) in place of (S)-(1-((4-bromo-3-methylphenyl)sulfonyl)pyrrolidin-2-yl)methanol (Intermediate 22), with heating at 150° C. under microwave irradiation for 20 min. ¹H NMR (400 MHz, DMSO-d6) δ 11.62 (s, 1H), 7.82 (d, J=1.6 Hz, 1H), 7.73 (dd, J=8.0, 1.8 Hz, 1H), 7.48 (d, J=8.0 Hz, 1H), 7.01 (q, J=8.5 Hz, 2H), 5.12 (s, 2H), 5.10 (d, J=5.7 Hz, 1H), 3.92-3.77 (m, 2H), 3.77-3.67 (m, 1H), 3.60 (dp, J=10.9, 6.1 Hz, 2H), 3.35 (s, 3H), 2.46-2.25 (m, 2H), 2.24 (s, 3H). (UPLC-MS, METHOD B) $t_R$ 1.27 min; API-MS 453.2 [M+H]⁺.

Example 86: (S)-(1-((4-(3-amino-4-methoxy-1H-indazol-5-yl)-3-chlorophenyl)sulfonyl)-4,4-difluoropyrrolidin-2-yl)methanol

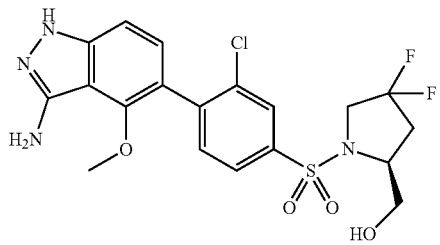 [SMILES: COc1c(-c2ccc(S(=O)(=O)N3CC(F)(F)C[C@H]3CO)cc2Cl)ccc2[nH]nc(N)c12]

The title compound was prepared in an analogous manner to Example 28, using 4-methoxy-5-(4,4,5,5-tetramethyl-1,3,2-dioxaborolan-2-yl)-1H-indazol-3-amine (Intermediate 8) in place of 4-chloro-5-(4,4,5,5-tetramethyl-1,3,2-dioxaborolan-2-yl)-1H-indazol-3-amine (Intermediate 5), and using (S)-(1-((4-bromo-3-chlorophenyl)sulfonyl)-4,4-difluoropyrrolidin-2-yl)methanol (Intermediate 17) in place of (S)-(1-((4-bromo-3-methylphenyl)sulfonyl)pyrrolidin-2-yl)methanol (Intermediate 22), with heating at 150° C. under microwave irradiation for 20 min. ¹H NMR (400 MHz, DMSO-d6) δ 11.68 (s, 1H), 8.04 (d, J=1.9 Hz, 1H), 7.89 (dd, J=8.1, 1.9 Hz, 1H), 7.67 (d, J=8.1 Hz, 1H), 7.04 (d, J=0.9 Hz, 2H), 5.17-5.13 (m, 2H), 5.12 (d, J=5.7 Hz, 1H), 3.99-3.91 (m, 2H), 3.75 (dq, J=17.6, 6.5 Hz, 1H), 3.62 (t, J=5.1 Hz, 2H), 3.43 (s, 3H), 2.36 (dddd, J=20.5, 16.6, 13.2, 7.1 Hz, 2H). (UPLC-MS, METHOD B) $t_R$ 1.29 min; API-MS 473.2 [M+H]⁺.

Example 87: ((2S,4R)-1-((4-(3-amino-4-methyl-1H-indazol-5-yl)-3-methylphenyl)sulfonyl)-4-fluoropyrrolidin-2-yl)methanol

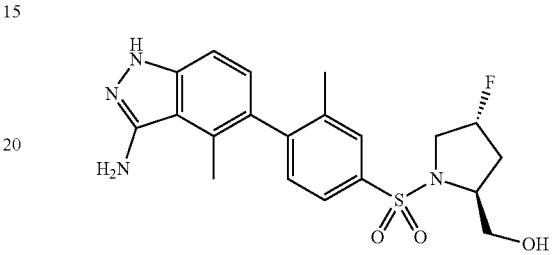

The title compound was prepared in an analogous manner to Example 31, using ((2S,4R)-1-((4-bromo-3-methylphenyl)sulfonyl)-4-fluoropyrrolidin-2-yl)methanol (Intermediate 71) in place of 4-bromo-N-((1s,3s)-3-hydroxy-3-(trifluoromethyl)cyclobutyl)-3-methylbenzenesulfonamide (Intermediate 9), with heating under microwave irradiation. (UPLC-MS, METHOD B) $t_R$ 1.20 min; API-MS 419.2 [M+H]⁺.

Example 88: (R)-(1-((4-(3-amino-4-methyl-1H-indazol-5-yl)-3-methylphenyl)sulfonyl)-4,4-difluoropyrrolidin-2-yl)methanol

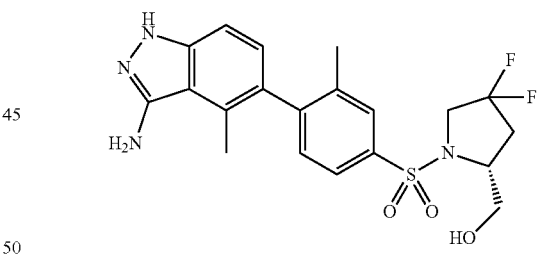

The title compound was prepared in an analogous manner to Example 31, using (R)-(1-((4-bromo-3-methylphenyl)sulfonyl)-4,4-difluoropyrrolidin-2-yl)methanol (Intermediate 72) in place of 4-bromo-N-((1s,3s)-3-hydroxy-3-(trifluoromethyl)cyclobutyl)-3-methylbenzenesulfonamide (Intermediate 9), with heating under microwave irradiation. Purification by FCC followed by crystallization from iPrOH/water (7:1) gave the title compound as a beige solid. ¹H NMR (500 MHz, DMSO-d6) δ 11.55 (s, 1H), 7.82 (dd, J=3.8, 1.9 Hz, 1H), 7.72 (ddd, J=7.9, 3.9, 2.2 Hz, 1H), 7.33 (d, J=8.0 Hz, 1H), 7.12 (d, J=8.2 Hz, 1H), 6.90 (d, J=8.5 Hz, 1H), 5.08 (td, J=5.7, 1.1 Hz, 1H), 4.96 (s, 2H), 3.95-3.87 (m, 1H), 3.87-3.78 (m, 1H), 3.78-3.67 (m, 1H), 3.67-3.56 (m, 2H), 2.44-2.33 (m, 1H), 2.33-2.22 (m, 1H), 2.27 (s, 3H), 2.10 (s, 3H). (UPLC-MS, METHOD B) $t_R$ 1.29 min; API-MS 437.2 [M+H]⁺.

Example 89: (S)-(1-((4-(3-amino-4-methyl-1H-indazol-5-yl)-3,5-difluorophenyl)sulfonyl)-4,4-difluoropyrrolidin-2-yl)methanol

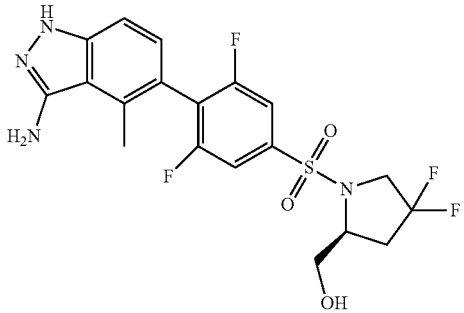 [SMILES: Cc1c(-c2c(F)cc(S(=O)(=O)N3CC(F)(F)C[C@H]3CO)cc2F)ccc2[nH]nc(N)c12]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using S)-(1-((4-bromo-3,5-difluorophenyl)sulfonyl)-4,4-difluoropyrrolidin-2-yl)methanol (Intermediate 69) in place of (S)-(1-((4-bromo-3-methylphenyl)sulfonyl)pyrrolidin-2-yl)methanol (Intermediate 22). $^1$H NMR (400 MHz, Methanol-d4) δ 7.70-7.62 (m, 2H), 7.22 (d, J=8.6 Hz, 1H), 7.12 (d, J=8.7 Hz, 1H), 4.06-3.68 (m, 4H), 2.47 (s, 3H), 2.40 (ddd, J=22.8, 10.6, 5.3 Hz, 2H), 1.36 (s, 1H). (UPLC-MS, METHOD B) $t_R$ 1.38 min; API-MS 459.1 [M+H]$^+$.

Example 90: (S)-(1-((4-(3-amino-4-methyl-1H-indazol-5-yl)-2-fluorophenyl)sulfonyl)-4,4-difluoropyrrolidin-2-yl)methanol

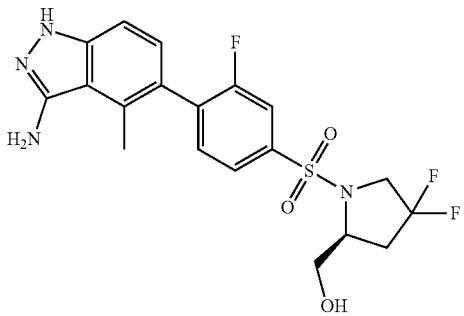 [SMILES: Cc1c(-c2ccc(S(=O)(=O)N3CC(F)(F)C[C@H]3CO)cc2F)ccc2[nH]nc(N)c12]

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using (S)-(1-((4-bromo-2-fluorophenyl)sulfonyl)-4,4-difluoropyrrolidin-2-yl)methanol (Intermediate 68) in place of (S)-(1-((4-bromo-3-methylphenyl)sulfonyl)pyrrolidin-2-yl)methanol (Intermediate 22). $^1$H NMR (400 MHz, Methanol-d$_4$) δ 7.96 (dd, J=8.2, 7.5 Hz, 1H), 7.37 (t, J=1.9 Hz, 1H), 7.35 (dd, J=5.5, 1.5 Hz, 1H), 7.21 (s, 2H), 4.19-4.12 (m, 1H), 3.99-3.85 (m, 1H), 3.84-3.66 (m, 3H), 2.62 (s, 3H), 2.57-2.37 (m, 2H). (UPLC-MS, METHOD B) $t_R$1.37 min; API-MS 441.1 [M+H]$^+$.

Example 91: (S)-(1-((4-(3-amino-4-methyl-1H-indazol-5-yl)-2-methylphenyl)sulfonyl)-4,4-difluoropyrrolidin-2-yl)methanol

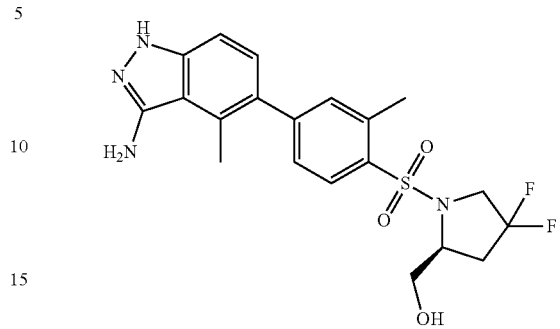

The title compound was prepared in an analogous manner to Example 28, using 4-methyl-5-(4,4,5,5-tetramethyl-1,3,2-dioxaborolan-2-yl)-1H-indazol-3-amine (Intermediate 6) in place of 4-chloro-5-(4,4,5,5-tetramethyl-1,3,2-dioxaborolan-2-yl)-1H-indazol-3-amine (Intermediate 5), and using (S)-(1-((4-bromo-2-methylphenyl)sulfonyl)-4,4-difluoropyrrolidin-2-yl)methanol (Intermediate 67) in place of (S)-(1-((4-bromo-3-methylphenyl)sulfonyl)pyrrolidin-2-yl)methanol (Intermediate 22). $^1$H NMR (400 MHz, Methanol-d$_4$) δ 8.01 (d, J=8.1 Hz, 1H), 7.39 (s, 1H), 7.36 (dd, J=8.2, 1.5 Hz, 1H), 7.18 (s, 2H), 4.22-4.13 (m, 1H), 3.89 (td, J=12.9, 7.7 Hz, 1H), 3.74-3.57 (m, 3H), 2.70 (s, 3H), 2.59 (s, 3H), 2.58-2.45 (m, 2H). (UPLC-MS, METHOD B) $t_R$ 1.41 min; API-MS 437.1 [M+H]$^+$.

Example 92: ((2S,4S)-1-((4-(3-amino-4-methyl-1H-indazol-5-yl)-3-methylphenyl)sulfonyl)-4-fluoropyrrolidin-2-yl)methanol

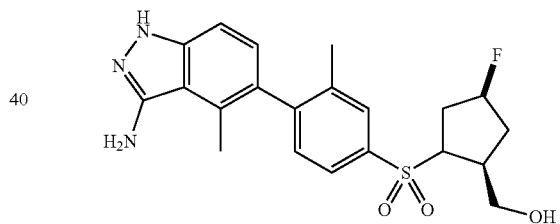

The title compound was prepared in an analogous manner to Example 31, using ((2S,4S)-1-((4-bromo-3-methylphenyl)sulfonyl)-4-fluoropyrrolidin-2-yl)methanol (Intermediate 10) in place of 4-bromo-N-((1s,3s)-3-hydroxy-3-(trifluoromethyl)cyclobutyl)-3-methylbenzenesulfonamide (Intermediate 9), with heating under microwave irradiation. $^1$H NMR (400 MHz, DMSO-d6) δ 11.57 (s, 1H), 7.76 (s, 1H), 7.67 (d, J=7.9 Hz, 1H), 7.34 (d, J=8.0 Hz, 1H), 7.11 (d, J=8.5 Hz, 1H), 6.91 (dd, J=8.5, 0.8 Hz, 1H), 5.23 (dt, J=53.2, 3.8 Hz, 1H), 4.98 (s, 2H), 4.95 (d, J=5.8 Hz, 1H), 3.71 (tq, J=9.5, 4.8 Hz, 2H), 3.66-3.55 (m, 1H), 3.37-3.33 (m, 2H), 2.29 (s, 3H), 2.26-2.15 (m, 1H), 2.11 (s, 3H), 1.73 (dtd, J=42.8, 9.9, 4.9 Hz, 1H). (UPLC-MS, METHOD B) $t_R$ 1.22 min; API-MS 419.2 [M+H]$^+$.

Example 93—In Vitro, Ex Vivo and In Vivo Assays (A) SCX-LUC In Vitro Assay

Scleraxis (Scx) is a tendon cell specific transcription factor. Based on the literature Scx appears to act early in the tendon cell differentiation pathway. A 1.5 kb stretch of genomic sequence upstream of the Scx coding region was cloned into the pGreenFire1 lentiviral reporter construct. This construct was used to make a stable line in TT-D6 immortalized cells that expresses Luciferase upon Scx transcriptional activation.

To determine transcriptional activation of Scleraxis (Scx) gene after treatment with the compounds of the invention, a mouse immortalized TT-D6 Scx-luciferase (ScxL) cell line was first seeded in a white, solid bottom 384 well plate (Greiner, cat#789163-G) in 50 ul media (Alpha MEM, 10% FBS, 1% pen-strep; Gibco, cat#12571048 and 15140122) supplemented with 1 ng/ml TGFß1 (PeproTech, cat#100-21) at a density of 6,000 cells/well. Cells were then treated with a serial dilution (1:3) of the compounds of the invention or DMSO alone for four days at 37° C. After the incubation period, media was removed and 20 ul Bright-Glo Reagent (Promega, cat #E2620) was added to the wells. Immediately, luciferase luminescence was read on a SprectraMax M5E plate reader with 50 ms integration.

The results are shown in the table below.

(B) Ex Vivo Assays

Tenogenic differentiation was measured ex vivo looking at mRNA levels for both tenogenic and extracellular matrix genes. Both Scleraxis (Scx) and Tenomodulin (Tnmd) genes have been shown to be enriched in tendon cells and associated with tenogenesis while an increase in tendon collagen type I (Col1a2) is secondary to tenogenic differentiation and is necessary for proper healing.

To determine ex vivo gene expression changes after stimulation with compounds of the invention, tendon fascicles were first removed from approximately 2-3 month old male Sprague Dawley rat tails. The tendon fascicles were washed in Hank's Balanced Salt Solution (HBSS, Hyclone, GE cat# SH30268.01) before being cut into 2.5 cm length pieces. Next, two tendon fascicle pieces were placed per well in a 48 well tissue culture plate containing 1 ml of Mesenchymal Stem Cell Growth Media (MSCGM, Lonza, cat# PT-3001) with serial dilutions (1:2) of compounds or DMSO alone. Tendon fascicles were then stimulated at 37° C. for four days in a cell culture incubator. RNA was isolated after the incubation period from the tendon fascicles using the RNeasy 96 Kit (Qiagen, cat#74181). cDNA was then synthesized from the RNA using Quanta's qScript Supermix (VWR, cat#101414-106) and thermocycler protocol: 25° C. for 5 minutes, 42° C. for 45 minutes, 85° C. for 5 minutes, hold at 4° C. Using SYBR green (Roche, cat#04707516001), qPCR reactions were carried out in a Roche Lightcycler 480 II (Software version: 1.5.0 SP3, Roche cat#05015243001) using the following cycling protocol: preincubation for 10 minutes at 95° C. followed by 45 amplification cycles of 10 seconds at 95° C., 10 seconds at 60° C. and 20 seconds at 72° C. Finally, gene expression data was calculated by using the delta-delta Ct method using the average of 3 housekeeping genes (Gadph, B-actin and 36b4).

Primer Sequences

| Gene name | Forward primer | Reverse primer |
|---|---|---|
| Gadph | ATC ACC ATC TTC CAG GAG CGA (SEQ ID NO: 1) | AGC CTT CTC CAT GGT GGT GAA (SEQ ID NO: 7) |
| 36b4 | GAT GCC CAG GGA AGA CAG (SEQ ID NO: 2) | CAC AAT GAA GCA TTT TGG GTA G (SEQ ID NO: 8) |
| Beta-actin | GCT CCT CCT GAG CGC AAG (SEQ ID NO: 3) | CAT CTG CTG GAA GGT GGA CA (SEQ ID NO: 9) |
| Scleraxis | CCC AAA CAG ATC TGC ACC TT (SEQ ID NO: 4) | TCT GTC ACG GTC TTT GCT CA (SEQ ID NO: 10) |
| Tenomodulin | TGG ATC AAT CCC ACT CTA ATA GC (SEQ ID NO: 5) | TCG CTG GTA GGA AAG TGA AGA (SEQ ID NO: 11) |
| Collagen type 1 (Col1a2) | CCT GGC TCT CGA GGT GAA C (SEQ ID NO: 6) | CAA TGC CCA GAG GAC CAG (SEQ ID NO: 12) |

The results are shown in the table below (Table 3) and show that compounds of the invention For Scx-Luc assay, $EC_{50}$ values were obtained using luciferase luminescence read on a SprectraMax M5E plate reader.

For ex vivo assays, $EC_{50}$ calculations were done using delta-delta Ct values for each gene calculated using the average of 3 housekeeping genes.

TABLE 3

| Example | Scx-Luc ($EC_{50}$ μM) | Ex vivo Scx ($EC_{50}$ μM) | Ex vivo Tnmd ($EC_{50}$ μM) | Ex vivo Col1a2 ($EC_{50}$ μM) |
|---|---|---|---|---|
| 1 | 0.773 | n.d. | n.d. | n.d. |
| 2 | 0.908 | n.d. | n.d. | n.d. |
| 3 | 2.831 | n.d. | n.d. | n.d. |
| 4 | 0.511 | 1.638 | 0.513 | 1.551 |
| 5 | 0.275 | 3.625 | 1.601 | 2.628 |
| 6 | 4.412 | n.d. | n.d. | n.d. |
| 7 | 2.016 | 5.348 | 0.463 | 3.312 |
| 8 | 3.600 | n.d. | n.d. | n.d. |
| 9 | 4.962 | n.d. | n.d. | n.d. |
| 10 | 1.791 | n.d. | n.d. | n.d. |
| 11 | 4.130 | n.d. | n.d. | n.d. |
| 12 | 2.214 | 1.725 | 10.000 | 10.000 |
| 13 | 2.333 | n.d. | n.d. | n.d. |
| 14 | 3.919 | 7.277 | 6.968 | 2.642 |
| 15 | 3.052 | n.d. | n.d. | n.d. |
| 16 | 0.638 | 1.752 | 0.447 | 0.557 |
| 17 | 4.803 | n.d. | n.d. | n.d. |
| 18 | 0.468 | 2.521 | 1.060 | 2.533 |
| 19 | 0.431 | 10.000 | 10.000 | 10.000 |
| 20 | 0.723 | n.d. | n.d. | n.d. |
| 21 | 1.264 | 3.695 | 6.642 | 5.318 |
| 22 | 0.879 | n.d. | n.d. | n.d. |
| 23 | 1.855 | n.d. | n.d. | n.d. |
| 24 | 0.366 | n.d. | n.d. | n.d. |
| 25 | 0.606 | n.d. | n.d. | n.d. |
| 26 | 0.745 | n.d. | n.d. | n.d. |
| 27 | 1.349 | n.d. | n.d. | n.d. |
| 28 | 0.436 | n.d. | n.d. | n.d. |
| 29 | 0.277 | n.d. | n.d. | n.d. |
| 30 | 0.752 | n.d. | n.d. | n.d. |
| 31 | 0.126 | 5.539 | 3.769 | 4.178 |
| 32 | 0.518 | 5.557 | 6.100 | 4.593 |
| 33 | 0.17 | n.d. | n.d. | n.d. |
| 34 | 0.614 | 1.542 | 0.078 | 5.918 |
| 35 | 1.519 | n.d. | n.d. | n.d. |
| 36 | 0.806 | n.d. | n.d. | n.d. |
| 37 | 0.227 | 0.996 | 1.685 | 1.816 |
| 38 | 2.035 | n.d. | n.d. | n.d. |
| 39 | 0.362 | n.d. | n.d. | n.d. |
| 40 | 0.988 | 2.692 | 2.916 | 1.825 |
| 41 | 1.329 | n.d. | n.d. | n.d. |
| 42 | 0.814 | n.d. | n.d. | n.d. |
| 43 | 0.696 | 3.373 | 4.874 | 3.448 |

TABLE 3-continued

| Example | Scx-Luc (EC$_{50}$ μM) | Ex vivo Scx (EC$_{50}$ μM) | Ex vivo Tnmd (EC$_{50}$ μM) | Ex vivo Col1a2 (EC$_{50}$ μM) |
|---|---|---|---|---|
| 44 | 1.187 | n.d. | n.d. | n.d. |
| 45 | 1.251 | 4.439 | 2.855 | 2.411 |
| 46 | 1.055 | n.d. | n.d. | n.d. |
| 47 | 0.986 | n.d. | n.d. | n.d. |
| 48 | 0.854 | n.d. | n.d. | n.d. |
| 49 | 0.852 | 3.038 | 2.777 | 2.232 |
| 50 | 1.293 | 3.263 | 7.385 | 2.006 |
| 51 | 1.583 | 6.984 | 6.796 | 6.388 |
| 52 | 0.578 | n.d. | n.d. | n.d. |
| 53 | 0.740 | n.d. | n.d. | n.d. |
| 54 | 0.242 | 3.802 | 0.706 | 4.415 |
| 55 | 0.228 | 3.144 | 5.501 | 3.498 |
| 56 | 0.764 | n.d. | n.d. | n.d. |
| 57 | 2.707 | n.d. | n.d. | n.d. |
| 58 | 1.332 | n.d. | n.d. | n.d. |
| 59 | 3.319 | n.d. | n.d. | n.d. |
| 60 | 1.606 | n.d. | n.d. | n.d. |
| 61 | 1.498 | n.d. | n.d. | n.d. |
| 62 | 0.630 | n.d. | n.d. | n.d. |
| 63 | 0.222 | 1.384 | 5.405 | 1.789 |
| 64 | 0.474 | n.d. | n.d. | n.d. |
| 65 | 1.223 | n.d. | n.d. | n.d. |
| 66 | 1.076 | n.d. | n.d. | n.d. |
| 67 | 0.535 | n.d. | n.d. | n.d. |
| 68 | 1.863 | n.d. | n.d. | n.d. |
| 69 | 0.148 | 1.047 | 3.843 | 1.484 |
| 70 | 0.282 | n.d. | n.d. | n.d. |
| 71 | 0.108 | n.d. | n.d. | n.d. |
| 72 | 0.177 | n.d. | n.d. | n.d. |
| 73 | 0.632 | 5.231 | 6.508 | 3.766 |
| 74 | 0.286 | n.d. | n.d. | n.d. |
| 75 | 0.359 | n.d. | n.d. | n.d. |
| 76 | 0.171 | n.d. | n.d. | n.d. |
| 77 | 0.692 | n.d. | n.d. | n.d. |
| 78 | 2.098 | 4.568 | 1.887 | 1.164 |
| 79 | 1.519 | n.d. | n.d. | n.d. |
| 80 | 2.534 | n.d. | n.d. | n.d. |
| 81 | 0.372 | n.d. | n.d. | n.d. |
| 82 | 0.524 | n.d. | n.d. | n.d. |
| 83 | 0.467 | n.d. | n.d. | n.d. |
| 84 | 1.688 | n.d. | n.d. | n.d. |
| 85 | 1.793 | n.d. | n.d. | n.d. |
| 86 | 0.731 | n.d. | n.d. | n.d. |
| 87 | 0.288 | n.d. | n.d. | n.d. |
| 88 | 0.22 | n.d. | n.d. | n.d. |
| 89 | 0.554 | n.d. | n.d. | n.d. |
| 90 | 1.245 | n.d. | n.d. | n.d. |
| 91 | 2.911 | n.d. | n.d. | n.d. |
| 92 | 1.010 | n.d. | n.d. | n.d. |

The compounds 4-(3-amino-4-methyl-1H-indazol-5-yl)-3-methyl-N-(1-methylpiperidin-4-yl)benzenesulfonamide and (3S,4S)-1-((4-(3-amino-4-methyl-1H-indazol-5-yl)-3-methylphenyl)sulfonyl)-4-fluoropyrrolidin-3-ol showed an EC$_{50}$>10 uM in the assays described above.

The data shown in the table above show that the compounds of the invention have activity as inducers of scleraxis, tenomodulin and collagen type I (col1a2) suggesting that the compounds are useful in the treatment of tendon and/or ligament injuries.

(C) In Vivo Assay

Animals were treated 3 days post-surgery with 1 mg of compound of example 32 in 10 ul of vehicle delivered by injection under the skin in the peri-tendinous region. Tendons were harvested 25 days post-treatment. Strong Alcian blue staining could be seen in the lesion in the vehicle treated group which is typical of endochondral tissue forming which further ossifies with time. Treatment with the compound of example 32 was able to counter some of the improper healing caused by aberrant differentiation towards the chondrogenic and osteogenic lineages. Definiens Tissue Studio software was used for quantitative image analysis of the Alcian blue positive area. Serial step sections encompassing 2 mm of the lesion were used for quantification.

| n = 5 per group | Endochondral ossification readout Alcian Blue positive (mm$^2$/section) | |
|---|---|---|
| | Mean | SD |
| Vehicle only | 40.27 | 12.5 |
| Treated | 25.09 | 10.55 |

The results in the table above suggest that compounds of the invention are useful in the treatment of tendon and/or ligament injuries by preventing improper healing caused by aberrant extracellular matrix deposition visualized by endochondral bone formation at the injury site.

(D) Ex Vivo Fascicle Assay:

Sample Preparation

Tail from skeletal mature rat (Sprague Dawley, female, 30-50 weeks old) was removed and kept on ice. Approximately 40 mm long segment was cut from the mid-portion of the tail. Rat tail fascicles (n=12) were carefully extracted from the segment. Fascicles were then randomly selected into three groups, fresh (n=4), vehicle (n=4) and (S)-(1-((4-(3-amino-4-methyl-1H-indazol-5-yl)-3-methylphenyl)sulfonyl)-4,4-difluoropyrrolidin-2-yl)methanol (Test Compound A hereinafter) treated (n=4). Biomechanical properties were measure immediately after extraction for the fresh group. Samples of the vehicle and Test Compound A groups were placed into 6 well plates (2 fascicles/well) in 2 ml/well of serum free tissue culture medium consisting of DMEM/F12 (Gibco®, catalogue number: 31331093), N2 supplement (1× concentration, Gibco®, catalogue number: 17502048), ascorbic acid (300 ug/ml, Wako catalogue number: 013-10641) and Pen-strep (1%, Gibco®, catalogue number: 15140122). For the Test Compound group, 1 uM Test Compound A was added to the wells. Equal amount of DMSO was added to the vehicle group. Both groups were incubated at 37° C. for 4 weeks. Media were refreshed once per week.

Mechanical Testing

Samples were clamped for mechanical testing using a standard uniaxial material testing machine (ElectroPuls E3000, 50N load-cell, Instron, US) in a custom environmental testing chamber filled with PBS. Samples were preloaded to a position where crimp (macroscopic fascicle waviness) disappeared and initial length (L0) based on grip-to-grip distance was recorded. Images of the fascicle were taken from orthogonal perspectives using two telecentric lenses (FABRIMEX T80 1.0 L, Fabrimex AG, Switzerland) to characterize the ellipsoidal cross-sectional area of each specimen. Samples were ramped to failure at a constant strain rate of 0.025% L0/s. Sample lengths and corresponding forces were recorded to calculate engineering stress and strain. Young's moduli were calculated from the linear region of the stress-strain curves. Failure stress was obtained at the point where maximum stress was reached.

Figure 1B:
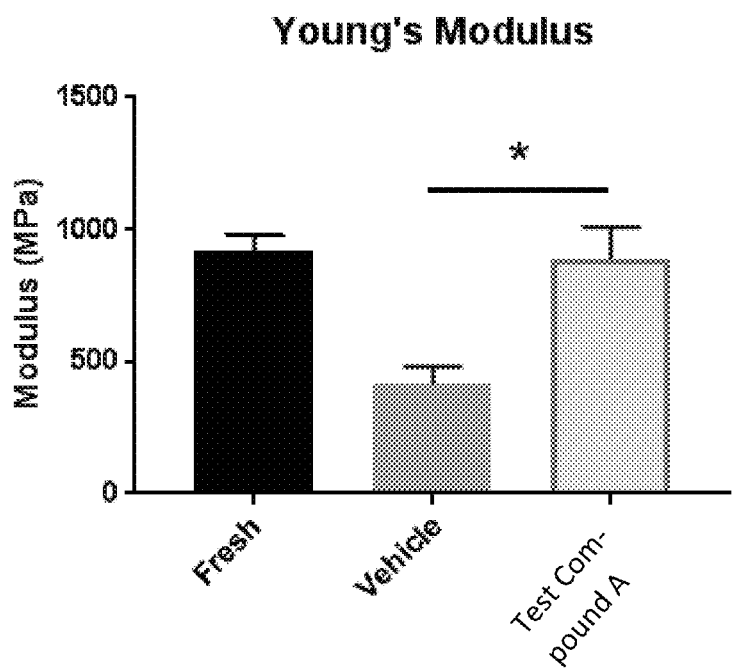
FIG. 1B shows the Young's Modulus data obtained with the compound of Example 32 ("Test Compound") in graphic form in an Ex vivo fascicle assay described in Example 93 (D).

Results:

In unloaded condition, tendon degeneration is observed in vitro shown by morphological changes in tendon structure and decrease in biomechanical properties (failure stress and young's modulus). Test Compound A could prevent the degeneration by maintaining both tendon structure and biomechanical properties for up to a month. Detailed results are shown in FIG. 1 (there Test Compound is Test Compound A).

Example 94: Microparticle Formulations

Microparticle formulations containing a copolymer of DL-lactide and glycolide in a 50:50 molar ratio (up to 75:25 molar ratio) and a molecular weight in the range of about 10 to 70 kDa with an inherent viscosity ranging from 0.15 to 0.60 dL/g with an ester or acid end group, either branched or linear or combination of two copolymers plus (S)-(1-((4-(3-amino-4-methyl-1H-indazol-5-yl)-3-methylphenyl)sulfonyl)-4,4-difluoropyrrolidin-2-yl)methanol (Test Compound A hereinafter) were formulated.

The total amount of Test Compound A incorporated into the microparticles ranged from 10% to 42% (w/w). The microparticles were formulated to mean mass range in size from 5 to 100 microns. The population of microparticles was formulated in syringes to be delivered through a 22 gauges or higher needles (see Table 4). Organic solvent used for preparation of microparticles were dichloromethane (DCM) and ethyl acetate (EA) either alone or in combination e.g., ratio of DCM to EA ranged from 5% to 50% (v/v).

The methods used for the manufacture of the microparticles are: First, in a step (a) a solution of Test Compound A was made by mixing it with the respective poly(lactic-co-glycolic) acid copolymer (PLGA) solution in DCM, DEA or both (in the examples in Table 4, 400 mg PLGA in 1.7 ml ethyl acetate). The solution was then, in a step (b), emulsified by adding 3.5 ml of PVA 1% (pH 7.4, PBS (phosphate Buffered Saline) buffer) to the organic phase under homogenization for 30 seconds (11,000 rpm) using an Ultraturrax homogenizer. The formed emulsion was diluted in 36.5 ml of the same PVA 1% under mild stirring (500 rpm). The emulsion was stirred (300 rpm) overnight under fume hood (no vacuum) using a heating chamber (22° C. to 60° C. in 9 hours and cooled down again to 22° C.) to remove the residual of organic solvent.

The resulting droplets where then, in a step (c), collected using centrifugation. The particles were centrifuged using 1000 rpm for 2 min and the supernatant was removed. Next, 40 ml of distilled water was added, followed by vortexing. This washing process was repeated 3 times.

In a further step (d), the resulting microparticles were then subjected to freeze drying overnight using a Christ® freeze drier (temperature −60° C. and 0.200 mbar pressure).

Finally, in a step (e), the resulting microparticles were sieved using a 150 micron sieve resulting in the microparticle formulations.

TABLE 4

| F | | Mw (kDa) | Drug loading (w/w) % | Amount and Solvent for PLGA (step (a); PLGA/Solvent (mg/ml) |
|---|---|---|---|---|
| | LGA types | | | |
| 1 | PLGA-504 (linear) | 34-58 | 10 (45 mg) | 400/1.7 |
| 2 | PLGA-504 (linear) | 34-58 | 20 (100 mg) | 400/1.7 |
| 3 | PLGA-G (branched) | 37-63 | 10 (45 mg) | 400/1.7 |
| 4 | PLGA-G (branched) | 37-63 | 20 (100 mg) | 400/1.7 |
| 5 | PLGA-G (branched) | 37-63 | 30 (172 mg) | 400/1.7 |
| | PLGA blend (linear and branched) w/w % | | | |
| 6 | PLGA-502/PLGA-G (25/75) | Mix | 10 (45 mg) | 400/1.7 |
| 7 | PLGA-502/PLGA-G (25/75) | Mix | 20 (100 mg) | 400/1.7 |
| 8 | PLGA-504/ PLGA-G (25/75) | Mix | 10 (45 mg) | 400/1.7 |
| 9 | PLGA-504/ PLGA-G (25/75) | Mix | 20 (100 mg) | 400/1.7 |
| 10 | PLGA-504/ PLGA-G (75/25) | Mix | 10 (45 mg) | 400/1.7 |
| 11 | PLGA-504/ PLGA-G (75/25) | Mix | 20 (100 mg) | 400/1.7 |
| 12 | Micronized Test Compound A | — | 25 mg/ml | — |

The PLGAs are specified as follows:

| PLGA-504 (linear) | RESOMER® RG 504 (Evonik) |
|---|---|
| PLGA-502 (linear) | RESOMER® RG 504 (Evonik) |
| PLGA-G (branched) | D,L-POLYMI/D-Glucose (Product of Novartis) |
| PLGA blend (linear and branched) w/w %: | constituents as just defined |
| PLGA-502/PLGA-G (25/75): | RESOMER® RG 502 D,L-POLYMI/D-Glucose |
| PLGA-504/PLGA-G (25/75): | RESOMER® RG-502/ D,L-POLYMI/D-Glucose |
| PLGA-504/PLGA-G (75/25) | RESOMER® RG-502/ D,L-POLYMI/D-Glucose |

Figure 2A:
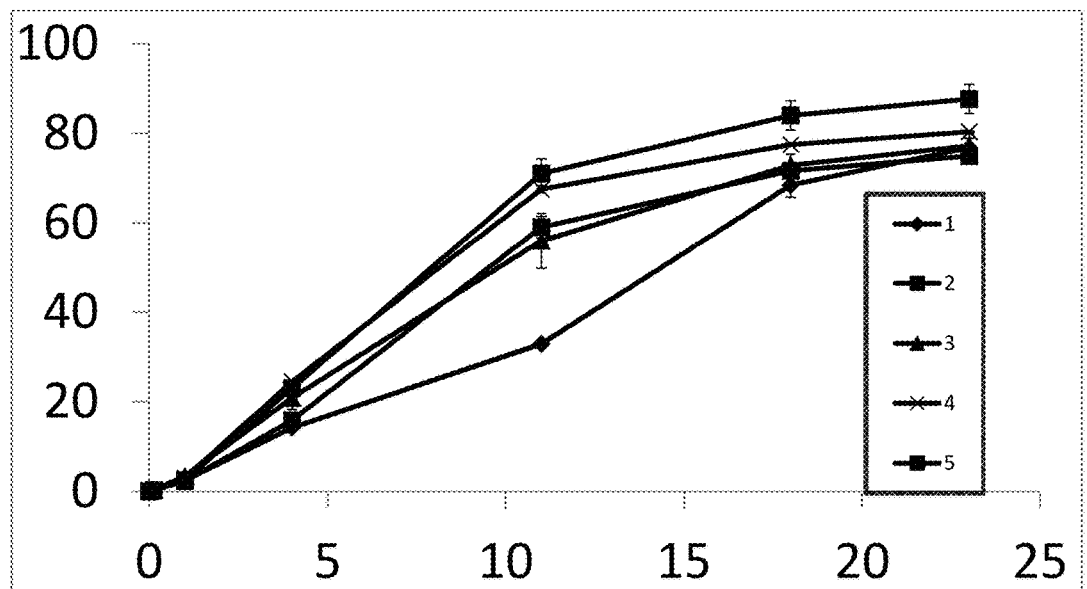
FIG. 2A shows a representation of Cumulative release of microparticle formulations (F=1-5) of the compound of Example 32 over time in PBS buffer pH 7.4, 1% (v/v) Tween® 20, first part, the numbers referring to the compositions numbers in Table 4.
Figure 2B:
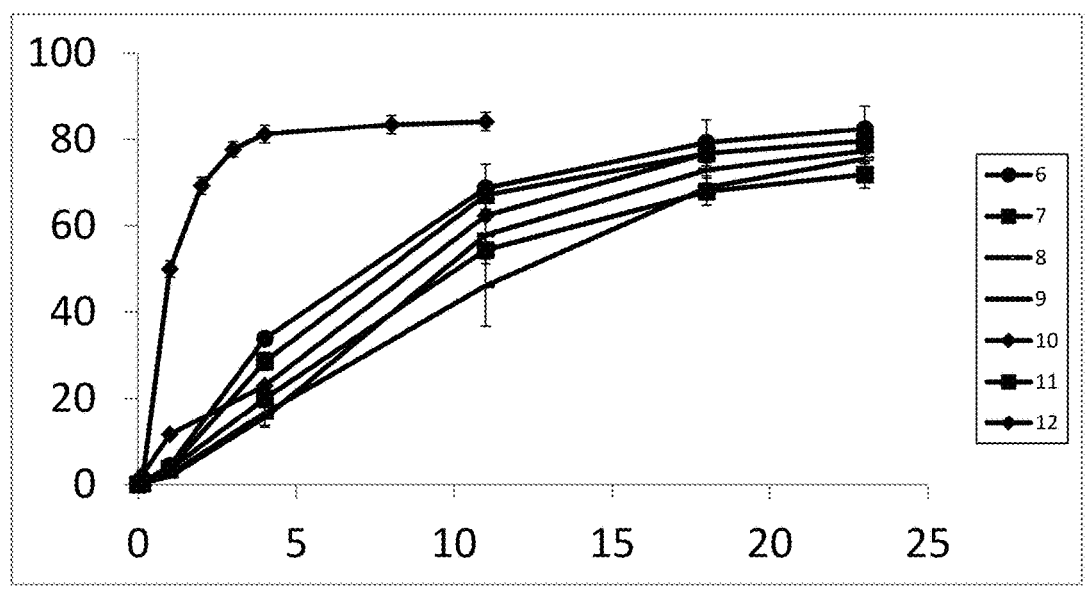
FIG. 2B shows a representation of Cumulative release of microparticle formulations (F=6-12) of the compound of Example 32 over time in PBS buffer pH 7.4, 1% (v/v) Tween® 20, first part, the numbers referring to the composition numbers in Table 4.

1 mg of Test Compound A incorporated into the microparticles was transferred into 21 ml of PBS buffer pH 7.4, Tween® 20 at 37° C. using the material of step (e) above, and provided an initial release (burst) of about 5-10% of drug over a period of 1 to 2 days in vitro, followed by a steady state release of drug over a period of 14 to 30 days (cf. FIGS. 2A and 2B).

In-vivo the microparticles could extend the release of Test Compound A over 3 weeks in a rat model. After injection close to the tendon significant improvement in tendon function was observed in this rat partial tenotomy model that was measured by imaging.

A gradient method was used to detect Test Compound A from released samples. The mobile phase A was 95% water and 5% Acetonitrile and mobile phase B was 5% water and 95% Acetonitrile both containing 0.05% trifluoroacetic acid. The column (Acquity UPLC BEH C18, 1.7 mm, Waters) temperature was set at 30° C. and Test Compound A was detected at lambda max of 220 nm and the retention time was at 5.8 min using an UPLC apparatus (Agilent) and chromeleon software. Test Compound A standard was prepared in the mixture of Acetonitrile/Water 50/50. See below for gradient method of mixing solvent:

| | | Time [min] | | | | | | |
|---|---|---|---|---|---|---|---|---|
| | | 0 | 1 | 8 | 10 | 11 | 11.1 | 13.0 |
| Gradient: | % B | 5 | 5 | 50 | 95 | 95 | 5 | 5 |

The invention claimed is:

1. A compound of formula (I):

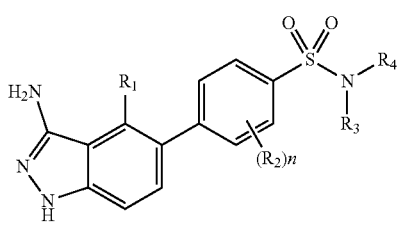

(I)

or a pharmaceutically acceptable salt thereof, wherein:

$R_1$ is selected from $C_1$-$C_3$alkyl, halogen and $C_1$-$C_3$alkoxy;

$R_2$ is independently selected from $C_1$-$C_3$alkyl and halogen;

$R_3$ is selected from H and $C_1$-$C_3$alkyl;

$R_4$ is selected from $C_4$-$C_6$cycloalkyl and 5- or 6-membered non-aromatic heterocyclic ring comprising at least one heteroatom selected from nitrogen, oxygen and sulfur, wherein said $C_4$-$C_6$cycloalkyl is optionally and independently substituted with one or more $R_5$ and said 5- or 6-membered non-aromatic heterocyclic ring is optionally and independently substituted with one or more hydroxy, $C_1$-$C_3$alkyl or $C_1$-$C_3$alkoxy; or $R_3$ and $R_4$, together with the nitrogen atom to which they are attached, form a 4-, 5- or 6-membered non-aromatic heterocyclic ring optionally comprising one additional heteroatom selected from nitrogen, oxygen and sulfur, wherein said 4-, 5- or 6-membered non-aromatic heterocyclic ring is substituted with one or more $R_6$;

$R_5$ is independently selected from hydroxy, halo$C_1$-$C_3$alkyl, halogen, $C_1$-$C_2$alkyl, phenyl, benzyl, $C_3$-$C_6$cycloalkyl and cyano;

$R_6$ is independently selected from halogen, hydroxy$C_1$-$C_3$alkyl, $C(O)NH_2$, hydroxy, $C_1$-$C_3$alkyl, cyano and halo$C_1$-$C_3$alkyl; and n is 1 or 2;

with the proviso that $R_4$ is not 4-hydroxycyclohexyl or tetrahydrofuran.

2. The compound according to claim 1, wherein the compound is of formula (I-1):

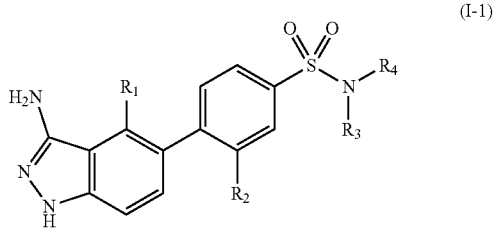

(I-1)

3. The compound according to claim 1, or a pharmaceutically acceptable salt thereof, wherein:

R₁ is selected from methyl, chloro, fluoro and methoxy; and

R₂ is independently selected from methyl and chloro.

4. The compound according to claim 1, or a pharmaceutically acceptable salt thereof, wherein:

R₃ is H; and

R₄ is C₄-C₆cycloalkyl, substituted with one or two R₅.

5. The compound according to claim 1, or a pharmaceutically acceptable salt thereof, wherein:

R₅ is independently selected from hydroxy, haloC₁-C₃alkyl, halogen and C₁-C₂alkyl.

6. The compound according to claim 1, or a pharmaceutically acceptable salt thereof, wherein:

R₃ and R₄, together with the nitrogen atom to which they are attached, form a 4-, 5- or 6-membered non-aromatic heterocyclic ring optionally comprising one additional heteroatom selected from nitrogen, oxygen and sulfur, substituted with one, two or three R₆.

7. The compound according to claim 1, or a pharmaceutically acceptable salt thereof, wherein:

R₆ is independently selected from halogen, hydroxyC₁-C₃alkyl, hydroxy and C₁-C₃alkyl.

8. The compound according to claim 1, wherein the compound is selected from the group consisting of:

5-(2-chloro-4-((3,3-dimethylazetidin-1-yl)sulfonyl)phenyl)-4-methyl-1H-indazol-3-amine;

1-((4-(3-amino-4-methyl-1H-indazol-5-yl)-3-chlorophenyl)sulfonyl)pyrrolidin-3-ol;

1-((4-(3-amino-4-methyl-1H-indazol-5-yl)-3-fluorophenyl)sulfonyl)pyrrolidin-3-ol;

1-((4-(3-amino-4-methyl-1H-indazol-5-yl)-3-methylphenyl)sulfonyl)pyrrolidin-3-ol;

1-((4-(3-amino-4-chloro-1H-indazol-5-yl)-3-fluorophenyl)sulfonyl)pyrrolidin-3-ol;

1-((4-(3-amino-4-chloro-1H-indazol-5-yl)-3-methylphenyl)sulfonyl)pyrrolidin-3-ol;

1-((4-(3-amino-4-chloro-1H-indazol-5-yl)-3-chlorophenyl)sulfonyl)pyrrolidin-3-ol;

4-(3-amino-4-methyl-1H-indazol-5-yl)-N-(3-hydroxycyclobutyl)-3-methylbenzenesulfonamide;

1-(4-(3-amino-4-methyl-1H-indazol-5-yl)-3-methylphenyl)sulfonyl)azetidin-2-yl)methanol;

1-((4-(3-amino-4-methyl-1H-indazol-5-yl)-3-methylphenyl)sulfonyl)azetidin-3-ol;

1-((4-(3-amino-4-methyl-1H-indazol-5-yl)-3-methylphenyl)sulfonyl)-3-methylazetidin-3-ol;

1-((4-(3-amino-4-methyl-1H-indazol-5-yl)-3-methylphenyl)sulfonyl)piperidin-4-ol;

4-(3-amino-4-methyl-1H-indazol-5-yl)-N-(2-hydroxycyclopentyl)-3-methylbenzenesulfonamide;

4-(3-amino-4-methyl-1H-indazol-5-yl)-N-(2-hydroxycyclohexyl)-3-methylbenzenesulfonamide;

1-((4-(3-amino-4-methyl-1H-indazol-5-yl)-3-methylphenyl)sulfonyl)pyrrolidin-2-yl)methanol;

4-(3-amino-4-methyl-1H-indazol-5-yl)-3-methyl-N-(tetrahydro-2H-pyran-4-yl)benzenesulfonamide;

1-((4-(3-amino-4-methyl-1H-indazol-5-yl)-3-methylphenyl)sulfonyl)azetidine-3-carbonitrile;

1-((4-(3-amino-4-methyl-1H-indazol-5-yl)-3-methylphenyl)sulfonyl)piperidine-4-carbonitrile;

4-(3-amino-4-methyl-1H-indazol-5-yl)-N-(3,3-difluorocyclobutyl)-3-methylbenzenesulfonamide;

4-(3-amino-4-methyl-1H-indazol-5-yl)-N-(3-hydroxycyclohexyl)-3-methylbenzenesulfonamide;

4-(3-amino-4-methyl-1H-indazol-5-yl)-N-(3-cyanocyclohexyl)-3-methylbenzenesulfonamide;

4-(3-amino-4-methyl-1H-indazol-5-yl)-N-(4-cyanocyclohexyl)-3-methylbenzenesulfonamide;

1-((4-(3-amino-4-chloro-1H-indazol-5-yl)-3-methylphenyl)sulfonyl)pyrrolidin-2-yl)methanol;

4-(3-amino-4-chloro-1H-indazol-5-yl)-N-(2-hydroxycyclopentyl)-3-methylbenzenesulfonamide;

4-(3-amino-4-chloro-1H-indazol-5-yl)-N-(3-hydroxycyclobutyl)-3-methylbenzenesulfonamide;

4-(3-amino-4-methyl-1H-indazol-5-yl)-N-(3-hydroxy-3-(trifluoromethyl)cyclobutyl)-3-methylbenzenesulfonamide;

1-((4-(3-amino-4-methyl-1H-indazol-5-yl)-3-methylphenyl)sulfonyl)-4,4-difluoropyrrolidin-2-yl)methanol;

1-((4-(3-amino-4-methyl-1H-indazol-5-yl)-3-methylphenyl)sulfonyl)-4-fluoro-2,5-dihydro-1H-pyrrol-2-yl)methanol;

4-(3-amino-4-methyl-1H-indazol-5-yl)-3-chloro-N-(3-hydroxycyclobutyl)benzenesulfonamide;

4-(3-amino-4-methyl-1H-indazol-5-yl)-N-(3-hydroxycyclopentyl)-3-methylbenzenesulfonamide;

4-(3-amino-4-methyl-1H-indazol-5-yl)-N-(3-hydroxy-1-methylcyclobutyl)-3-methylbenzenesulfonamide;

4-(3-amino-4-chloro-1H-indazol-5-yl)-N-(3-hydroxy-3-(trifluoromethyl)cyclobutyl)-3-methylbenzenesulfonamide;

4-(3-amino-4-methyl-1H-indazol-5-yl)-N-(4,4-difluorocyclohexyl)-3-methylbenzenesulfonamide;

1-((4-(3-amino-4-methyl-1H-indazol-5-yl)-3-chlorophenyl)sulfonyl)pyrrolidin-2-yl)methanol;

4-(3-amino-4-methyl-1H-indazol-5-yl)-3-chloro-N-(2-hydroxycyclopentyl)benzenesulfonamide;

4-(3-amino-4-methyl-1H-indazol-5-yl)-N-(3-hydroxy-3-methylcyclobutyl)-3-methylbenzenesulfonamide;

1-((4-(3-amino-4-methoxy-1H-indazol-5-yl)-3-fluorophenyl)sulfonyl)-4,4-difluoropyrrolidin-2-yl)methanol;

1-((4-(3-amino-4-methyl-1H-indazol-5-yl)-3-fluorophenyl)sulfonyl)-4,4-difluoropyrrolidin-2-yl)methanol;

4-(3-amino-4-methyl-1H-indazol-5-yl)-N-(4,4-difluorocyclohexyl)-3-methylbenzenesulfonamide;

1-((4-(3-amino-4-fluoro-1H-indazol-5-yl)-3-methylphenyl)sulfonyl)-4,4-difluoropyrrolidin-2-yl)methanol;

4-(3-amino-4-methyl-1H-indazol-5-yl)-N-(4-hydroxytetrahydro-2H-pyran-3-yl)-3-methylbenzenesulfonamide;

1-((4-(3-amino-4-fluoro-1H-indazol-5-yl)-3-chlorophenyl)sulfonyl)-4,4-difluoropyrrolidin-2-yl)methanol;

1-((4-(3-amino-4-chloro-1H-indazol-5-yl)-3-fluorophenyl)sulfonyl)-4,4-difluoropyrrolidin-2-yl)methanol;

4-(3-amino-4-methyl-1H-indazol-5-yl)-N-(2-hydroxycyclopentyl)-3-methylbenzenesulfonamide;

4-(3-amino-4-methyl-1H-indazol-5-yl)-N-(3-ethyl-3-hydroxycyclobutyl)-3-methylbenzenesulfonamide;

4-(3-amino-4-methyl-1H-indazol-5-yl)-N-(3-cyclopropyl-3-hydroxycyclobutyl)-3-methylbenzenesulfonamide;

4-(3-amino-4-methyl-1H-indazol-5-yl)-N-(3-benzyl-3-hydroxycyclobutyl)-3-methylbenzenesulfonamide;

4-(3-amino-4-methyl-1H-indazol-5-yl)-N-(3-hydroxy-3-phenylcyclobutyl)-3-methylbenzenesulfonamide;

1-((4-(3-amino-4-chloro-1H-indazol-5-yl)-3-chlorophenyl)sulfonyl)-4,4-difluoropyrrolidin-2-yl)methanol;

1-((4-(3-amino-4-chloro-1H-indazol-5-yl)-3-methylphenyl)sulfonyl)-4,4-difluoropyrrolidin-2-yl)methanol;

4-(3-amino-4-methyl-1H-indazol-5-yl)-3-chloro-N-(3-hydroxy-3-(trifluoromethyl)cyclobutyl)benzenesulfonamide;

1-((4-(3-amino-4-methyl-1H-indazol-5-yl)-3-chlorophenyl)sulfonyl)-4,4-difluoropyrrolidin-2-yl)methanol;
1-((4-(3-amino-4-methyl-1H-indazol-5-yl)-3-methylphenyl)sulfonyl)-3-methylpyrrolidin-3-ol;
4-(3-amino-4-methyl-1H-indazol-5-yl)-N-(2-hydroxy-2-methylcyclopentyl)-3-methylbenzenesulfonamide;
1-(1-((4-(3-amino-4-methyl-1H-indazol-5-yl)-3-methylphenyl)sulfonyl)pyrrolidin-2-yl)ethan-1-ol;
1-((4-(3-amino-4-fluoro-1H-indazol-5-yl)-3-fluorophenyl)sulfonyl)-4,4-difluoropyrrolidin-2-yl)methanol;
1-((4-(3-amino-4-methyl-1H-indazol-5-yl)-3-methylphenyl)sulfonyl)-3-(trifluoromethyl)pyrrolidin-3-ol;
4-(3-amino-4-methyl-1H-indazol-5-yl)-N-(3,3-difluorocyclobutyl)-N,3-dimethylbenzenesulfonamide;
4-(3-amino-4-chloro-1H-indazol-5-yl)-3-chloro-N-(3-hydroxy-3-(trifluoromethyl)cyclobutyl)benzenesulfonamide;
4-(3-amino-4-methoxy-1H-indazol-5-yl)-3-chloro-N-(3-hydroxy-3-(trifluoromethyl)cyclobutyl)benzenesulfonamide;
4-(3-amino-4-chloro-1H-indazol-5-yl)-N-(3,3-difluorocyclobutyl)-3-methylbenzenesulfonamide;
4-(3-amino-4-chloro-1H-indazol-5-yl)-3-chloro-N-(3,3-difluorocyclobutyl)benzenesulfonamide;
4-(3-amino-4-methyl-1H-indazol-5-yl)-3-chloro-N-(3,3-difluorocyclobutyl)benzenesulfonamide;
4-(3-amino-4-chloro-1H-indazol-5-yl)-3-chloro-N-(2-hydroxycyclopentyl)benzenesulfonamide;
4-(3-amino-4-methoxy-1H-indazol-5-yl)-N-(3-hydroxy-3-(trifluoromethyl)cyclobutyl)-3-methylbenzenesulfonamide;
4-(3-amino-4-fluoro-1H-indazol-5-yl)-N-(3-hydroxy-3-(trifluoromethyl)cyclobutyl)-3-methylbenzenesulfonamide;
4-(3-amino-4-fluoro-1H-indazol-5-yl)-3-chloro-N-(3-hydroxy-3-(trifluoromethyl)cyclobutyl)benzenesulfonamide;
4-(3-amino-4-methoxy-1H-indazol-5-yl)-N-(2-hydroxycyclopentyl)-3-methylbenzenesulfonamide;
4-(3-amino-4-methoxy-1H-indazol-5-yl)-3-chloro-N-(2-hydroxycyclopentyl)benzenesulfonamide;
4-(3-amino-4-fluoro-1H-indazol-5-yl)-N-(2-hydroxycyclopentyl)-3-methylbenzenesulfonamide;
4-(3-amino-4-fluoro-1H-indazol-5-yl)-3-chloro-N-(2-hydroxycyclopentyl)benzenesulfonamide;
5-(4-((3,3-difluoropyrrolidin-1-yl)sulfonyl)-2-methylphenyl)-4-methyl-1H-indazol-3-amine;
5-(4-((3,3-difluoroazetidin-1-yl)sulfonyl)-2-methylphenyl)-4-methyl-1H-indazol-3-amine;
5-(4-((3,3-difluoropiperidin-1-yl)sulfonyl)-2-methylphenyl)-4-methyl-1H-indazol-3-amine
5-(4-((4,4-difluoropiperidin-1-yl)sulfonyl)-2-methylphenyl)-4-methyl-1H-indazol-3-amine;
1-((4-(3-amino-4-methyl-1H-indazol-5-yl)-3-methylphenyl)sulfonyl)-4,4-difluoropyrrolidine-2-carboxamide;
Meso-5-(4-((3,4-difluoropyrrolidin-1-yl)sulfonyl)-2-methylphenyl)-4-methyl-1H-indazol-3-amine;
4-(3-amino-4-methyl-1H-indazol-5-yl)-N-(3-hydroxy-3-(trifluoromethyl)cyclobutyl)-N,3-dimethylbenzenesulfonamide;
4-(3-amino-4-methyl-1H-indazol-5-yl)-N-(2-hydroxycyclopentyl)-N,3-dimethylbenzenesulfonamide;
1-((4-(3-amino-4-methoxy-1H-indazol-5-yl)-3-methylphenyl)sulfonyl)-4,4-difluoropyrrolidin-2-yl)methanol;
1-((4-(3-amino-4-methoxy-1H-indazol-5-yl)-3-chlorophenyl)sulfonyl)-4,4-difluoropyrrolidin-2-yl)methanol;
1-((4-(3-amino-4-methyl-1H-indazol-5-yl)-3-methylphenyl)sulfonyl)-4-fluoropyrrolidin-2-yl)methanol;
1-((4-(3-amino-4-methyl-1H-indazol-5-yl)-3,5-difluorophenyl)sulfonyl)-4,4-difluoropyrrolidin-2-yl)methanol;
1-((4-(3-amino-4-methyl-1H-indazol-5-yl)-2-fluorophenyl)sulfonyl)-4,4-difluoropyrrolidin-2-yl)methanol; and
1-((4-(3-amino-4-methyl-1H-indazol-5-yl)-2-methylphenyl)sulfonyl)-4,4-difluoropyrrolidin-2-yl)methanol,
or a pharmaceutically acceptable salt thereof.

9. The compound according to claim 8, wherein the compound is selected from the group consisting of:
(R)-1-((4-(3-amino-4-methyl-1H-indazol-5-yl)-3-chlorophenyl)sulfonyl)pyrrolidin-3-ol;
(R)-1-((4-(3-amino-4-methyl-1H-indazol-5-yl)-3-methylphenyl)sulfonyl)pyrrolidin-3-ol;
(S)-1-((4-(3-amino-4-methyl-1H-indazol-5-yl)-3-methylphenyl)sulfonyl)pyrrolidin-3-ol;
(R)-1-((4-(3-amino-4-chloro-1H-indazol-5-yl)-3-fluorophenyl)sulfonyl)pyrrolidin-3-ol;
(R)-1-((4-(3-amino-4-chloro-1H-indazol-5-yl)-3-methylphenyl)sulfonyl)pyrrolidin-3-ol;
(R)-1-((4-(3-amino-4-chloro-1H-indazol-5-yl)-3-chlorophenyl)sulfonyl)pyrrolidin-3-ol;
4-(3-amino-4-methyl-1H-indazol-5-yl)-N-((1r,3r)-3-hydroxycyclobutyl)-3-methylbenzenesulfonamide;
(S)-(1-((4-(3-amino-4-methyl-1H-indazol-5-yl)-3-methylphenyl)sulfonyl)azetidin-2-yl)methanol;
4-(3-amino-4-methyl-1H-indazol-5-yl)-N-((1s,3s)-3-hydroxycyclobutyl)-3-methylbenzenesulfonamide;
4-(3-amino-4-methyl-1H-indazol-5-yl)-N-((1R,2R)-2-hydroxycyclopentyl)-3-methylbenzenesulfonamide;
4-(3-amino-4-methyl-1H-indazol-5-yl)-N-((1R,2R)-2-hydroxycyclohexyl)-3-methylbenzenesulfonamide;
4-(3-amino-4-methyl-1H-indazol-5-yl)-N-((1R,2S)-2-hydroxycyclohexyl)-3-methylbenzenesulfonamide;
4-(3-amino-4-methyl-1H-indazol-5-yl)-N-((1R,2S)-2-hydroxycyclopentyl)-3-methylbenzenesulfonamide;
(S)-(1-((4-(3-amino-4-methyl-1H-indazol-5-yl)-3-methylphenyl)sulfonyl)pyrrolidin-2-yl)methanol;
(R)-(1-((4-(3-amino-4-methyl-1H-indazol-5-yl)-3-methylphenyl)sulfonyl)pyrrolidin-2-yl)methanol;
4-(3-amino-4-methyl-1H-indazol-5-yl)-N-((1R,3R)-3-cyanocyclohexyl)-3-methylbenzenesulfonamide;
4-(3-amino-4-methyl-1H-indazol-5-yl)-N-((1s,4s)-4-cyanocyclohexyl)-3-methylbenzenesulfonamide;
(S)-(1-((4-(3-amino-4-chloro-1H-indazol-5-yl)-3-methylphenyl)sulfonyl)pyrrolidin-2-yl)methanol;
4-(3-amino-4-chloro-1H-indazol-5-yl)-N-((1R,2S)-2-hydroxycyclopentyl)-3-methylbenzenesulfonamide;
4-(3-amino-4-chloro-1H-indazol-5-yl)-N-((1s,3s)-3-hydroxycyclobutyl)-3-methylbenzenesulfonamide;
4-(3-amino-4-methyl-1H-indazol-5-yl)-N-((1s,3s)-3-hydroxy-3-(trifluoromethyl)cyclobutyl)-3-methylbenzenesulfonamide;
(S)-(1-((4-(3-amino-4-methyl-1H-indazol-5-yl)-3-methylphenyl)sulfonyl)-4,4-difluoropyrrolidin-2-yl)methanol;
(S)-(1-((4-(3-amino-4-methyl-1H-indazol-5-yl)-3-methylphenyl)sulfonyl)-4-fluoro-2,5-dihydro-1H-pyrrol-2-yl)methanol;
4-(3-amino-4-methyl-1H-indazol-5-yl)-3-chloro-N-((1s,3s)-3-hydroxycyclobutyl)benzenesulfonamide;

4-(3-amino-4-methyl-1H-indazol-5-yl)-N-((1R,3S)-3-hydroxycyclopentyl)-3-methylbenzenesulfonamide;
4-(3-amino-4-methyl-1H-indazol-5-yl)-N-((1s,3s)-3-hydroxy-1-methylcyclobutyl)-3-methylbenzenesulfonamide;
4-(3-amino-4-chloro-1H-indazol-5-yl)-N-((1s,3s)-3-hydroxy-3-(trifluoromethyl)cyclobutyl)-3-methylbenzenesulfonamide;
(S)-(1-((4-(3-amino-4-methyl-1H-indazol-5-yl)-3-chlorophenyl)sulfonyl)pyrrolidin-2-yl)methanol;
4-(3-amino-4-methyl-1H-indazol-5-yl)-3-chloro-N-((1R,2S)-2-hydroxycyclopentyl)benzenesulfonamide;
4-(3-amino-4-methyl-1H-indazol-5-yl)-N-((1s,3s)-3-hydroxy-3-methylcyclobutyl)-3-methylbenzenesulfonamide;
(S)-(1-((4-(3-amino-4-methoxy-1H-indazol-5-yl)-3-fluorophenyl)sulfonyl)-4,4-difluoropyrrolidin-2-yl)methanol;
(S)-(1-((4-(3-amino-4-methyl-1H-indazol-5-yl)-3-fluorophenyl)sulfonyl)-4,4-difluoropyrrolidin-2-yl)methanol;
(S)-(1-((4-(3-amino-4-fluoro-1H-indazol-5-yl)-3-methylphenyl)sulfonyl)-4,4-difluoropyrrolidin-2-yl)methanol;
4-(3-amino-4-methyl-1H-indazol-5-yl)-N-((3R,4R)-4-hydroxytetrahydro-2H-pyran-3-yl)-3-methylbenzenesulfonamide;
(S)-(1-((4-(3-amino-4-fluoro-1H-indazol-5-yl)-3-chlorophenyl)sulfonyl)-4,4-difluoropyrrolidin-2-yl)methanol;
(S)-(1-((4-(3-amino-4-chloro-1H-indazol-5-yl)-3-fluorophenyl)sulfonyl)-4,4-difluoropyrrolidin-2-yl)methanol;
4-(3-amino-4-methyl-1H-indazol-5-yl)-N-((1S,2R)-2-hydroxycyclopentyl)-3-methylbenzenesulfonamide;
(S)-(1-((4-(3-amino-4-chloro-1H-indazol-5-yl)-3-chlorophenyl)sulfonyl)-4,4-difluoropyrrolidin-2-yl)methanol;
(S)-(1-((4-(3-amino-4-chloro-1H-indazol-5-yl)-3-methylphenyl)sulfonyl)-4,4-difluoropyrrolidin-2-yl)methanol;
4-(3-amino-4-methyl-1H-indazol-5-yl)-3-chloro-N-((1s,3s)-3-hydroxy-3-(trifluoromethyl)cyclobutyl)benzenesulfonamide;
(S)-(1-((4-(3-amino-4-methyl-1H-indazol-5-yl)-3-chlorophenyl)sulfonyl)-4,4-difluoropyrrolidin-2-yl)methanol;
4-(3-amino-4-methyl-1H-indazol-5-yl)-N-((1S,2S)-2-hydroxy-2-methylcyclopentyl)-3-methylbenzenesulfonamide;
4-(3-amino-4-methyl-1H-indazol-5-yl)-N-((1S,2R)-2-hydroxy-2-methylcyclopentyl)-3-methylbenzenesulfonamide;
1-((S)-1-((4-(3-amino-4-methyl-1H-indazol-5-yl)-3-methylphenyl)sulfonyl)pyrrolidin-2-yl)ethan-1-ol;
(S)-(1-((4-(3-amino-4-fluoro-1H-indazol-5-yl)-3-fluorophenyl)sulfonyl)-4,4-difluoropyrrolidin-2-yl)methanol;
4-(3-amino-4-chloro-1H-indazol-5-yl)-3-chloro-N-((1s,3s)-3-hydroxy-3-(trifluoromethyl)cyclobutyl)benzenesulfonamide;
4-(3-amino-4-methoxy-1H-indazol-5-yl)-3-chloro-N-((1s,3s)-3-hydroxy-3-(trifluoromethyl)cyclobutyl)benzenesulfonamide;
4-(3-amino-4-chloro-1H-indazol-5-yl)-3-chloro-N-((1R,2S)-2-hydroxycyclopentyl)benzenesulfonamide;
4-(3-amino-4-methoxy-1H-indazol-5-yl)-N-((1s,3s)-3-hydroxy-3-(trifluoromethyl)cyclobutyl)-3-methylbenzenesulfonamide;
4-(3-amino-4-fluoro-1H-indazol-5-yl)-N-((1s,3s)-3-hydroxy-3-(trifluoromethyl)cyclobutyl)-3-methylbenzenesulfonamide;
4-(3-amino-4-fluoro-1H-indazol-5-yl)-3-chloro-N-((1s,3s)-3-hydroxy-3-(trifluoromethyl)cyclobutyl)benzenesulfonamide;
4-(3-amino-4-methoxy-1H-indazol-5-yl)-N-((1R,2S)-2-hydroxycyclopentyl)-3-methylbenzenesulfonamide;
4-(3-amino-4-methoxy-1H-indazol-5-yl)-3-chloro-N-((1R,2S)-2-hydroxycyclopentyl)benzenesulfonamide;
4-(3-amino-4-fluoro-1H-indazol-5-yl)-N-((1R,2S)-2-hydroxycyclopentyl)-3-methylbenzenesulfonamide;
4-(3-amino-4-fluoro-1H-indazol-5-yl)-3-chloro-N-((1R,2S)-2-hydroxycyclopentyl)benzenesulfonamide;
(S)-1-((4-(3-amino-4-methyl-1H-indazol-5-yl)-3-methylphenyl)sulfonyl)-4,4-difluoropyrrolidine-2-carboxamide;
Meso-5-(4-(((3R,4S)-3,4-difluoropyrrolidin-1-yl)sulfonyl)-2-methylphenyl)-4-methyl-1H-indazol-3-amine;
4-(3-amino-4-methyl-1H-indazol-5-yl)-N-((1s,3s)-3-hydroxy-3-(trifluoromethyl)cyclobutyl)-N,3-dimethylbenzenesulfonamide;
4-(3-amino-4-methyl-1H-indazol-5-yl)-N-((1R,2S)-2-hydroxycyclopentyl)-N,3-dimethylbenzenesulfonamide;
(S)-(1-((4-(3-amino-4-methoxy-1H-indazol-5-yl)-3-methylphenyl)sulfonyl)-4,4-difluoropyrrolidin-2-yl)methanol;
(S)-(1-((4-(3-amino-4-methoxy-1H-indazol-5-yl)-3-chlorophenyl)sulfonyl)-4,4-difluoropyrrolidin-2-yl)methanol;
((2S,4R)-1-((4-(3-amino-4-methyl-1H-indazol-5-yl)-3-methylphenyl)sulfonyl)-4-fluoropyrrolidin-2-yl)methanol;
(R)-(1-((4-(3-amino-4-methyl-1H-indazol-5-yl)-3-methylphenyl)sulfonyl)-4,4-difluoropyrrolidin-2-yl)methanol;
(S)-(1-((4-(3-amino-4-methyl-1H-indazol-5-yl)-3,5-difluorophenyl)sulfonyl)-4,4-difluoropyrrolidin-2-yl)methanol;
(S)-(1-((4-(3-amino-4-methyl-1H-indazol-5-yl)-2-fluorophenyl)sulfonyl)-4,4-difluoropyrrolidin-2-yl)methanol;
(S)-(1-((4-(3-amino-4-methyl-1H-indazol-5-yl)-2-methylphenyl)sulfonyl)-4,4-difluoropyrrolidin-2-yl)methanol; and
((2S,4S)-1-((4-(3-amino-4-methyl-1H-indazol-5-yl)-3-methylphenyl)sulfonyl)-4-fluoropyrrolidin-2-yl)methanol,
or a pharmaceutically acceptable salt thereof.

10. A pharmaceutical composition comprising a therapeutically effective amount of a compound according to claim 1, or a pharmaceutically acceptable salt thereof, and one or more pharmaceutically acceptable carriers.

11. The pharmaceutical pharmaceutical composition according to claim 10, wherein the composition is in the form of a sustained release formulation.

12. The pharmaceutical pharmaceutical composition according to claim 11, wherein the composition is formulated for injection.

13. The pharmaceutical composition according to claim 12, wherein the pharmaceutical composition is in the form of a microparticle formulation comprising as an active ingredient a therapeutically effective amount of a compound according to claim 1, or a pharmaceutically acceptable salt thereof, and one or more polylactide-co-glycolide polymers.

14. A pharmaceutical combination comprising a therapeutically effective amount of a compound according to claim 1, or a pharmaceutically acceptable salt thereof, and one or more therapeutically active agents.

15. A method for treating a tendon injury in a subject, wherein the method comprises administering to a subject in need thereof a therapeutically effective amount of a compound according to claim 1, or a pharmaceutically acceptable salt thereof.

16. A method for treating a ligament injury in a subject, wherein the method comprises administering to a subject in need thereof a therapeutically effective amount of a compound according to claim 1, or a pharmaceutically acceptable salt thereof.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: Rattus norvegicus

<400> SEQUENCE: 1
atcaccatct tccaggagcg a                                              21

<210> SEQ ID NO 2
<211> LENGTH: 18
<212> TYPE: DNA
<213> ORGANISM: Rattus norvegicus

<400> SEQUENCE: 2
gatgcccagg gaagacag                                                  18

<210> SEQ ID NO 3
<211> LENGTH: 18
<212> TYPE: DNA
<213> ORGANISM: Rattus norvegicus

<400> SEQUENCE: 3
gctcctcctg agcgcaag                                                  18

<210> SEQ ID NO 4
<211> LENGTH: 20
<212> TYPE: DNA
<213> ORGANISM: Rattus norvegicus

<400> SEQUENCE: 4
cccaaacaga tctgcacctt                                                20

<210> SEQ ID NO 5
<211> LENGTH: 21
<212> TYPE: DNA
<213> ORGANISM: Rattus norvegicus

<400> SEQUENCE: 5
tggatcaatc ccactctaat a                                              21

<210> SEQ ID NO 6
<211> LENGTH: 19
<212> TYPE: DNA
<213> ORGANISM: Rattus norvegicus

<400> SEQUENCE: 6
cctggctctc gaggtgaac                                                 19

<210> SEQ ID NO 7
<211> LENGTH: 21
<212> TYPE: DNA
<213> ORGANISM: Rattus norvegicus

<400> SEQUENCE: 7
agccttctcc atggtggtga a                                              21

<210> SEQ ID NO 8
<211> LENGTH: 22
<212> TYPE: DNA
<213> ORGANISM: Rattus norvegicus

```
<400> SEQUENCE: 8
cacaatgaag cattttgggt ag                                           22

<210> SEQ ID NO 9
<211> LENGTH: 20
<212> TYPE: DNA
<213> ORGANISM: Rattus norvegicus

<400> SEQUENCE: 9
catctgctgg aaggtggaca                                              20

<210> SEQ ID NO 10
<211> LENGTH: 20
<212> TYPE: DNA
<213> ORGANISM: Rattus norvegicus

<400> SEQUENCE: 10
tctgtcacgg tctttgctca                                              20

<210> SEQ ID NO 11
<211> LENGTH: 21
<212> TYPE: DNA
<213> ORGANISM: Rattus norvegicus

<400> SEQUENCE: 11
tcgctggtag gaaagtgaag a                                            21

<210> SEQ ID NO 12
<211> LENGTH: 18
<212> TYPE: DNA
<213> ORGANISM: Rattus norvegicus

<400> SEQUENCE: 12
caatgcccag aggaccag                                                18
```